(12) United States Patent
Rommens et al.

(10) Patent No.: US 7,785,777 B2
(45) Date of Patent: Aug. 31, 2010

(54) DIAGNOSIS OF SHWACHMAN-DIAMOND SYNDROME

(75) Inventors: Johanna M. Rommens, Toronto (CA); Peter R. Durie, Toronto (CA)

(73) Assignee: The Hospital for Sick Children, Toronto (CA)

( * ) Notice: Subject to any disclaimer, the term of this patent is extended or adjusted under 35 U.S.C. 154(b) by 697 days.

(21) Appl. No.: 10/526,429

(22) PCT Filed: Aug. 29, 2003

(86) PCT No.: PCT/CA03/01320

§ 371 (c)(1),
(2), (4) Date: Nov. 2, 2005

(87) PCT Pub. No.: WO2004/020658

PCT Pub. Date: Mar. 11, 2004

(65) Prior Publication Data

US 2006/0110734 A1 May 25, 2006

(51) Int. Cl.
C12Q 1/68 (2006.01)
C12P 19/34 (2006.01)
(52) U.S. Cl. .......................................... 435/6; 435/91.2
(58) Field of Classification Search ....................... None
See application file for complete search history.

(56) References Cited

FOREIGN PATENT DOCUMENTS

EP 1 074 617 A 7/2001

OTHER PUBLICATIONS

Woloszynek et al. Mutations of the SBDS gene are present in most patients with Shwachman-Diamond syndrome. Blood (2004) 104, No. 12, pp. 3588-3590.*
Nishimura et al. The Shwachman-Bodian-Diamond syndrome gene mutations cause a neonatal form of spondylometaphysical dysplasia (SMD) resembling SMD Sedaghatian type. J. Med. Genet. (2007) 44:e73, pp. 1-5.*
Costa et al. Hematologically important mutations: Shwachman-Diamond syndrome. Blood Cells, Molecules and Disease (2008) 40:183-184.*
Shwachman, H., Diamond, L.K. & Khaw, K., (1964), "The Syndrome of Pancreatic Insufficiency and Bone Marrow Dysfunction", J. Pediatr. v. 65, pp. 645-663.
Ginzberg, H. et al., (1999), "Shwachman Syndrome: Phenotypic Manifestations of Sibling Sets and Isolated Cases in a Large Patient Cohort are Similar", J. Pediatr. v. 135, pp. 81-88.
Ginzberg, H. et al., (2000), "Segregation analysis in Shwachman-Diamond Syndrome: Evidence for Recessive Inheritance", Am. J. Hum. Genet, v. 66, pp. 1413-1416.
Goobie, S. et al., (2001), "Shwachman-Diamond syndrome with exocrine pancreatic dysfunction and bone marrow failure maps to the centromeric region of chromosome 7", Am. J. Hum. Genet, v. 68, pp. 1048-1054.

Popovic, M. et al., (2002), "Fine mapping of the locus for Shwachman-Diamond syndrome at 7q11, identification of shared disease haplotypes, and exclusion of TPST1 as a candidate gene", Eur. J. Hum. Genet, v. 10, pp. 250-258.
Koonin, E.V., Wolf, Y.I. & Aravind, L. (2001), "Prediction of the archaeal exosome and its connections with the proteasome and the translation and transcription machineries by a comparative-genomic approach". Genome Res. 11, 240-252.
Roesler, J. et al., (2000), "Recombination events between the p47-phox gene and its highly homologous pseudogenes are the main cause of autosomal recessive chronic granulomatous disease". Blood., v. 15, pp. 2150-2156.
Strachan T., (1994), "Molecular pathology of 21-hydroxylase deficiency", J. Inherit. Metab. Dis., v. 17, pp. 430-441.
New, M.I., (1994), "Steroid 21-hydroxylase deficiency (congenital adrenal hyperplasia)", Am. J. Med., v. 98(1A), pp. 1A-2S-1A-8S.
Beutler, E., (1993), "Gaucher disease as a paradigm of current issues regarding single gene mutations of humans", Proc. Natl. Acad. Sci. USA., v. 90, pp. 5384-5390.
Eikenboom, J.C., et al., (1994), "Multiple substitutions in the von Willebrand factor gene that mimic the pseudogene sequence", Proc. Natl. Acad. Sci. USA., v. 91, pp. 2221-2224.
Watnick, T. J., et al., (1998), "Gene conversion is a likely cause of mutation in PKD1"., Hum. Mol. Genet., v. 7, pp. 1239-1243.
Chen, J. M. and Ferec, C., (2000), "Molecular basis of hereditary pancreatitis", Eur. J. Hum. Genet., v. 8, pp. 473-479.
Chen, J. M., et al., (2000), "A CGC>CAT gene conversion-like event resulting in the R122H mutation in the cationic trypsinogen gene and its implication in the genotyping of pancreatitis", J. Med. Genet., v. 37, E36.
Cai, L. et al., (2001), "A novel Q378X mutation exists in the transmembrane transporter protein ABCC6 and its pseudogene: implications for mutation analysis in pseudoxanthoma elasticum", J. Mol. Med., v. 79, pp. 536-546.
Bunge, S., et al., (1998), "Homologous nonallelic recombinations between the iduronate-sulfatase gene and pseudogene cause various intragenic deletions and inversions in patients with mucopolysaccharidosis type II", Eur. J. Hum. Genet., v. 6, pp. 492-500.
Hahnen, E., et al., (1996), "Hybrid survival motor neuron genes in patients with autosomal recessive spinal muscular atrophy: new insights into molecular mechanisms responsible for the disease", Am. J. Hum. Genet., v. 59, pp. 1057-1065.
Campbell, L., et al., (1997), "Genomic variation and gene conversion in spinal muscular atrophy: Implications for disease process and clinical phenotype", Am. J. Hum. Genet., v. 61, pp. 40-50.

(Continued)

Primary Examiner—Kenneth R. Horlick
Assistant Examiner—David C Thomas
(74) Attorney, Agent, or Firm—Lewis Kohn & Fitzwilliam LLP; David M. Kohn

(57) ABSTRACT

The SBDS gene has been identified as the site of mutations associated with SDS. Methods are provided for determining whether a subject is suffering from SDS.

11 Claims, 21 Drawing Sheets
(1 of 21 Drawing Sheet(s) Filed in Color)

OTHER PUBLICATIONS

Wirth, B., et al., (1997), "De novo rearrangements found in 2% of index patients with spinal muscular atrophy: Mutational mechanisms, parental origin, mutation rate, and implications for genetic counseling", Am. J. Hum. Genet., v. 61, pp. 1102-1111.

Zhu, H., et al., (2001), "Global analysis of protein activities using proteome chips", Science., v. 293, pp. 2101-2105.

Bateman, A., et al., (2002), "The Pfam Protein Families Database", Nucl. Acids Res. 30(1):276-280.

Winzeler, E. A., et al., (1999), "Functional characterization of the S. cerevisiae genome by gene deletion and parallel analysis", Science., v. 285, pp. 901-906.

Wu, L. F. et al., (2002), "Large-scale prediction of Saccharomyces cerevisiae gene function using overlapping transcriptional clusters", Nat. Genet., v. 31, pp. 255-265.

Miller, S.A., Dykes, D.D., & Polesky, H.F. (1988), "A simple salting out procedure for extracting DNA from human nucleated cells", Nucleic Acids Res. v. 16, 1215.

MacDonald, R.J., et al., (1987) "Isolation of RNA using guanidinium salts", Meth. Enzymol. 152, 219-234.

Benson, D.A., et al., (2002), GenBank. Nucleic Acids Res. v. 30, 17-20.

Hubbard, T., et al., (2002), "The Ensembl genome database project", Nucleic Acids Res. 30, 38-41.

Schwartz, S., et al. (2000), "PipMaker—A Web Server for Aligning Two Genomic DNA Sequences", Genome Res. v. 10, 577-586.

Rozen, S. and Skaletsky, H.J., (2000), "Primer3 on the WWW for general users and for biologist programmers", In: Krawetz, S., and S. Misener. Bioinformatics Methods and Protocols: Methods in Molecular Biology, Humana Press, Totowa, NJ.

Isogai, T., et al. (2000), "NEDO human cDNA sequencing project", Genbank Accession No. AK001779, Abstract XP002268960.

Popovic, M., et al., (2000), "Refined mapping of the Shwachman-Diamond syndrome locus at 7p12-q11" Amer. J. Human Genetics v. 67, pp. 321: XP002268959: Abstract.

Boocock, G., et al., (2003), "Mutations in SBDS are associated with Shwachman-Diamond syndrome" Nature Genetics, v. 33, pp. 97-101.

Prades, C., et al., (2002), "The human ATP binding cassette gene ABCA13, located on chromosome 7P12.3, encodes a 5058 amino acid protein with an extracellular domain encoded in part by a 4.8-kb conserved exon", Cytogenetic and Genome Research v. 98(2-3):160-168.

Smith, A., et al., (2002), "Intermittent 20q-and consistent i(7q) in a patient with Shwachman-Diamond syndrome," Pediatr. Hematol. Oncol. v. 19(7):525-528.

Elghetany, M.T. and Alter, B.P., (2002) "p53 Protein Overexpression in Bone Marrow biopsies of patients with Shwachman-Diamond syndrome has a prevalence similar to that of patients with refractory anemia", Arch. Pathol. Lab. Med. v. 126(4):452-455.

Jelic, T.M, et al., (2001) "Expression of CD5 on Hematogones in a 7-year-old girl with Shwachman-Diamond Syndrome", Pediatr. Develop. Pathol. v. 4(5):505-511.

Spirito, F.R., et al., (2000) Cytogenetic characterization of acute myeloid leukemia in Shwachman's syndrome, A case report, Haematologica v. 85(11):1207-1210.

Dale, D.C., et al., (2000) "Mutations in the gene encoding neutrophil elastase in congenital and cyclic neutropenia", Blood, v. 96(7):2317-2322.

Sokolic, R.A., et al., (1999) "Discordant detection of monosomy 7 by GTG-banding and FISH in a patient with Shwachman-Diamond syndrome without evidence of myelodysplastic syndrome or acute myelogenous leukemia", Cancer Genetics & Cytogenetics., 115(2):106-13.

J. T. den Dunnen, "Nomenclature for the description of human sequence variations," Hum. Genet (2001) 109:121-124.

* cited by examiner

```
                                                                    E44G                                   I87S
              N8K                         N34fs15 S41fs15|         K62X K67E                             84Cfs3
         Ath  MSKTLVQPVGQKRLTNVAVVRLKKQGNRFEIACYKNKVLSWRSGV-EKDIDEVLQSHTVYSNVSKGVLAKSKDLMKSFGSDDHTKICIDI
         Dme  MSK-IFTPTNQIRLTNVAIVRLKKGGKRFEIACYKNKVLSWRSNS-EKDIDEVLQTHTVFTNVSKGQAAKKDELQKAFNKTDETEICKEI
         Cel  MSKNIKTPTNQKVLTNVAVVRMKKTGKRFEIACYKNKVVHWRNKS-EKDIDEVLQTHTVFSNVSKGQLSKKEELIAAFGIEDQLEICKII
         Mmu  MS--IFTPTNQIRLTNVAVVRKRGGKRFEIACYKNKVVGWRSGV-EKDLDEVLQTHSVFVNVSKGQVAKKEDLISAFGTDDQTEICKQI
SEQ ID   Hsa  MS--IFTPTQIRLTNVAVVRMKRAGKRFEIACYKNKVVGWRSGV-EKDLDEVLQTHSVFVNVSKGQVFKEDLISAFGTDDQTEICKQI
NO: 2    Ola  MS--IFTPTNQIRLTNVAVVRMKKGGKRFEIACYKNKVMSNRTGA-EKDLDEVLQTPSVFINVSKGQTAKKDDLLKAFGTEDQTEICKQI
         Sce  MP--INQPSGGQIKLTNVSLVRLKKARKRFEVACYQNKVQDYRKGI-EKDLDEVLQIHQVFMNVSKGLVANKEDLQKCFGTTNVDDVIEEI
         Ecu              MFTPLNQKKLVNVSIVTLKKFGRRYELAVYPNKLYEYRNGM-RTPLSEILQTDTIYRSVSKGEIARQGDLDLFCRT--HEEIVREI
         Mac        MVSLDEAVTARLKRGSKHFEVLEPEGALAYKRGE-EVNLEDILAVETIFEDANRGDRAAESDILNSFETTDPFEIAAVI
         Hnr        MISLDDAVTARLETHGERFEVLVDPDDAALEMRRDEFDGELTDVIAARDVFENASRGDRPAESDLETVFGTTEPLEIIPEV
         Mth        MVSLEDAVIARLESHGERFEVLVDPDLAAEFRREDSDVSVEDVLAVQEVFRDARKGDKASEEAMRKVFETADPLEVTPVI
         Mka        MARVSLEDAVVARLEKGGERFEVLVDPEGARKFREGE-DVDVEEILAVEQVFRDARKGERASEQAMEELFGTSDDPIKVAEIV
         Mja        MGRDIMVSLEEAVIARYTSHGEKFEILVDPYLAAKLKEGQ-NVDFDELLAIEVVFRDASKGEKAPEELLSKIFGTTDVKEIAKKI
         Afu        MVSLDKAVIARLRKGGEEFEVLVDPYLARDLKEGK-EVNFEDLLAAEEVFKDAKKGERASVDELRKIFGTDDVFEIARKI
         Pab        MPISVDKAVIARLKVHGETFEILLVDPYLARDFKEGK-EVPIEEILATPYVFKDAHKGDKASEKEMEKIFGTSDPYEVAKII
         Tac        MVKVEDAIVARLESHGYHFEILVDPDAIERIRKGN--IDIENDLAFPEVVKDVRKGEKASDDSLKEAFKTTVIAQVAIEI
         Pae        MTKKVAVAKLDKGGEHFEILDPDAALELKMGK--PLGIDKVLVHEEIYKDAKKGLRASEQALKKVFGTTDVRKIAEII
         Sso        MTKERDYVIVKYESHGERFEILAKPKEALAFRSGK--SISLSDVVVSDTIYKDVKKGKPNKSTRQGKASPASLKKVFGTTDFETIVKEI
         Ape        MAWMEVRGKRFEILVRPELAFRYKEKG-DVDLEDVLTDTIYRDVRKGKLKASPEEVKKAFGTSDPRRVAEKI
                              :*:     .      ..    ::...:*    .  :        :

D97_K98delinsEVQVS            R126T                                      R169C
         Ath  LEKGELQVAGKERESQFSSQFRDIATIVMQKTINPETQ-RPYTISMVERLMHEIHFAVDPHSNSKKQALDVIRELQKH--EPIKRSPMRL
         Dme  LSKGELQVSEKERQSCLDTQLNSIVNSVAALCVNPETR-RPYPASIIEKSLKDAHFSVKMNRNTKQNTLEAIKILKDH--MPIERSRMKL
         Cel  LDKGDLQVSEKERQAASDQSLKEVSQLIASMVVNPETK-RPVPPSVIDKALQEMHFSLKPNRSSKQQALDAIPKLRET--LKIERAKMKI
         Mmu  LTKGEVQVSDKERHTQLEQMFRDIATIVADKCVNPETK-RPYTVILIERAMKDIHYSVKPNKSTKQQALEVIKQLKEK--MKIERAHMRL
         Hsa  LTKGEVQVSDKERHTQLEQMFRDIATIVADKCVNPETK-EPYTVILIERAMKDIHYSVKTNKSTKQQALEVIKQLKEK--MKIERAHMRL
         Ola  LAKGELQVSDKERQTQLETMFRDIATTVADKCVNPETK-RPYEVSMIERAMKDIHYSVKPNKSTKQQALEVIRQLKET--MEIQRAHMRL
         Sce  MHKGEIQLSEKERQLMLNKVNNEMLTIVSAKCINPVSK-KRYPPTMIHKALQELRFSPVINKPAKLQALEAIKLLVSKQII PIVRAKMKV
         Ecu  LDCGYEQKSEATRV-EQEKTEREIVQILRNKVTRGGGRH---LSEASLREAIGKVHN--IYVGNSKKQSQEILSKLEKMG-----FDRVGV
         Mac  LKSGELQLTAEQRKRMLEEKKKKVIYTISRNAINPQTR-APHPPARIERAMEEAKVHIDPLKSVDQLVTITHMKAIRPL--IPIRFEEINI
         Hnr  IGQGEIQITADQREAHQQRKKRSLINTISRNAINPQMDGAPHPPDRIESALDEAGFTVDPMTPADEGVDDALEALRPV--IPIRFEEMTV
         Mka  IKEGEIQLTAEQRRRMQEEVKRKIIHIIARRAVDPRTG-APHPPERIERAMEEAGVHIDFMKSAEEQVKDVIKQLRPV--LPMKFEEVKV
         Mja  ILKGQVQLTAKQREEIREQKKRQIITIISRNTINPQTD-TPHPPHRIEKAMEELRIMIDIYKSAEEQVPEIVKKLKKV--LPIREFEKRDI
         Afu  ILEGEVQITAEQREMLEAKRKQIINFISRNTIDPRTN-APHPPSRIERALEEAKVHIDIFKSVEAQVKDIVKALKPI--LPLKFEEMEI
         Pab  LRKGEVQLTAQQRREMLEEKKRQIATIIHRHAVDPRTG-YPHPVDRILRAMEEVGVRVDIFKDAEAQVQDVIKAIRRI--LPLRIEMKVI
         Tac  VKKGQIQLTTEQRREMYDERRKQIVNLIAREGINPQTN-TPHTPYRLSQAMDEAKVKIDPLKPAEDQVQNVLKAIMPI--IPIRLEKAKI
         Pae  IKEGEIPLTAEQRRKLIEDKKRQIVEWISRNCIDVRTK-TPVPPQRVENALEQARVSIDPFKSVEEQVQEVLKEIQRI--IPIKVATARV
         Sso  LLKGELPVTAEQRKEMLETKRKQIIDFIHRNAVDPKTN-LPIPPTRLEMAMEQARIQIDLNKDVEAQAMQIVKEISKI--IPIKIARALL
         Ape  LKEGEIQLTEEQRRRLLEAKRRQIISYIARNAIDPTTG-RPIPEARIEAALEEVRFPINLWRDAESQAVEAVRLIARV--MPIRLARALL
                                :    *     .        .:        .         .                    :

I212T
         Ath  RLTVPVQNFP-SLLEKLKENDGSVVSKDES--GTQMSTVCEMEPGLFRECDSHVRSIQ---GRLEILAVSVHAEGDTSMDHYDEHDDMAL
         Gar+ RLIVPGQNFH-SLCEKLNEWGATIVSKDES--GTQLSVICEIEPGLFRECDSLVRNLQ---GRLEILSVSVHAEGDTQVDNYDD-EDISS
         Pba+ GLTVSGQNFS-TLLEKLGAHDANVVSKDES--GSRQSIICEMDPGFFRDCDALVRNLQ---GRLEILAVSVHFEEDTHVDDYDDYEDVAS
         Dme  RVSFAGKEGGGKLKESVVKLANAVEHEEWD--EATLHLTLLIDPGQYRVIDELVRNETKGKGLLELLELKEVVESEELF
         Cel  RVAIPTKEAK-SVHTKLKTLFSDVEVDDWQ---DGSLEMVGLIEPGSFRALDDLVRAMETKGHGRLEILSLKDVVEGELQIS
         Mmu  RFILPVNEGK-KLKEKLKPLMKVVESEDYS--QQ-LEIVCLIDPGCFREIDELIKKETKGRGSLEVLSLKDVEEGDEKFE
         Hsa  RFILPVNEGK-KLKEKLKPLIKVIESEDYG--QQ-LEIVCLEDPGCFREIDELIKKRTKGKGSLEVLNLKDVEEGDEKFE
         Ola  RLQLPAKEAK-RLKEKLKPLLQVVESEEFD--EE-LEMICLVDPGCFREIDELIRCETKGRGSLEVLSLKDVEEGEEKM
         Sce  KVAISEPSRQPELIEKISKLIASSPGESTKPELDPWTCTGLIDPVNYRDLMTLCDK--KG--TVQVLDMAVIDNTTHN
         Ecu  RVSVEMS-----DKVAEFVKQNGEIHDG----------YVMIRSDCFPRFKDMCEKEKVR--YLILRREEPEDEEIC
         Mac  AVKIPPEYAP-KAYGDISKV-GTITKEENQG-DGSWIAVVRIPAGVQTDFYALINHLTKGEAQTKLL
         Hnr  AVQLPADYAG-SGQAKLREF-GELEREENQA-DGSWVGVITFPAGMQDEFYGRVNEVSEGNGEFSVVKDKDELKTR
         Mka  AIRIPAKYTG-QAMGVVREF-GDIEREENQY-DGAWVAVVRLPAGLQDEFFEKLNEITKGDFESKILE-RESVEGP
         Mja  AVKIPAEFAS-KAYNALYQF-GAVKQEENQP-DGSLIVLIEIPSGIEAEFYAHLNKITKGNVQTKVVKKYSE
         Afu  AIKIPPEHTG-RAISALYNF-GGVTREEWQR-DGSWICVHRIPSGMYGDLMDLLGKVAKGEALTKVLRRIG
         Pab  AVKTPSEYVG-RAYGEVRKF-GRIKKEEWAS-DGSWILFLIEIPGGVEEEFYEKLNALTKGNAQTKLIERKGL
         Tac  AVKLIGDAYG-KLYGELAKS-GYM-KEEWGK-DGSWMGILEVPAGIQGDIIENLSRRGGDKVQIKILKQ
         Pae  ALAVSSTYAQ-RVKGLVAKM-AKIVNERYKS-DGSWEALLELPAGLQDVLIARVNDVTHGDADIRILEIVY
         Sso  SIKVPSEYSS-KVKSQLHNL-GEVKKANHLE-DGTLLAELEIPAGAQQOVIDKLNSLTKGEVEVKVLQVR
         Ape  EVKIPPPHSG-RAYQALMRM-GEVKKADWLP-DGSLKAELEIPAGAQVEVTSRIQALARGRAAEVKVKKVA

U1-like zinc finger
         Ath  QTHKPLLPAETET----KDLTDPVVELSKKLQKQEISTTDNIKQEGGEEKKGTKCSTCNTFVGEAKQYREHCKSDWHKHNLKRKTRKLPPIS
         Gar+ QLPKDSAESASSSRLPPESSDSDSVIQLSEKIQKHTIY--SGNGNAEGEAKQ-NKCSTCNAFVGDSKQYRDHFRSEWHKHNLKRKTRQLPPLT
         Pba+ ALPK-----------ESTDSAVQLSEKIQKQTLS--DEK-KAGAEVKQ-NKCSTCNVSVGDAKQF Ath  ADECMSEIDMDDSRADLKDYSF
         Gar+ AEECLADVELSDSKTDLQDYSF
```

Fig. 4

SBDS cDNA Sequence ID NO:1

```
 -184 gtaagtaagc ctgccagaca cactgtgacg gctgcctgaa gctagtgagt cgcggcgccg
 -124 cgcactggtg gttgggtcag tgccgcgcgc cgatcggtcg ttaccgcgag gcgctggtgg
  -64 ccttcaggct ggacggcgcg ggtcagccct ggttcgccgg cttctgggtc tttgaacagc
   -4 cgcgATGTCG ATCTTCACCC CCACCAACCA GATCCGCCTA ACCAATGTGG CCGTGGTACG
  +57 GATGAAGCGT GCCGGGAAGC GCTTCGAAAT CGCCTGCTAC AAAAACAAGG TCGTCGGCTG
 +117 GCGGAGCGGC GTGGAAAAAG ACCTCGATGA AGTTCTGCAG ACCCACTCAG TGTTTGTAAA
 +177 TGTTTCTAAA GGTCAGGTTG CCAAAAAGGA AGATCTCATC AGTGCGTTTG GAACAGATGA
 +237 CCAAACTGAA ATCTGTAAGC AGATTTTGAC TAAAGGAGAA GTTCAAGTAT CAGATAAAGA
 +297 AAGACACACA CAACTGGAGC AGATGTTTAG GGACATTGCA ACTATTGTGG CAGACAAATG
 +357 TGTGAATCCT GAAACAAAGA GACCATACAC CGTGATCCTT ATTGAGAGAG CCATGAAGGA
 +417 CATCCACTAT TCGGTGAAAA CCAACAAGAG TACAAAACAG CAGGCTTTGG AAGTGATAAA
 +477 GCAGTTAAAA GAGAAAATGA AGATAGAACG TGCTCACATG AGGCTTCGGT TCATCCTTCC
 +537 AGTCAATGAA GGCAAGAAGC TGAAAGAAAA GCTCAAGCCA CTGATCAAGG TCATAGAAAG
 +597 TGAAGATTAT GGCCAACAGT TAGAAATCGT ATGTCTGATT GACCCGGGCT GCTTCCGAGA
 +657 AATTGATGAG CTAATAAAAA AGGAAACTAA AGGCAAAGGT TCTTTGGAAG TACTCAATCT
 +717 GAAAGATGTA GAAGAAGGAG ATGAGAAATT TGAAtgacac ccatcaatct cttcacctct
 +777 aaaacactaa agtgtttccg tttccgacgg cactgtttca tgtctgtggt ctgccaaata
 +837 cttgcttaaa ctatttgaca ttttctactt tgtgttaaca gtggacacag caaggctttc
 +897 ctacataagt ataataatgt gggaatgatt tggttttaat tataaactgg ggtctaaatc
 +957 ctaaagcaaa attgaaactc caagatgcaa agtccagagt ggcatttgtc tactctgtct
+1017 catgccttga tagcttttcca aaatgaaagt tacttgaggc agctcttgtg ggtgaaaagt
+1077 tatttgtaca gtagagtaag attattaggg gtatgtctat acaacaaaag gggggtctt
+1137 tcctaaaaaa gaaaacatat gatgcttcat ttctacttaa tggaacttgt gttctgaggg
+1197 tcattatggt atcgtaatgt aaagcttgga tgatgttcct gattatctga gaaacagata
+1257 tagaaaaatt gtgccggact tacctttcat tgaacatgct gccataactt agattattct
+1317 tggttaaaaa ataaaagtca cttatttcta attcttaaag tttataatat atattaatat
+1397 agctaaaatt gtatgtaatc aataaaacca ctcttatgtt tatt
```

SBDS Amino Acid Sequence ID NO:2

```
  1 MSIFTPTNQI RLTNVAVVRM KRAGKRFEIA CYKNKVVGWR SGVEKDLDEV LQTHSVFVNV
 61 SKGQVAKKED LISAFGTDDQ TEICKQILTK GEVQVSDKER HTQLEQMFRD IATIVADKCV
121 NPETKRPYTV ILIERAMKDI HYSVKTNKST KQQALEVIKQ LKEKMKIERA HMRLRFILPV
181 NEGKKLKEKL KPLIKVIESE DYGQQLEIVC LIDPGCFREI DELIKKETKG KGSLEVLNLK
241 DVEEGDEKFE
```

FIGURE 5

SBDS Exon 1: (SEQ ID NO: 35)

```
                                        Primer A (SDCR9x1BF) →
SBDS                                    gcgtaaaaagccacaatacgcaggcgt
                                        ||| ||||||||||||| |||||||||
SBDSP                                   gcggtaaaagccacaatgcgcaggcgt
                                         |   |   |         |  |||

MUSBDS                                  aacgacccgccttcctttgaggtgcct

Primer Q (RTSDCR91F)
→
                                                       -184
                                                        |
SBDS       catcgctcacttttcccctcccggcttctgctccacctgacgcctgcgcagtaagtaagc
           |||||||||||| |||||||||||||||||||||||||||||||||||||||| ||||||
SBDSP      catcgctcacttctcccctcccggcttctgctccacctgacgcctgcgcagtaagtaagc
              |      |  |   |   |  |   |   |    |   |   |    |  |  ||
MUSBDS     gggtggaactagagggcgtaaaaagtcacggcgcgcaggcgtggttgctttcttatcggc SBDS       ctgccagacacactgtgacggctgcctgaagctagtgagtcgcggcgccgcgcactggtg
           ||||||||||| |||||  ||||||||||||||||||||||||||||||||||||| |||
SBDSP      ctgccagacacgctgtggcggctgcctgaagctagtgagtcgcggcgccgcgcacttgtg
           ||    |    ||  |   |||   |   |   |   |  |  |  |   ||      |
MUSBDS     ctagtgcgccacttgacgcatgtgcagtagggcaatcgggcgtgcggtagcttcttccct SBDS       gttgggtcagtgccgcgcgccgatcggtcgttaccgcgaggcgctggtggccttcaggct
           |||||||||||||||||||||||| ||||||||||||||||||||||||||||||||||
SBDSP      gttgggtcagtgccgcgcgccgctcggtcgttaccgcgaggcgctggtggccttcaggct
           |  ||||    |  ||  |  |      |   |||    |||    |  |||     ||
MUSBDS     ggtaggttccggaagagccgcgcactccttgggcgttaagggttcgcgcgccgcagggtc 1
                                                             |
                                                             M  S
SBDS       ggacggcgcgggtcagccctggttcgccggcttctgggtctttgaacagccgcgATGTCG
           ||||||||||||||||||||||| ||||||||||||||||||||||||||||||||||||
SBDSP      ggacggcgcgggtcagccctggtttgccggcttctgggtctttgaacagccgcgatgtcg
           |    ||| |    |   |   ||   |  | | ||| ||||||||| |||||||
MUSBDS     gtttcagccgagcacttggcgtcccctcgagctcgagatctgtgaacagccaccATGTCG
                                                                 M  S
```

Fig. 6

```
              I  F  T  P  T  N  Q  I  R  L  T  N  V  A  V  V  R  M  K  R
SBDS    ATCTTCACCCCCACCAACCAGATCCGCCTAACCAATGTGGCCGTGGTACGGATGAAGCGT
        ||||||||||||||||||||||||||||||||||||||||||||||||||||||||||||
SBDSP   atcttcacccccaccaaccagatccgcctaaccaatgtggccgtggtacggatgaagcgc
        |||||||||||||||||||||||||| || ||||||||||||||||||| ||||||||||
MUSBDS  ATCTTCACCCCCACCAACCAGATCCGACTGACCAATGTGGCCGTGGTGCGGATGAAGCGG
              I  F  T  P  T  N  Q  I  R  L  T  N  V  A  V  V  R  M  K  R A  G  K  R  F  E  I  A  C  Y  K  N  K  V  V  G  W  R  S  G
SBDS    GCCGGGAAGCGCTTCGAAATCGCCTGCTACAAAAACAAGGTCGTCGGCTGGCGGAGCGGC
        |||  |||||||||||||||||||||||||   ||||||||||||||||||||||||||
SBDSP   gccaggaagcgcttcgaaatcgcctgctacagaaacaaggtcgtcggctggcggagcggc
        |  |||||||||||||||||||||||||||  ||||||||||||||||||||||||| ||
MUSBDS  GGAGGGAAGCGCTTCGAAATCGCCTGCTATAAAAACAAGGTCGTCGGCTGGCGGAGTGGC
              G  G  K  R  F  E  I  A  C  Y  K  N  K  V  V  G  W  R  S  G 128
         |
SBDS    GTgtgagtagccccctccctcgggcctgggcctgggcctgagccgtcacctccgaggcgg
        ||||||||||||||||||||||||||||||||||||||||||||||||||||||||||||
SBDSP   ttgtgagtagccccctccctcgggcctgggcctgggcctgagccgtcacctccgaggcgg
        ||||||||  ||  |||  ||   ||       |  |  |      |    |   |   |
MUSBDS  GTgtgagtaatcctgtgcccagagttcggcggcctggcctccctaaccccggctcctgcg SBDS    cctgtctctgcccaagtcgagtgaatgggccaggctggggtgtt----ggccggggagga
        ||||||||||||||||||||||||||||||||||||||||||||    |||| ||||||
SBDSP   cctgtctctgcccaagtcgagtgaatgggccaggctggggtgtttgttggcccgggagga
        |        ||    |   |  ||   |||  |||       ||      ||  ||
MUSBDS  acccatcggtacctttcaggcctggtttacccgattcggattgggttctgctttgggatt SBDS    aatggaacattcctgctgtgagcatgagacgtcgctgtccgagcttggcgcctaagccaa
        ||||||||||||||||||||||||||||||||||||||||||||||||||||||||||||
SBDSP   aatggaacattcctgctgtgagcatgagacgtcgctgtccgagcttggcgcctaagccaa
        |  ||      |  ||        ||    ||    ||    ||    |        |
MUSBDS  ttgttagtatcataaaaactgccaactacaaacgccatcagagccgggtgggaccgatgg ← SDCR9x1seqRev
SBDS    gggtttcttctttatttggttggttcggattgggttgttggtttggggttttgttttgtt
        |||||||||   |||||||||||||||||||||||||||||||||||||||||||||||
SBDSP   gggtttctt---tatttggttggttccgattgggttgttggtttggggttttgttttgtt
        ||||  |    |    |    |    |        |    |    |    ||   |||
```

Fig. 6 (cont.)

```
MUSBDS   tttaggcctgtaatcccagcgcccaggaaactgaggcaggaggattgctgcgatttccag

SBDS     ggtgtcataaaagctgcagccaagaaatctcgtaattgtggtccttttcctagaataatg
         ||||||||||||||||||||||||||||||||| ||||||||||||||||||||||||||
SBDSP    ggtgtcataaaagctgcagccaagaaatctcataattgtggtccttttcctagaataatg
         |   |  || ||     |    |    |||  ||||    |          | |    ||
MUSBDS   gccagcctggaacgtgtgtgtgtgtatgtgtatgtgtgtgttgtgtgtgtatgtgt ← Primer B (SDCR9x1BR)
SBDS     atggctgagaacctagtcttacgaatactgtcatag
         ||||||||||||| ||||| ||| |||||||||||||
SBDSP    atggctgagaacctagtgttccgaatactgtcatag
         |||  || |                 |       |
MUSBDS   atgtgtgtgtgagagagaccgtgaccgaccctgtac SBDS Exon 2: (SEQ ID NO: 36)

Primer E (SDCR9x2BF)→
SBDS     aaatggtaaggcaaatacggttctgagttttgaaaatgttccctcaggccgatgcgggca
         |||||||  ||||||||| || |||||||||||||||||||||||||||||||||||||
SBDSP    aaatggtagggcaaatacagttctgagttttgaaaatgttccctcaggccgatgcggca
          |  |       |      |||  |   ||  |                     | |
MUSBDS   gtagtgtcttcgctactgccatctagggacagatattccaggacagaagaaacaccactc SBDS     gttcacttgaggccaggagttcgaggccagcctggccaacatgaaacccatctctacta
         | ||||||||||||||||||||||||||||||||||||||||||||| |||||||||||
SBDSP    gatcacttgaggccaggagttcgaggccagcctggccaacatgaaacaccatctctacta
           |          ||   |     |      |         |    |||         |
MUSBDS   cccaccacaccctgagttttccttacataaaacaatgatgtagttttttccctctgtggtga SBDS     aaaatacaaagttagccgggtgtggtggcgcatgcctgtaatcccagttactcaggaggc
         |||||||||| || ||||||||||||||||||||||||||||||||||| |||||||||
SBDSP    aaaatacaaaattagccgggtgtggtggcgcatgcctgtaatcccagctactcaggaggc
         |        ||  ||          |||    |   |    |               | |
MUSBDS   agtgggagaatccagatactgtccttcgcaggtagccaccagagagagagtgtggtgtgt SBDS     tgaggcgggagaatcacttgaacccgggaggctgaggttacagtgacccgagatcgcgcc
         ||||| |||||||||||||||||||||||||| || ||| ||||| |||||||||||||
SBDSP    tgaggcaggagaatcacttgaacccgggaggcggacgttgcagtgagccgagatcgcgcc
          | ||||| |    |           |||| |  ||    |
MUSBDS   gtgtgtgtgagatttctctttttttttttctttagggttttttgttttgtttttttttgtt
```

Fig. 6 (cont.)

```
SBDS    attgcactccagcctgggcaaaaacagtgaaattccatctaggggcggggggttgggggggt
        ||||||||||||||||||||||||||||||||||||||||||||| ||||||   ||||||
SBDSP   attgcactccagcctgggcaaaaacagtgaaattccatctaagggcggg----gggggg-
         |              |||  |      |||  |        |  |         |
MUSBDS  ttgtttggtttttttttttttttttttgagactggcctcaaactcccaatttccctgcc
```

Primer C (SDCR9/SDCR9Lx2)→

```
SBDS    aagaaaaagaaaactgccctctacactaaaggtcatcagggggatttgttgtgtcttgcc
        ||||||||||||||||||||||||||||||||||||||||||||||||||||||||||
SBDSP   ------aagaaaactgccctctacactaaaggtcatcagggggatttgttgtgtcttgcc MUSBDS  tctgcctcctaaatggtgagttacagatgtgcacatcacacccagcttgcagcacttgcc
```

Primer 0 (SDCR9/SDCR9Lx2-3F)→

```
SBDS    gttcatgttgttgccatctcgtatttaaatgtaaatgcatgtccaagtttcaagtatatt
        |||||||||||||||||||||||||||||||||||||||||||||||||||||||||||
SBDSP   gttcatgttgttgccatctcgtatttaaatgtaaatgcatgtccaagtttcaagtatatt
         ||  |||||| |||| || |||||||||| | || || | |                |
MUSBDS  atttctcttgttgctatcttgtgtttaaatgtgagtggatttcttactatccagtggat
```

```
                              129
                               |
                          V  E  K  D  L  D  E  V  L  Q
SBDS    cacataggactttctctcctgccctcacaagGGAAAAAGACCTCGATGAAGTTCTGCAGA
        |||||||||||||||||||||||||||||||          |||||||||||||||||||
SBDSP   cacataggactttctctcctgccctcacaagggaaaaagaccttgatgaagttctgcaga
        |||||||||||||||||||||||||||||  |||||||||||| ||||||||||||||||
MUSBDS  cacataggactttctctcctgccctttcaagGGAAAAAGACCTTGATGAAGTTCTGCAGA
                                       ─────────────────────────────
                                      V  E  K  D  L  D  E  V  L  Q
```

```
         T  H  S  V  F  V  N  V  S  K  G  Q  V  A  K  K  E  D  L  I
SBDS    CCCACTCAGTGTTTGTAAATGTTTCTAAAGGTCAGGTTGCCAAAAAGGAAGATCTCATCA
        |||||||||||||||||||||||||| |||||||||||||||||   |||||||||||||
SBDSP   cccactcagtgtttgtaaatgtttcctaaggtcaggttgccaagaaggaagatctcatca
        |||| ||||||||||||||||||||| ||||||||||||||||||||||||| ||||||
MUSBDS  CCCATTCAGTGTTTGTAAATGTTTCCAAAGGTCAGGTTGCCAAGAAGGAAGACCTCATCA
        ────────────────────────────────────────────────────────────
         T  H  S  V  F  V  N  V  S  K  G  Q  V  A  K  K  E  D  L  I
```

```
                S  A  F  G  T  D  D  Q  T  E  I  C  K  Q
SBDS     GTGCGTTTGGAACAGATGACCAAACTGAAATCTGTAAGCAGgtgggtaacagctgcagca
         ||||||||||||||||||||||||||||||||||||||||| ||||||||||||||||||
SBDSP    gtgcgtttggaacagatgaccaaactgaaatctgtaagcaggcgggtaacagctgcagca
         ||||  ||||||  |||||  |||||  |||||||||||||  |||||   |  |   |||
MUSBDS   GTGCATTTGGGACAGACGACCAGACTGAAATCTGCAAGCAGgtaggtcctgccaggtgca
         ‾‾‾‾‾‾‾‾‾‾‾‾‾‾‾‾‾‾‾‾‾‾‾‾‾‾‾‾‾‾‾‾‾‾‾‾‾‾‾‾‾
         S  A  F  G  T  D  D  Q  T  E  I  C  K  Q SBDS     tagctaaccctaataaccatttataacgtatttgtagatatattaaacattaaaggctgt
         ||||||||||||||||||||||||||||||||||||||||||||||||||||||||||||
SBDSP    tagctaaccctaataaccatttataacgtatttgtagatatattaaacattaaaggctgt
         |      |     |||  ||       |  · |    |     |     |        |
MUSBDS   atgtaacaaaatctcacgatggtaggcaacatctggaccactgtgtttactgtttttctt ← Primer D (SDCR9/SDCR9Lx2R)
SBDS     ttttctggaggaaagactaaccaagcaataatgtgaactgcacagtgtcacttctaataa
         ||||||||||||||||||||||||||||||||||||||||||||||||| | ||||||||||||
SBDSP    ttttctggaggaaagactaaccaagcaataatgtgaactgcacaatatcacttctaataa
                |   |  ||     |         |        |    |         |||  |
MUSBDS   gatgagttttgttgttttagcatttgttgggtccctcccacctccagtttatattgttg ← Primer F (SDCR9x2BR)
SBDS     taaagaacttggt
         |||||||||||||
SBDSP    taaagaacttggt
              |     ||
MUSBDS   ggcaatttgggga···

SBDS Exon 3: (SEQ ID NO: 37)

Primer G (SDCR9x3BF) →                          SDCR9x3CF
         →
SBDS     gctcaaaccattacttacatattgatagctggagaggatgaaatttaattttctctccat·
         ||||||||||||||||||||||||| |||||||||||||||||||||||||||||||| |||
SBDSP    gctcaaaccattacttacatattaatagctggagaggatgaaatttaattttctccca-
         ||   |   |           |   |   |   |         |   |   |     |
MUSBDS   tgtaagctgctgctgggttaaggcagcacgtggttctgcgtgagcagctgcagtggacgc SBDS     ccagttactcatttttttatggttagttaataaatagtgtgtgatagagaaagatagtgat
         ||||||||||||| |||||||||||||||||||||||||||||||||||||||||||||||
SBDSP    ---gttactcatttttttgtcgttagttaataaatagtgtgtgatagagaaagatagtgat
```

Fig. 6 (cont.)

```
                 |  ||  |                       |   |                        ||
MUSBDS   cgcctcccttcctccccgctacctacctgtgcagtagagagatacccagaactgatgagg 259
                                             |
                                             I  L  T  K  G  E  V  Q  V  S  D
SBDS     ttcttaaatgtgttggcattttttagATTTTGACTAAAGGAGAAGTTCAAGTATCAGAT
         ||||||| |||||||||||||||||||||||||||||||||||||||||||||||| ||
SBDSP    ttcttaactgtgttggcattttttagattttgactaaaggagaagttcaagtatcagat
         ||     |||||  |  ||||||||||||||||||||||||||||||||||||| ||||||
MUSBDS   gctttctctatgttctgccatctttagATTTTGACTAAAGGAGAAGTTCAAGTGTCAGAT
                                             I  L  T  K  G  E  V  Q  V  S  D Primer T (RTSDCR93F) →
             K  E  R  H  T  Q  L  E  Q  M  F  R  D  I  A  T  I  V  A  D
SBDS     AAAGAAAGACACACACAACTGGAGCAGATGTTTAGGGACATTGCAACTATTGTGGCAGAC
         |||||     |||||||||||||||||||||||||||||||||| |||||||||||||||
SBDSP    aaaga----cacacacaactggagcagatgtttagggacattgcaattattgtggcagac
         ||||||  | |||||||| |||||||||||||||||||||| || || || |||||||||
MUSBDS   AAAGAACGGCACACACAGCTGGAGCAGATGTTTAGGGATATCGCCACCATTGTGGCAGAC
             K  E  R  H  T  Q  L  E  Q  M  F  R  D  I  A  T  I  V  A  D K  C  V  N  P  E  T  K  R  P  Y  T  V  I  L  I  E  R  A  M
SBDS     AAATGTGTGAATCCTGAAACAAAGAGACCATACACCGTGATCCTTATTGAGAGAGCCATG
         ||||||||||   |||||||||||||||||||||||||||||| |||||||||||||||
SBDSP    aaatgtgtgactcctgaaacaaagagaccatacaccgtgatccttattgagagagccatg
         ||  ||||||||  || |||||||||||||||||||||||  || |||||||||||||||
MUSBDS   AAGTGTGTGAACCCAGAAACAAAGAGACCTTACACCGTTATCCTCATCGAGAGAGCCATG
             K  C  V  N  P  E  T  K  R  P  Y  T  V  I  L  I  E  R  A  M 459
                      ← Primer S (RTSDCR93R)                       |
             K  D  I  H  Y  S  V  K  T  N  K  S  T  K  Q  Q
SBDS     AAGGACATCCACTATTCGGTGAAAACCAACAAGAGTACAAAACAGCAGgtgagtggtttc
         |||||||||||||||| |||||||||| |||||| ||||||||||||||||||||| ||
SBDSP    aaggacatccactatttggtgaaaaccaacaggagtacaaaacagcaggtgagtggtctc
         ||||||||||||||||  |||||||| ||||||||| ||||| || |||| || ||  ||
MUSBDS   AAGGACATCCACTACTCCGTGAAACCCAACAAGAGCACAAAGCAACAGgtaagggttcct
             K  D  I  H  Y  S  V  K  P  N  K  S  T  K  Q  Q ← Primer P (SDCR9/SDCR9Lx2-3R)
SBDS     tcatgtcatcaaaatatagccatggaaatcagttttctctgaagaaatcattaaaataat
         ||||||||||||||||||||||||||||||||||||||||||||||||||||||||||||
SBDSP    tcatgtcatcaaaatatagccatggaaatcagttttctctgaagaaatcattaaaataat
         |  ||||| |  |       |   |    |   |       ||  ||
```

Fig. 6 (cont.)

```
MUSBDS    tgttgtcctcgggacctaaggccatggaagtgcctgatgcgcctgcctccctatctctgg

SBDS      gggtctggggccaggcacaatggttcatgcctgtaatcctagcactttgggagccaagat
          |||||||||||||||||||||||||||| || ||||||||||||||||||||||||||||
SBDSP     gggtctggggccaggcacaatggttcataccgtaatcctagcactttgggagccaagat
          | |  ||    |||||   | ||  ||      |   ||   |    |    ||   |
MUSBDS    tgctggggtcagcagcacacacttccaggctgcctggctgtgctggtgctcatcattctg SBDS      gggaggattgcttgaggcctggaaacagcctgggaaacatagggacgccccatctctaaa
          ||||||||||||||||||||||||||||||||||||||||||||||||||||||||||||
SBDSP     gggaggattgcttgaggcctggaaacagcctgggaaacatagggacgccccatctctaaa
          | ||    ||   |||   |  | |||  |    |         |         |  | |
MUSBDS    agcagaccctctcccggctgagccataccc ttagctgctgctcctcagtgtgacggaaca SBDS      tttttttttttt-------tttttt----tgagacagagtcttactctattgcccaggctg
          |||||||| |||       ||||||    |||||||||||| ||| | ||||||||||||
SBDSP     tttttttgtttattgttgttttttttgtttgagacagagtcgcactgtgttgcccaggctg
          |            |        |     |   |   | ||       |             |
MUSBDS    caaatacacacagaactcttttt gtttgtttgtttgtttgggggttttttttttttttttt SBDS      gagtgcagtagtatgatctcggctcac-tacaatctccacctcccgcgttcaagcaagtc
          |||||||| | |  ||||||||||||| |||||||||||||||||||||||||||||||||
SBDSP     gagtgcagtggcacgatctcggctcacttacaatctccacctcccgcgttcaagcaagtc
          |   |  |||      |  ||    |||| |    |    |  |    |    |  | |
MUSBDS    ttagttttgttttggtctttcgagacagggtttctctgtattgccctggctgtcctgga SBDS      tcctgcctcagcctcctgagtagctgggattataggcacgtgccaccacactcagctaat
          ||||||||||||| |||||  ||||||||||||||||| ||||||||||  |||||||||
SBDSP     tcctgcctcagcctcccaagtagctgggattataggcacgcgccaccacacccagctaat
          |  ||        |   | ||   |   |      |      |    | |     |   |
MUSBDS    actcgctctgtagcccaggctggcctcgaactcagaaatccgcctgcctctgcctcccaa SBDS      tttg-tatttttagtagagttgaggtttcaccatgttggccaggctggtcttgaactcct
          ||||  ||||||||||||||||||||||||||| |||||||||||||||||||||||||
SBDSP     tttgttatttttagtagagttgaggttttaccatgttggccaggctggtcttgaactcct
          |  |    || ||    |       |||  | |  |   |          |       |
MUSBDS    gtgctgggattaaaggcgtgggccaccacacctggctcatacagaactcttatttcctgc SBDS      gaccctaggtgatccgtccgccttggcctcccaaagtgctgggattacaggcatcagcta
          ||||  |||||||||||||||||||||||||||||||||||||||||||||||||||||
SBDSP     gacctcaggtgatccgtccgccttggcctcccaaagtgctgggattacaggcatcagcta
```

Fig. 6 (cont.)

```
        ||    |       |   | ||          |   |   |
MUSBDS  ccagctcaaaccttttaaagagaaagcttggactttgagtcacctgagcccttttgctgtt SBDS    ccgtaccctacctctaaatttttttaatataaaaaattaaatttaaaaaaatgggtctgca
        ||||||||||||||||| |||||||||||||||||||||||||||++||||||||||| ||||
SBDSP   ccgtaccctacctctaatttttttaatataaaaaattaaatttaaaaaaatgggtttgca
          |   || | | |  |      ||  |  |   |  ||   |
MUSBDS  tgtgtttattaacatatttcctacagctcagccctgtcacgccagccattctgctggcct ← Primer H (SDCR9x3BR)
SBDS        tggaagcaagtg
            ||||||||||||
SBDSP       tggaagcaagtg
            |    ||||
MUSBDS      ggattccaagca SBDS Exon 4: (SEQ ID NO: 38)

Primer I (SDCR9x4CF) →
SBDS    aaagggtcattttaacacttcttttttgaattttttaatttatatataattcacataccat
        |||||||||||||||||||| ||||||||||||||| |||||| |||||||||||||| ||
SBDSP   aaagggtcattttaacacctcttttttgaattttttcaatttacatataattcacatacaat
         |    |    ||   | ||   |       |  |  | ||       |||        |
MUSBDS  ctcaaaagaaataacaagtcgggtgtggtggtgcacacctttaatcccagcactcgggag SBDS    aaatttcacactcataaagtatgtacactttaagtggtatattaacaaagttttggaacc
        ||||||||||||||||||| ||||||||||||+|||||||||||||||||||||  ||||||
SBDSP   aaatttcacactcataaagtgtgtacactttaagtggtatattaacaaagtttgggaacc
         |          |       ||         ||    |  |     |          ||
MUSBDS  gcagaggcaggcgaatttctgagttggaggccagcctgagttccaggacagccagggcta SBDS    ttccctgctacctggttcgagaacatttcatcaccacaaaaagaaagtcagtatccatt
        |||||||||||||||| |||||||||||||||||||||||||||||||||||||||||||
SBDSP   ttccctgctacctggtttgagaacatttcatcaccacaaaaagaaagtcagtatccatt
         |  |  |||  ||    ||| |   | | | |||||| |||   |   |    |
MUSBDS  tacagagaaaccctgtctcgaaaaaccaaaaaaaaaaaaaaaaaaaaaaaagaaggaag Fig. 6 (cont.)
```

```
SBDS    agtagccatccccccatttccccccacaggcccctcccaaccactaatctcctctcgtta
        ||.||| ||||||||||||||||||||||||| ||||||||||||||||||||||| ||||||
SBDSP   agtagctatccccatttccccccacaggcccttcccaaccactaatctcctgtcgtta
        |  |   |  |  ||  |            |       |||   |
MUSBDS  aaagaaagaaagcaagcaagcaagcaagcgagcaatggtgtttcacagcacgaagtatag SBDS    tggacttctcaattctggacatttcatataaatggaatcatacaatatgtggccttttca
        ||||||| |||||||||||||||||||||||||||||||||||||||| ||||||||||
SBDSP   tggacttgtcaattctggacatttcatataaatggaatcatacaatatatggccttttca
        |   |  |  ||   |   |   |       ||||||
MUSBDS  tatgacccatataactaacagcctgcctgagttattactgcttaggcagtggcctgactt SBDS    tggttcatacatgttgtaacctgcatcagcatgtcatttcttttttatgccggaataata
        |||||||||||||||||||||||||||||||||||||||||||||||||||||||||||
SBDSP   gggttcatacatgttgtaacctgcatcagcatgtcatttcttttttatgccggaataata
        |   |||||   |   |   | ||    |            | ||  |
MUSBDS  agacctgatcatgtacgtccagaaaaggcctggtggaaaactggaaggagccagagaaga SBDS    gcccactgtacggaaagaaacacattttgttcattcatctatcagttgatagacattggg
        |||||||||||||||| ||||| |||||||||||||||  ||||||||||||||||||||
SBDSP   gcccactgtacggaaaaaaacatattttgttcattcatttatcagttgatagacattggg
        ||  ||    |     |   | ||          |||
MUSBDS  acctccatacacaagaactctgggcaacctcagaactactcatgtccattccacaaccca SBDS    ttgctttcacttttgagctatgatgagcaatgctgctataaaatttcttgtatgtttctg
        ||||||||||||||||||||||||||||||||||||||||||||||||||||||||| ||
SBDSP   ttgctttcacttttgagctatgatgagcaatgctgctataaaatttcttgtatgttttg
        |     |   ||  |    ||     |   |        |
MUSBDS  accagggcttctctgtacagggaacaagcacaggagagtcatcaagggactaacgagct SBDS    tgtagacatatgttttcatttctgtatacctggtgactaccaaacctatttctaaaacag
        |||||||||| ||||||||||||||||||||| |||||||||||||||||||||||||
SBDSP   tgtagacatatattttcatttctgtatacctggggactaccaaacctattctaaaacag
        |  |   |  ||  ||     ||   |   |   |
MUSBDS  cacatcgaccacctgtgcactgttcccctctccataaacctcagattgcacaagctcagc SBDS    ctgcaccatttttactttaccaccatcagtgtttaagagttcagtttctccacatcctcag
        |||||||||||| |||||||| ||| |||||||||||||||||||||||||||||||||
SBDSP   ctgcaccatttttacattaccaccaacagcgtttaagagttcagtttctccacatcctcag
        | |  |  |   |||  |||||    ||   |  |    ||    |
```

Fig. 6 (cont.)

```
                                            SDCR9x4seqB →
SBDS    aattacaggcgtgagccaccacacctggccttcactttcttcatagttttttgaaacaca
        ||||  |||||||||||||||||||||||||||||||||||| ||||||||||||||||
SBDSP   gattagaggcgtgagccaccacacctggccttcactttcttcataatttttttgaaacaca
          |   |||                                  |||      ||
MUSBDS  ccactgaactgagtcccagcctttaacgttgctttctgccgaagcaaaaattattttttt SBDS    aaagcttttcttcttgataagtccaattttctatttttttttaacggtcacttatgtt
        |||||||||||||||||||||||||||||||||||||  |||||||||||||||||||
SBDSP   aaagcttttcttcttgataagtccaattttcta-tttttttttaacggtcacttatgtt
          |||        |  |  |  | ||    | |||        ||       |
MUSBDS  ttccatttcacaaaatgagacactagctcatttttaggtatttctaggattgctggtac SBDS    cttaatgttatacctaagaaaccattacctaatccaactacatggaaactactttgtttt
        ||||||||||||||||||||||||||||||||||||||||||||||||||||||||||||
SBDSP   cttaatgttatacctaagaaaccattacctaatccaactacatggaaactactttgtttt
         |||   || | ||        |  |            | ||   | | |      |
MUSBDS  cttggctgtaaaactgctggcataaggcagctatgtggaaactgctttgttcatgtctaa

460

SBDS    tgaaaaccttatgaaataatatagtagaagaaattgcattctcgattttgtcttggtagG
        ||||||||||||||||||||||||||||||||||||||||||||||||||||||||||||
SBDSP   tgaaaaccttatgaaataatatagtagaagaaattgcattctcgattttgtcttggtagg
          |  ||  |   |  |    ||  ||   |  ||     |      |  |       |||
MUSBDS  catataaatttgtgcagcacaaaaactaagtaacgagcacccccttgttctgtcttaaagG A  L  E  V  I  K  Q  L  K  E  K  M  K  I  E  R  A  H  M  R
SBDS    CTTTGGAAGTGATAAAGCAGTTAAAAGAGAAAATGAAGATAGAACGTGCTCACATGAGGC
        ||||||||||||||||||||||||||||| |||||||||  ||||||||  ||  ||||||  |
SBDSP   ctttggaagtgataaagcagttaaaagagaaaatgaagatagaacgtgctcacatgaggc
        ||||||||||||||||||||| | |||||||| |||||||||| || || ||||||| |
MUSBDS  CTTTGGAAGTGATAAAGCAGCTGAAAGAGAAGATGAAGATAGAGCGGGCCCACATGCGAT
        A  L  E  V  I  K  Q  L  E  K  M  K  I  E  R  A  H  M  R L  R  F  I  L  P  V  N  E  G  K  K  L  K  E  K  L  K  P  L
SBDS    TTCGGTTCATCCTTCCAGTCAATGAAGGCAAGAAGCTGAAAGAAAAGCTCAAGCCACTGA
        ||| |||||||||||||||| ||||||||||||||||||||||||||||||||||||||||
SBDSP   ttcagttcatccttccagtgaatgaaggcaagaagctgaaagaaaagctcaagccactga
        | || ||||||||| ||||| || ||||| ||||||||||| ||||| |||||||||||
MUSBDS  TGCGCTTCATCCTGCCAGTGAACGAAGGGAAGAAGCTGAAGGAGAAGCTGAAGCCACTGA
```

Fig. 6 (cont.)

```
MUSBDS   ccccgtctcctccacatccagctgccagtgactgacgctgcctgcgggtcagtggcagag

SBDS     taatacttgtcattgtctgccttttgatgatggccatcctggtggtatcttgtcgtggt
         ||||||||||||||||||| |||||||||||||||||||||||||||||||||||| ||
SBDSP    taatacttgtcattgtctgtcttttgatgatggccatcctggtggtatcttgtcgtcgt
           |   |  |  ||||     |  | |||     |   |        |  |  |   |
MUSBDS   gtgccaaggcaaaggcctgtgaggaccttactgtgtatcactaggcgtcccagcactctg SBDS     tttgatttgcatttccttaatgatgatttgagcatatttccatgtgcttattggtgcctc
         ||||||||||||||||||||| ||||||||||||||||||||||||||||||||||||||
SBDSP    tttgatttgcatttccttaataatgatttgagcatatttccatgtgcttattggtgcctc
           ||| |   |||    |      ||       |  |  | |       |  |   |||
MUSBDS   gatgactgttattagactttcagggaagccactagttcttctacccagtgacagcttctc SBDS     gtctgtcttcttttgagaaatctctgttcaggttctttgccc-----a----c-c-c---
         |||||||| ||||||||||||||||||||||||||||||||||         | | |
SBDSP    gtctgtctgcttttgagaaatctctgttcaggttctttgccccctttttattctcgctct
            |       | |                   |      | ||    |
MUSBDS   aggcacgggtgtccacagagtgggaagggccttgctggacggctggtgggaagctctggg SBDS     --c-ccc---c------gc-----c-c--tct----t-tttgcaaactctgcctcccgga
           | |||   |       ||     | |   |    | |||||||||||||||||||||
SBDSP    gtcacccagactagagtgcagtggcgcgatctcggctcattgcaaactctgcctcccgga
                    |  ||     |  ||    | |     ||     | |      |||
MUSBDS   ccatttcccaaggagcatgtctctgctctcaccactgttagaattactgtgaactcagc SBDS     ttcaagcaattctcctgcctcagcctcttgagtagctgggattacaggcgtgcactacca
         |||||||||||||||||||||||||||||||||||||||| |||||||||||| ||||||
SBDSP    ttcaagcaattctcctgcctcagcctcttgagtagctggtactacaggcgtgtgctacca
           |   ||   ||||   |   |      |    |  ||||   |  |       |
MUSBDS   tatgggctcaggtcctcaaggttcatggcttaaaacagggttggcttagaagtctccgag SBDS     cacccggctaattttctttttttgtattttagtggagacggggtttcaccatgttggc
         ||||||||||||||||||||||||||||||||| ||||||||||||||||||||||||
SBDSP    cacccggctaattttctttttttgtattttagtagagacggggtttcaccatgttggc
           |      ||    |||  |  | |    ||  |      |  |     |  ||
MUSBDS   gccaacaaaaagacattttgtctgttctagagatgtacgaaattcccaccgcacacattt SBDS     caggctggtctcgaattcctgaccttgtgatgcacccgcctcggcctcccaaagtgctgg
         |||||||||||||||||| |||||||||||||||||||||||||||||||||||||||||
SBDSP    caggctggtctcgaatttctgaccttgtgatgcacccgcctcggcctcccaaagtgctgg
           |    |  |  |  | | |  |    |   | ||     ||  |      |    |
MUSBDS   tcttgcttttagagagctgaggacagcccaggtcctcgtgcatgctgggtagttgcttca
```

624
                                                            |
                    I  K  V  I  E  S  E  D  Y  G  Q  Q  L  E  I
SBDS      TCAAGGTCATAGAAAGTGAAGATTATGGCCAACAGTTAGAAATCgtaagagtcaaatatt
          ||||||||||||||||| ||||||||| | |||| |||||||| |+|||||||||||||||
SBDSP     tcaaggtcatagaaagtaaagattatggccaacagttagaaatcgtaagagtcaaatatt
          | |||||  |  || |||||  || ||   ||| ||| |  ||  |||||||||      |
MUSBDS    TGAAGGTGGTGGAGAGTGAGGACTACAGCCAGCAGCTGGAGATCgtaagatgatggtggc
          ‾‾‾‾‾‾‾‾‾‾‾‾‾‾‾‾‾‾‾‾‾‾‾‾‾‾‾‾‾‾‾‾‾‾‾‾‾‾‾‾‾‾‾
           M  K  V  V  E  S  E  D  Y  S  Q  Q  L  E  I SBDS      ttctttgcttcatgttacctaaatattgtattctctagtaataaatttgtagcaaacatt
          ||||||||||||||||||||||||||||||||||||||||||||||||||||||||||||
SBDSP     ttctttgcttcatgttacctaaatattgtattctctagtaataaatttgtagcaaacatt
              | ||         |          |||      ||     |   ||
MUSBDS    ggggagcaggtggcgcagccaaggtcccatgattatgaccttaacacattattattcttg ← Primer J (SDCR9x4CR)
SBDS      tagatgttgtaaac-gtcagatattttc
          |||  |||||||||   |||||||||||
SBDSP     cagacattgtaaacagtcagatattttc
          ||  ||   |    ||         |||
MUSBDS    gcttccttctacccaaatagcctcgttc SBDS Exon 5: (SEQ ID NO: 39)

Primer K (SDCR9x5CF) →
SBDS      tccactgtagatgtgaactaactcatctgacactacttgaagttctaaaatctttgcaaa
          ||||||||||||||||||||||| |||||||||||||||||||||||||||||||||||
SBDSP     tccactgtagatgtgaactaacccatctgacactacttgaagttctaaaatctttgcaaa
                |       |  |       |    |   |||   |    |         ||
MUSBDS    gtatactgtggctgtcttcagacacagcagaaggcatcggatcccattacagatggttgt SBDS      actgtacacatgggccaggcacagtggctcgtgcctgtaatcccagcactttgggaggcc
          ||||||||| |||||||||||||||||||| |||||||||||||||||||||||||||||
SBDSP     actgtacacgtgggccaggcacagtggctcatacctgtaatcccagcactttgggaggcc
           || ||||       |    |||        |      |    |            |
MUSBDS    gagccacttgtggttgctgggaattgagctcagaacctctggaagagcagccagtgctga SBDS      aaggtgagcagataacatggtgaaaccctatctctactaaaaatacaaaaaataagccag
          |||  ||||||||||| |||||||||||||||||||||||||||||||||||||||||||
```

Fig. 6 (cont.)

```
SBDSP    gaggcgagcagataacacggtgaaaccctgtctctactaaaaatacaaaaaataagccag
              |       |      |    | | |  |    |  ||    |
MUSBDS   gcatctctacagcctctgaacccagggtcttgatgctaagcagtgctcactctcagtatg SBDS     gtgtggtggtggg-ttcctgtaatcccagtttcttgggaggctgaggcaggagaatcact
         ||||||||||||| | |||||||||||| ||||||||||| |||||||||||||||||||
SBDSP    gtgtggtggtgggcgt-ctgtaatcccagtgtcttggaggccgaggcaggagaatcact
           ||  |       |  ||        |         |        |      |
MUSBDS   agctgcagcactggccaggtgagtcttcaagggtgtcttaatcaggcttttactgctgtg SBDS     tgaacctggggaggcggaggctgcagtgagccaagatcacaccactgcactctatctc-aa
         ||||||||||||| ||||||||||||||||||||||||||||||||||||||||||| ||
SBDSP    tgaacctggggaggtggaggctgcagtgagccaagatcacaccactgcactctatctcaaa
              |||  |               ||||  |      |       |    |
MUSBDS   aacagacaccaggaccaatgcaagtcttataaagaacaacatttagttgagtctggctta SBDS     aaaaaaat--aa-attaacatacacatggtgtctacataagtcttcacattgcttttct
         ||||||||  || | |||||||||||||||||||| |||||||||||||||||||||||
SBDSP    aaaaaaataaaacaaaaacatacacatggtgtctacgtaagtcttcacattgcttttct
            |    |  |      |           || |    |      ||    |
MUSBDS   caggttcagaggttcagtccattatcaaggtgggagcatggtagtatccaggtgggaatg SBDS     ccttcatacgtggaggtgactttactgagctataaaatgtaatgctaaattttagtatga
         ||||||||||||||||||||||||||||||||||||||||||||||||||||||||||||
SBDSP    ccttcatacgtggaggtgactttactgagctataaaatgtaatgctaaattttagtatga
            |    |       |  ||    ||  ||            |      |  |
MUSBDS   atacaggaggggctgagagttcgacatcttcatctgaaggctgctagcagaatactgact SBDS     gaagaatcagagttttctagtttgtcccttccatttacagctgaagaatcagaataagtg
         |||||||||||||||||||||||||||||||||||||||||  |||||||||||||||||
SBDSP    gaagaatcagagttttctagtttgtcccttccatttacagcggaagaatcagaataagtg
           |       |||      ||   ||  |||| |      |       |||    |
MUSBDS   tcgaggctgttaggatgagggtcttaaagcctatgaccacagggacacaccttctaatag SBDS     tttaaacatagggattaatgccttgtcacaggggggctacatggacacttgagggcagagg
         ||||||||||||||||||||||||||||||||||||||||||||| |||||||||||||
SBDSP    tttaaacatagggattaatgccttgtcacaggggggctacatggatacttgagggcagagg
          | |    ||  ||      |     |        |            |      | |
MUSBDS   tgtcactccccgggctgagcatatacaaaccgtaacacgggataagtgcctttcccaaag
```

Fig. 6 (cont.)

```
                                                                 SDCR9x5Fseq →
SBDS    ctaaactggaacccagtgtgccgccctacccattgtcttatctattgcaccatagaactg
        || ||||||||||||||||||||||||||||||||||||||||||||||||||||||||||
SBDSP   ctgaactggaacccagtgtgccgccctacccattgtcttatctattgcaccatagaactg
        ||| ||      |          |            |         |           |
MUSBDS  tccaacagtaggtgcttagaatcgagacagaacccaggcccagcctgctgccctggcct SDCR9x5Fseq →
SBDS    tggtattattagagatctggacagcattgtgcttgcctcaaaggaagttaaagctgagtt
        ||||||    ||||||||||||||||||||||| ||||||  ||||||   ||||||||||||
SBDSP   tggtatta---gagatctggacagcattgtgcttgcctcaaag----ttaaagctgagtt
         |||  ||   ||||    |||       |   |     |    |   |      |   ||
MUSBDS  ccatgtgagcagcacctagaacacagtcatagatctgccctgagcattcaaactgggctt 625
                                                                     |
                                                                   v  c
SBDS    tattctgtgtcttgctcatcctcatgtggtaatctgctacgttaaatgtttcagGTATGT
        |||||||||||||||||||||||| |||||| |||||||||||||||||||||||||||||
SBDSP   tattctgtgtcttgctcatcctcatttggtaaactgctacgttaaatgtttcaggtatgt
            |   ||| |||| ||   ||| || | |||  |||    || ||||| ||
MUSBDS  attctgtgccgatgcccatcttcccttggaaaccagctgtgttactcattgcagGTGTGC
                                                              v  c L  I  D  P  G  C  F  R  E  I  D  E  L  I  K  K  E  T  K  G
SBDS    CTGATTGACCCGGGCTGCTTCCGAGAAATTGATGAGCTAATAAAAAAGGAAACTAAAGGC
        ||||||||| |||||||||||||||||||||||||||||||||||||||||||| ||||||
SBDSP   ctgattgacctgggctgcttccgagaaattgatgagctaataaaaaaggaaaccaaaggc
        || || |||| |||||||||  ||||||||||||||||||||||||||-|||||| ||||||
MUSBDS  CTCATCGACCCAGGCTGCTTCAGAGAAATTGATGAGCTAATAAAAAAGGAAACGAAAGGC
         L  I  D  P  G  C  F  R  E  I  D  E  L  I  K  K  E  T  K  G 750
                                                                    |
         K  G  S  L  E  V  L  N  L  K  D  V  E  E  G  D  E  K  F  E
SBDS    AAAGGTTCTTTGGAAGTACTCAATCTGAAAGATGTAGAAGAAGGAGATGAGAAATTTGAA
        |||||||||||||||||||||||||||||||||||| |||||||||||||||||||||||||
SBDSP   aaaggttctttggaagtactcaatctgaaagattt-gaagaaggagatgagaaatttgaa
        |  |||||| ||||||||| ||||  ||||||| || || ||||| |||||||| ||||||
MUSBDS  AGGGGTTCTCTGGAAGTGCTCAGTCTGAAGGACGTGGAGGAAGGCGATGAGAAGTTTGAA
         R  G  S  L  E  V  L  S  L  K  D  V  E  E  G  D  E  K  F  E SBDS    tgacacccatcaatctcttcacctctaaaacactaaagtgtttccgtttccgacggcact
        |||||||||||| |||||||||||||||||||||||||||||| ||||||| || |||||
SBDSP   tgacacccatcagtctcttcacctctaaaacactaaagtgttttcgtttccaacagcact
```

Fig. 6 (cont.)

```
                 |||||||  |     ||||||       |  ||  ||     |     |    |    |    |
        MUSBDS   TGAcaccgcccggctcctcaactggagcacgaccgaggacgcttgttcctcacagcagca SBDS     gtttcatgtctgtggtctgccaaatacttgcttaaactatttgacatttctatctttgt
                 |||||||||||||||||||||||||||||||||| |||||||||||||||||||||||||
        SBDSP    gtttcatgtctgtggtctgccaaatacttgctcaaactatttgacatttctatctttgt
                 |  |   |  ||  |    |    ||        |      |||  |      |   |||
        MUSBDS   gctcgttctgtgacctgccaaacgccctgctcacgcgacgtgccactttccatcttgtgt SBDS     gttaacagtggacacagcaaggctttcctacataagtataataatgtgggaatgatttgg
                 ||||||||||||||||||||||||||||||||||||||||||||||||||||||||||||
        SBDSP    gttaacagtggacacagcaaggctttcctacataagtataataatgtgggaatgatttgg
                 |   |   ||         |     |    |         |       |    |     |
        MUSBDS   taaacatttacccaggtacctgggtattttgttgtcaattggggtttccagcaaaaatg SBDS     ttttaattataaactggggtctaaatcctaaagcaaaattgaaactccaagatgcaaagt
                 ||||||||||||||||||||||||||||||||||||||||||||||||| |||||||  |
        SBDSP    ttttaattataaactggggtctaaatcctaaagcaaaattgaaactccaggatgcaaaat
                 |           ||        |          |            |
        MUSBDS   aaaaataacctaaaatacagagtccagaacagctgctcactgctgcgtctgcctttctag ← Primers L/R (RTSDCR95R/SDCR9x5BR)
        SBDS     ccagagtggcattttgctactctgtctcatgccttgatagctttccaaaatgaaagttac
                 ||||||||||||||||||||||||||||||||||||||||||||||||||||||||||||
        SBDSP    ccagagtggcattttgctactctgtctcatgccttgatagctttccaaaatgaaagttac
                   ||  ||       |  |   |    |              |  ·         |    |
        MUSBDS   ttccaggggaccagagacagcattggtggataagaaggtagagttagtccatgacagatc SBDS     ttgaggcagctcttgtgggtgaaaagttatttgtacagtagagtaagattattagggta
                 |||||||||||||||||||||||||||||| |||||||||||||||||||||||||||||
        SBDSP    ttgaggcagctcttgtgggtgaaaagttttttgtacagtagagtaagattattagggta
                 | |  ||  |       ||||    |  |   |    |       |         |||
        MUSBDS   attggagaggggtctgaataacaaaggggggtacgcctgctggaaagaagatggggtgttt SBDS     tgtctatacaacaaaagggggggtctttcctaaaaaagaaaacatatgatgcttcatttc
                 ||||||||  ||||||    |||||||||||||||||||| |||  |||||||||||||
        SBDSP    tgtctatacgacaaaa-ggggggtctttcctaaaaaagaaaac--atgatgcttcatttc
                    |  |||     ||    ||        |        ||    |            ||
        MUSBDS   ctgaataatgaagtgcaggtatggggtgtgagcatggagagaagagttcctgggtccctc
```

Fig. 6 (cont.)

```
SBDS    tacttaatggaacttgtgttctgagggtcattatggtatcgtaatgtaaagcttggatga
        ||||||||||||||||||||||||||||||||||||||||||||| ||||||||||||||
SBDSP   tacttaatggaacttgtgttctgagggtcattatggtatcgtaatataaagcttggatga
          ||   |        | |    | |    | |   |        |
MUSBDS  ccaatagatttataatgactagggagaatttgactttctaattttcaaccaacatgctac SBDS    tgttcctgattatctgagaaacagatatagaaaaattgtgccggac-t---tacctttca
        |||||||||||||||||||||||||||||||||||||||| |||||  |   ||  ||||
SBDSP   tgttcctgattatctgagaaacagatatagaaaaattgtgtcggacttaaataattttcg
        ||||       |  |  |     |  | |    | |    |   |         ||  |
MUSBDS  caaaactgacttagattattcttgggaaaatatatacagtcatttaatactaattcttaa SBDS    ttgaacatgctgccataacttagattattcttggttaaaaaataaaagtcacttatttct
        ||||||||||||||||||||||||||||||||||||||||||||||||||||||||||||
SBDSP   ttgaacatgctgccataacttagattattcttggttaaaaaataaaagtcacttatttct
         |   ||  |         || |.|    |  |    ||  ||   |      |   |||
MUSBDS  aggtttataatatatgttagtatagttaaaattctatgtaatcaataaaacttattttta (polyadenylation
site)                                                 |
SBDS    aattcttaaagtttataatatatattaatatagctaaaattgtatgtaatcaataaaacc
        ||||||||||||||||||||||||||||||||||||||||||||||||||||||||||||
SBDSP   aattcttaaagtttataatatatattaatatagctaaaattgtatgtaatcaataaaacc MUSBDS  c (end of human transcript, mRNA of 1605nt)
              |
SBDS    actcttatgtttattaaactatggcttgtgtttctagacaacttcctaactccctttctt
        ||||||||||||||||||||||||||||||||||||||||||||||||||||||||||||
SBDSP   actcttatgtttattaaactatggcttgtgtttctagacaacttcctaactccctttctt SBDS    ttctc
        |||||
SBDSP   ttctc
```

Fig. 6 (cont.)

DIAGNOSIS OF SHWACHMAN-DIAMOND SYNDROME

FIELD OF THE INVENTION

The invention relates to methods for diagnosing and treating individuals with Shwachman-Diamond Syndrome and for detecting Shwachman-Diamond disease carriers. More specifically, the invention relates to the identification of the Shwachman-Bodian-Diamond Syndrome (SBDS) gene and the identification of mutations of this gene which are associated with Shwachman-Diamond Syndrome.

BACKGROUND OF THE INVENTION

Shwachman-Diamond Syndrome (SDS [MIM 260400]) is an autosomal recessive disorder with clinical features including exocrine pancreatic insufficiency, haematological dysfunction, and skeletal abnormalities[1,2,3]. Patients with SDS have a high risk of bone marrow failure and are at risk of developing acute myelogenous leukaemia (AML). SDS is the second most common cause of pancreatic insufficiency after cystic fibrosis and involves the failure of development of the exocrine pancreas. Other manifestations include skeletal abnormalities and liver function abnormalities, the latter being notable in young patients.

Many SDS patients present with malabsorption and steatorrhea related to their pancreatic insufficiency. Many such children fail to thrive due to the malabsorption and also due to their disinclination to eat normally because of gastrointestinal upsets. The haematological dysfunction most consistently involves neutropenia but can also present as thrombocytopenia or pancytopenia. Serious consequences for SDS patients include recurring severe infections that can be life threatening if the diagnosis is not made with the provision of prompt treatments. Further, traditional methods for treatment of bone marrow failure are generally not successful in SDS patients at this time but the surveillance and monitoring of the bone marrow to determine the occurrence of myelodysplasia, aplastic anaemia and/or the development of AML do provide some options for intervention.

It is therefore important for the optimum development and overall long term prognosis of these children that they are diagnosed as having SDS as early as possible so that infections may be treated with appropriate interventions, so that blood and bone marrow can be monitored for cellularity (numbers and cell types) and so that pancreatic enzyme supplementation may be instituted to provide adequate or near normal food absorption.

There are other diseases associated with exocrine pancreatic dysfunction, such as Cystic Fibrosis and Pearson Marrow Syndrome, and other diseases such as congenital neutropenia, Blackfan-Diamond Syndrome and Fanconi Anaemia can mimic the haematological manifestations of SDS. It is important, for proper treatment, that SDS is diagnosed as early as possible but at present SDS can only be distinguished from other diseases causing similar symptoms by complex, symptom-based tests which may have to be repeated many times before a conclusion is reached (Rothbaum et al., (2002), J. Pediatrics, v. 141, pp. 266-270; Ginzberg et al., (2000), Am. J. Hum. Genet., v. 66, pp. 1413-1416).

There is therefore a real need for a convenient and definitive test, such as a genetic test or a gene product-based immunological test, to diagnose SDS. Further, as the bone marrow failure aspects are so serious, there is need to provide new options to correct the associated deficiencies. The identification and analysis of the gene that is affected in SDS would provide for such opportunities.

Segregation analysis of an international collection of families of SDS patients supports an autosomal recessive mode of inheritance (Ginzberg et al., (2000), Am. J. Hum. Genet., v. 66, pp. 1413-1416). Previous studies of families with SDS showed that the putative SDS locus mapped to the centromeric region of chromosome 7, to a 1.9 cM interval at 7q11[4,5]. The genetic defect associated with the disease has, however, not previously been identified.

SUMMARY OF THE INVENTION

The invention provides a convenient and rapid method for the diagnosis of SDS, based on the finding that SDS is associated with mutations in a previously uncharacterised gene residing within the 1.9 centiMorgan disease interval at 7q11 delineated by linkage and haplotype analysis in family studies[4,5]. The gene, with a 1.6 kb transcript, was originally designated by the inventors as DEPCH and its encoded protein of 250 amino acids was designated depechin. The gene has been renamed as Shwachman-Bodian-Diamond Syndrome (SBDS) gene. A second copy previously designated DEPCHP and now designated SBDSP, with 97% nucleotide sequence identity, resides within a locally duplicated genomic block of at least 305 kb, and appears to be a pseudogene. Recurring mutations, the apparent result of recombination between the duplicated gene copies, were found in 89% of unrelated SDS patients (n=158), with 60% carrying two converted alleles and 29% having a different mutation in the second allele. The extent of the converted segments varied but consistently included at least one of two critical sequence changes predicted to result in truncation of the encoded protein. Other less common disease alleles involve missense and insertion/deletion changes distinct from those in the pseudogene. The gene is a member of a highly conserved protein family, with putative orthologues in diverse species ranging from archæbacteria to eukaryotes. The archaeal orthologues are located within highly conserved operons that include homologues of genes involved in RNA processing[6], suggesting that SDS may be the result of a deficiency in some aspect of RNA metabolism that is essential for hæmatopoiesis, chondrogenesis and the development of the exocrine pancreas.

"SBDS or SBDS gene" is the chromosome 7q11.22 gene as described herein which when mutated is associated with SDS. This definition includes sequence polymorphisms wherein the nucleotide substitutions in the gene sequence do not affect the function of the gene product.

"SBDS protein" is the protein encoded by the SBDS gene.

"Mutant SBDS gene" is the SBDS gene containing one or more mutations which, if present on both alleles of the gene, lead to SDS.

In accordance with one embodiment, the invention provides a method for determining whether a subject is suffering from Schwachman-Diamond Syndrome (SDS) comprising obtaining a nucleic acid sample from the subject, and conducting an assay on the nucleic acid sample to determine the presence or absence of a SBDS gene mutation associated with SDS, wherein the presence of a SBDS gene mutation associated with SDS in both SBDS alleles indicates that the subject suffers from SDS.

In accordance with a further embodiment, the invention provides a method for determining whether a subject is an SDS carrier comprising obtaining a nucleic acid sample from the subject, and conducting an assay on the nucleic acid sample to determine the presence or absence of a SBDS gene mutation associated with SDS, wherein the presence of a SBDS gene mutation associated with SDS in one SBDS allele indicates that the subject is an SDS carrier.

In accordance with a further embodiment, the invention provides a method for determining whether a subject is suffering from Shwachman-Diamond Syndrome (SDS) comprising obtaining a tissue sample from the subject, and conducting an assay on the tissue sample to determine the level of SBDS protein in the sample, wherein a reduced level of SBDS protein in the sample relative to a control sample indicates that the subject suffers from SDS.

In accordance with a further embodiment, the invention provides a method for determining whether a subject is at risk for developing acute myelogenous leukaemia (AML) comprising obtaining a nucleic acid sample from the subject, and conducting an assay on the nucleic acid sample to determine the presence or absence of a SBDS gene mutation associated with SDS, wherein the presence of a SBDS gene mutation associated with SDS indicates that the subject is at risk for development of AML.

In accordance with a further embodiment, the invention provides a method for treating a subject suffering from SDS comprising administering to the subject a therapeutically effective amount of a substantially purified SBDS protein or of an isolated nucleotide sequence encoding an SBDS protein.

In accordance with a further embodiment, the invention provides an isolated nucleic acid molecule encoding an SBDS protein.

In accordance with a further embodiment, the invention provides an isolated nucleic acid molecule comprising at least about 10, 20, 30, 50, 75 or 100 consecutive nucleotides of SEQ ID NO:1 or 29.

In accordance with a further embodiment, the invention provides a substantially purified SBDS protein.

In accordance with a further embodiment, the invention provides an antibody which binds specifically to an epitope of an SDS protein.

In accordance with a further embodiment, the invention provides a nucleotide sequence selected from the group consisting of:

```
(a)
5'-GCGTAAAAAGCCACAATAC-3';            (SEQ ID NO: 3)

(b)
5'-CTATGACAGTATTCGTAAGACTAGG-3';      (SEQ ID NO: 4)

(c)
5'-GGGGATTTGTTGTGTCTTG-3';            (SEQ ID NO: 5)

(d)
5'-CTTTCCTCCAGAAAAACAGC-3';           (SEQ ID NO: 6)

(e)
5'-AAATGGTAAGGCAAATACGG-3';           (SEQ ID NO: 7)

(f)
5'-ACCAAGTTCTTTATTATTAGAAGTGAC-3';    (SEQ ID NO: 8)

(g)
5'-GCTCAAACCATTACTTACATATTGA-3';      (SEQ ID NO: 9)
```

-continued
```
(h)
5'-CACTTGCTTCCATGCAGA-3';             (SEQ ID NO: 10)

(i)
5'-AAAGGGTCATTTTAACACTTC-3';          (SEQ ID NO: 11)

(j)
5'-GAAAATATCTGACGTTTACAACA-3';        (SEQ ID NO: 12)

(k)
5'-TCCACTGTAGATGTGAACTAACTC-3';       (SEQ ID NO: 13)

(l)
5'-CACTCTGGACTTTGCATCTT-3';           (SEQ ID NO: 14)

(m)
5'-GCTTCTGCTCCACCTGAC-3';             (SEQ ID NO: 15)

(n)
5'-AGCTATGCTGCAGCTGTTAC-3';           (SEQ ID NO: 16)

(o)
5'-ATGCATGTCCAAGTTTCAAG-3';           (SEQ ID NO: 17)

(p)
5'-TCCATGGCTATATTTTGATGA-3';          (SEQ ID NO: 18)

(q)
5'-TAAGCCTGCCAGACACAC-3';             (SEQ ID NO: 19)

(r)
5'-CACTCTGGACTTTGCATCTT-3';           (SEQ ID NO: 20)

(s)
5'-TGTTGGTTTTCACCGAATA-3';            (SEQ ID NO: 21)

(t)
5'-AGATAAAGAAAGACACACACAACT-3';       (SEQ ID NO: 22)

(u)
5'-GAAATCGCCTGCTACAAA-3';             (SEQ ID NO: 23)

(v)
5'-TCAGCTTCTTGCCTTCAT-3';             (SEQ ID NO: 24)

(w)
5'-TAAGTAAGCCTGCCAGACA-3';            (SEQ ID NO: 25)

(x)
5'-CATCAAGGTCTTTTTCCAAG-3';           (SEQ ID NO: 26)

(y)
5'-CCTGTCTCTGCCCAAGTC-3';             (SEQ ID NO: 27)
and (z)
5'-AGGGAACATTTTCAAAACTCA-3'.          (SEQ ID NO: 28)
```

In accordance with a further embodiment, the invention provides a transgenic non-human mammal having within its genome an SBDS gene with at least one mutation associated with SDS.

In accordance with a further embodiment, the invention provides a kit comprising at least one pair of primers suitable for amplification of at least a portion of an SBDS gene.

SUMMARY OF DRAWINGS

The patent or application file contains at least one drawing executed in color. Copies of this patent or patent application publication with color drawing(s) will be provided by the Office upon request and payment of the necessary fee.

FIG. 4 shows CLUSTALX alignment of SBDS-encoded protein, SBDS, and representative orthologues. Strong conservation is seen throughout the alignment from archæbacteria to complex eukaryotes. '*' represents absolutely conserved residues in the alignment, ':' represents positions at which conservative amino acid substitutions are observed and '.' represents semi conservative substitutions. The degree of sequence similarity is less pronounced towards the C-terminus although subgroups retain strong conservation. The human amino acid sequence (Hsa) is shown in bold. The locations of all identified coding mutations are represented as white letters on a black background and corresponding amino acid sequence changes are shown above the alignment. A putative U1-like zinc finger domain in three plant orthologues is indicated with a black bar. Ath *Arabidopsis thaliana*, Dme *Drosophila melanogaster*, Cel *Caenorhabditis elegans*, Mmu *Mus musculus*, Hsa *Homo sapiens*, Ola *Oryzias latipes*, Sce *Saccharomyces cerevisiae*, Ecu *Encephalitozoon cuniculi*, Mac *Methanosarcina acetivorans* str. C2A, Hnr *Halobacterium* sp. NRC-1, Mka *Methanopyrus kandleri* str. AV19, Mja *Methanococcus jannaschii*, Afu *Archaeoglobus fulgidus*, Pab *Pyrococcus abyssi*, Tac *Thermoplasma acidophilum*, Pae *Pyrobaculum aerophilum*, Sso *Sulfolobus solfataricus*, Ape *Aeropyrum pernix*, Pba *Populus balsamifera*, Gar *Gossypium arboreum*, +derived from partial GenBank EST sequence.

FIG. 5 shows the SBDS cDNA and its predicted encoded polypeptide. A: The nucleotide sequence of the cDNA corresponding to SBDS mRNA is shown numbered with the +1 starting at the first nucleotide, A, of the translation initiating codon. The 5' and 3' untranslated regions are shown in lower case, and the coding segment is shown in upper case text. B: amino acid sequence of the encoded polypeptide of 250 amino acids is shown numbered.

FIG. 6 shows the aligned genomic sequence for the human SBDS gene (SBDS) and its pseudogene SBDSP (SBDSP) and for the mouse SBDS gene (MUSBDS). The sequences for the five human exons are included with numbering that corresponds to that indicated in FIG. 5A. SBDS specific oligonucleotide primers that can be used to determine the nucleotide sequence of expressed RNA or of each of the exons for mutation detection are indicated by underlining of the <u>SBDS</u> sequence. Dual specific oligonucleotide primers are indicated by the underlining of both SBDS and SBDSP sequences. The sequence of oligonucleotide primers indicated in the forward direction (the arrows pointing to the right) correspond directly to the sequence shown, while those primers in the reverse direction (the arrows pointing to the left) are comprised of the reverse complement of the indicated sequence.

FIG. 7 shows the specificity and reactivity of antibodies produced to detect the SBDS protein. a, Polyclonal antibodies produced with recombinant SBDS (anti-rSBDS), left panel or a carboxyl peptide (anti-CpSBDS) of amino acids 224-239 (aa[224]IKKETKGKGSLEVLNL[239] SEQ ID NO:29) of SBDS, right panel, detected single bands of the predicted size in whole cell extracts of induced host E. coli BL21 containing the pET-28a expression vector with an in-frame fusion of the entire SBDS open reading frame. A polyclonal antibody to an amino peptide (anti-NpSBDS) of amino acids 32-47 (aa[32]CYKNKVVGWRSGVEKD[47] SEQ ID NO:30) of SBDS has also been generated, data not shown. b, The anti-rSBDS antibody also detected SBDS expressed transiently in HEK293 cells under the control of a CMV promoter. The bands corresponds to those detected by anti-Myc or anti-HA antibodies. The subtle shifts in sizes are due to the various epitope tags and/or their locations that have been fused in frame to the SBDS gene, including amino or carboxyl positioned Myc (N-Myc or C-Myc) N-HA or amino or carboxyl positioned HA (N-HA or C-HA) tags. c, Anti-rSBDS also detected a prominent band in whole cell extracts of the predicted size for SBDS in BxPC3 (ATCC CRL-1687), SV40-transformed human fibroblasts (GM00639), Caco-2 (ATCC HTB-37), AR42J (ATCC CRL-1492), EBV transformed human lymphoblast (GM003798), PANC1 (ATCC CRL-1469) and J.RT3 (ATCC TIB-153) cell lines. The total protein loaded per extract is as indicated below each panel.

DETAILED DESCRIPTION OF THE INVENTION

The inventors have identified the SBDS gene and described the association of mutations in that gene with the autosomal recessive disease, SDS.

Figure 1:
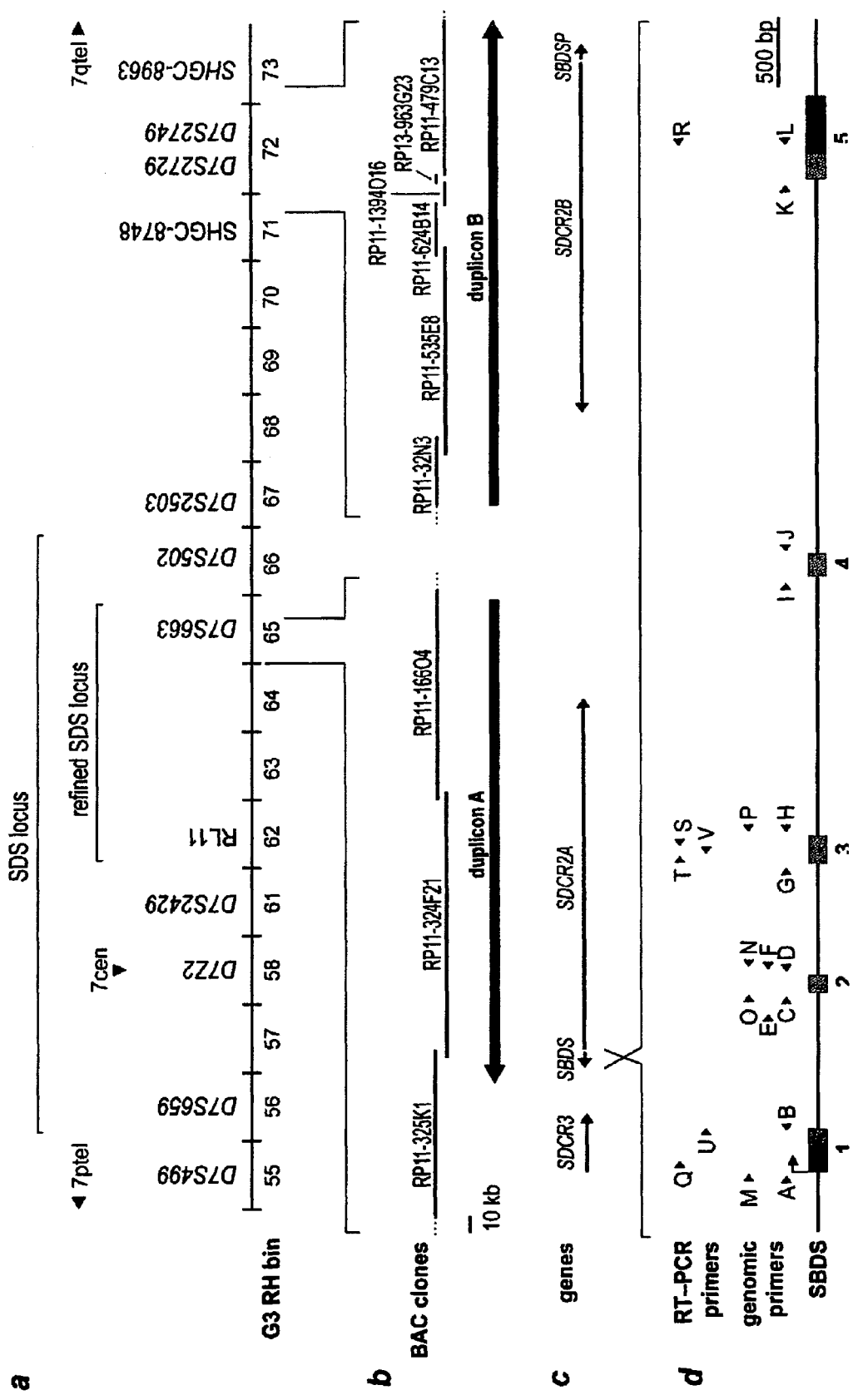
FIG. 1 shows an integrated map of the interval of chromosome 7 where the gene deficiency that leads to SDS resides. a, The refined map interval, flanked by microsatellite markers D7S2429 and D7S502, is shown with reference to the Genbridge 3 radiation hybrid panel. b, An expanded map of sub regions from RH bins 65 and 72 based on genomic sequences from BAC clones in GenBank. The regions contains at least 305 kb that has duplicated intrachromosomally. The positions and orientations of the paralogous duplicons along 7q were determined by unique STS content and radiation hybrid mapping. c, Identified genes in the BAC contigs are shown. Duplicon A contains at least 2 genes, SBDS and SDCR2A (Shwachman-Diamond Critical Region-2A). d, SBDS is composed of 5 exons (coding regions in grey, noncoding regions in black) spanning 7.9 kb of genomic sequence. The location of oligonucleotide primers used for mutation screening by genomic PCR and RT-PCR are indicated.

Clinical presentation in SDS can be variable but family studies have supported a single gene locus near the centromere at 7q11[2,4,5]. Eighteen positional candidate genes were identified in compiled genomic sequences from the locus, and eight of these were analysed for mutations in members of linked families. Disease-associated changes were identified in a gene represented by the full length, 1.6 kb cDNA clone flj10917 (OVARC1000321). The gene was initially designated by the inventors as DEPCH (Development of Exocrine Pancreas, Chondrocytes and Hæmatological lineages). The gene has been renamed (as approved by the Human Genome Organisation Gene Nomenclature Committee) as Shwachman-Bodian-Diamond Syndrome (SBDS) gene. The cDNA sequence is given in FIG. 5A (SEQ ID NO:1). SBDS is composed of 5 exons spanning 7.9 kb, and is contained in BAC clone RP11-325K1. The nucleotide sequences of the exons and surrounding introns are given in FIG. 6. The sequence of murine SBDS is also shown in FIG. 6. SBDS and part of an adjacent gene reside in a block of genomic sequence of at least 305 kb that is locally duplicated (FIG. 1). The paralogous duplicon was mapped distally, and contains an unprocessed pseudogene copy of SBDS, named SBDSP. The pseudogene transcript is 97% identical to the SBDS transcript with small deletions and single nucleotide changes that clearly disrupt coding potential. The mouse and human SBDS genes have 88% nucleotide identity and the proteins 97% amino acid identity, as seen in FIG. 6.

The protein product encoded by SBDS, termed SBDS, is a member of a highly conserved protein family (Pfam UPF00023)[20]. Orthologues exist in species ranging from archæbacteria to vertebrates and plants (FIG. 4). The sequence of 250 amino acids is given in FIG. 5B (SEQ ID NO:2) for a predicted polypeptide of 28.8 kDa with a pI of 8.9. The predicted amino acid sequence has no homology to any known functional domain, and no signal peptides were detected. The S. cerevisiae orthologue, encoded by ORF YLR022c, has been found to bind specifically and with high affinity to the phospholipids PI(4,5)P2 and PI(4)P using yeast proteome chips[21]. The gene has also been deleted by the Yeast ORF Deletion Project and haploid spores lacking YRL022c were found to be inviable[22]. Indirect lines of evidence suggest that orthologues of SBDS may play a role in RNA metabolism. First, YLR022c has been clustered with other genes encoding RNA processing enzymes based on microarray expression profile analysis[23]. In addition, SBDS archæl orthologues are located in conserved operons that contain several RNA processing genes, including homologues of subunits of the eukaryotic exosome and RNaseP complexes[8]. The A. thaliana orthologue, along with sequences derived from partial cDNAs from P. balsamifera and G. arboreum, have extended carboxyl termini corresponding to putative RNA-binding domains, suggesting a functionally relevant fusion in flowering plants (FIG. 4). These observations suggest that SDS may be the result of a defect in an RNA processing pathway. Manifestation of disease must reflect the loss or perturbation of a cellular function that is particularly critical for the development of pancreatic acini, myeloid lineages, and chrondrocytes at growth plates of bones. The associated symptoms and the complications due to bone marrow failure may reflect not only the loss of one gene but also pleiotropic consequences of an aberrant pathway.

Sequence changes that do not alter protein-associated activities and that occur in normal individuals are likely to correspond to gene polymorphisms. A current accepted standard to discriminate polymorphisms from mutations is to screen 100 individuals of comparable ethnic background that are not affected with SDS. Examples of polymorphisms detected in SBDS are given in Table 2. SDS-associated mutations are shown in Table 1.

Diagnostic Methods

The invention provides a diagnostic method for determining whether a subject, such as a human subject, suffers from, or is at risk of developing, symptoms of SDS. In one embodiment, the method involves examining a nucleic acid sample from the subject for the presence or absence of a mutation of the SBDS gene associated with SDS. Such mutations include 183_184TA→CT; 183_184TA→CT+258+2T→C; 258+2T→C; 24C→A; 96-97insA; 119 delG; 131A→G; 199A→G; 258+1G→C; 260T→G; 291-293delTAAinsAGT-TCAAGTATC; 377G→C; 505C→T; 56G→A; 93C→G; 97A→G; 101A→T; 123delC; 279_284delTCAACT; 296_299delAAGA; 354A→C; 428C→T+443A→G; 458A→G; 460-1G→A; 506G→C; and 624+1G→C. These mutations are identified in relation to the numbering of the nucleotide sequence of SEQ ID NO:1.

Many methods known to those of skill in the art can be used to detect the presence or absence of a SBDS gene mutation in the subject's nucleic acid.

The cDNA sequence of the wild type SBDS gene is shown in FIG. 5 and is available at GenBank Accession Number AY169963 (NM_016038). The exon structure and flanking intron sequences are shown in FIG. 6.

"Mutations" of the wild type SBDS gene associated with SDS include conversions, deletions, insertions, inversions or point mutations, either in the coding regions of the gene or gene regulatory regions.

A number of types of assay may be used to determine whether a subject has an SBDS gene mutation associated with SDS, including, for example, sequencing exons or other portions of the gene, including regulatory or intronic segments, PCR-RFLP analysis, allele specific PCR, allele specific oligonucleotide hybridisation restriction fragment length polymorphism (RFLP) analysis.

Where a direct sequencing assay is used, the sample may be DNA or RNA, for example genomic DNA or mRNA. Gene-controlling DNA segments and exons of an individual can be amplified and then examined for direct sequence changes, or scanned with methods that detect a heterozygous state followed by sequencing. These latter scanning methods can include single stranded conformational analysis (Orita M, Iwahana H, Kanazawa H, Hayashi K and Sekiya T (1989), "Detections of polymorphisms of human DNA by gel electrophoresis as single-stranded conformation polymorphisms", *Proc. Natl. Acad. Sci, USA* 86: 2776-2770), denaturing gradient gel electrophoresis (Wartell R M, Hosseini S H and Moran C P Jr (1990), "Detecting base pair substitutions in DNA fragments by temperature-gradient gel electrophoresis", (*Nucleic Acids Res.* 18: 2699-2705; Sheffield V C, Cox D R, Lerman L S and Myers R M (1989) or "Attachment of a 40-base-pair G+C rich sequence (GC clamp) to genomic DNA fragments by the polymerase chain reaction results in improved detection of single-base changes" (*Proc. Natl. Acad. Sci, USA* 86: 232-236); and denaturing high pressure liquid chromatography Cotton R G H, Edkins E, Forrest S (eds) 1998 "Mutation detection: a Practical Approach" IRL Press, Oxford, and heteroduplex analysis Keen J, Lester D, Inglehearn C, Curtis A, Bhattacharya S (1991) Rapid detection of single base mismatches as heteroduplexes on Hydrolink gels. *Trends Genet.*, 7:5, amongst other methods. Larger deletions or insertions can be detected by traditional Southern blot analysis of DNA digest with restriction enzymes (Southern E M. (1975) 'Detection of specific sequences among DNA fragments separated by gel electrophoresis', J Mol Biol 98:503-17). Mutant alleles can be distinguished by observing their inheritance from each parent and although each patient will have two affected alleles, they will typically appear in heterozygous state (all of the references of this paragraph are incorporated herein by reference).

The diagnostic methods of the invention are used to screen subjects showing symptoms of possible SDS, such as pancreatic insufficiency to identify SDS, or to screen relatives of known SDS cases to determine whether they may be at risk of developing SDS symptoms.

The diagnostic method of the invention should preferably be carried out on samples from children at a young age in order to establish the diagnosis and allow appropriate treatment. The diagnostic method may also be used as a prenatal test, using amniotic fluid or CVS samples.

With respect to determining carrier status, as discussed below, the test may be carried out at any age, preferably at an age greater than 16 years in relatives of SDS patients.

Signs of SDS generally are evident in children at an early age and the diagnostic methods of the invention will usually be employed to determine if a child presenting with SDS symptoms is indeed suffering from SDS. On occasion, a sibling or close relative may be screened to determine if he or she suffers from SDS.

Suitable samples for testing of nucleic acid include buccal swabs, blood samples and bone marrow aspirates.

In one embodiment, genomic DNA is extracted from the sample and a target portion of the genomic DNA comprising the SBDS gene or a selected portion thereof is amplified by a polymerase chain reaction using suitable oligonucleotide primers, such as those described herein. The amplified nucleic acid is then sequenced using conventional techniques. The sequence is compared with the wild type sequence to determine the presence or absence of SDS-associated mutations. Primers must be selected which will amplify only the SBDS gene and not the pseudogene, as shown in FIG. 6. Since a larger number of SDS-associated mutations have been observed in exon 2 of SBDS gene, it is preferable to look first for mutations in that exon. If no mutations are found in exon 2, exons 1 and 3 to 5 are similarly examined in turn.

One of skill in the art can select suitable primers by reference to the SBDS sequence of FIG. 6, suitable primers are also identified in Example 1. Preferred primer pairs for amplification of SBDS exons are as follows:

```
Exon 1:    A & B or Q & B;

Exon 2:    E & F;

Exon 3:    G & H;

Exon 4:    SDCR9x4seqB;
           (5'-GCCTTCACTTTCTTCATAGT-3':
           SEQ ID NO: 31) & J; and Exon 5:    SDCR9x5Fseq
           (5'-GCTTGCCTCAAAGGAAGTT-3':
           SEQ ID NO: 32) & L.
```

Regulatory regions of SBDS, such as the promoter region, may also be examined using suitable primers.

```
Promoter primers include SDCR9prom1RA
(5'-CAGCCGACGACCTTGTTTT-3':        SEQ ID NO: 33)
and SDCR9prom6FA
(5'-GTGCCAACGCTGTGTTTT-3':         SEQ ID NO: 34).
```

These primers amplify a 501 bp segment partially overlapping exon 1, which likely contains the major controlling elements for the transcription of SBDS mRNA.

For conversion mutations found in exon 2, examination of the test subject's parents can be used to distinguish whether the subject has two conversion recombinations rather than one extended conversion recombination.

In a further embodiment of the invention, an RNA sample is obtained from the test subject and is reverse transcribed by conventional methods to give a corresponding cDNA which is amplified by PCR and sequenced.

In a further embodiment, RFLP analysis may be used to detect SBDS gene mutations. Such methods of analysis are well known to those of skill in the art and an example is described in the Examples herein and in reference 30. Test samples are compared with normal controls and samples from patients with known mutations.

Figure 3:
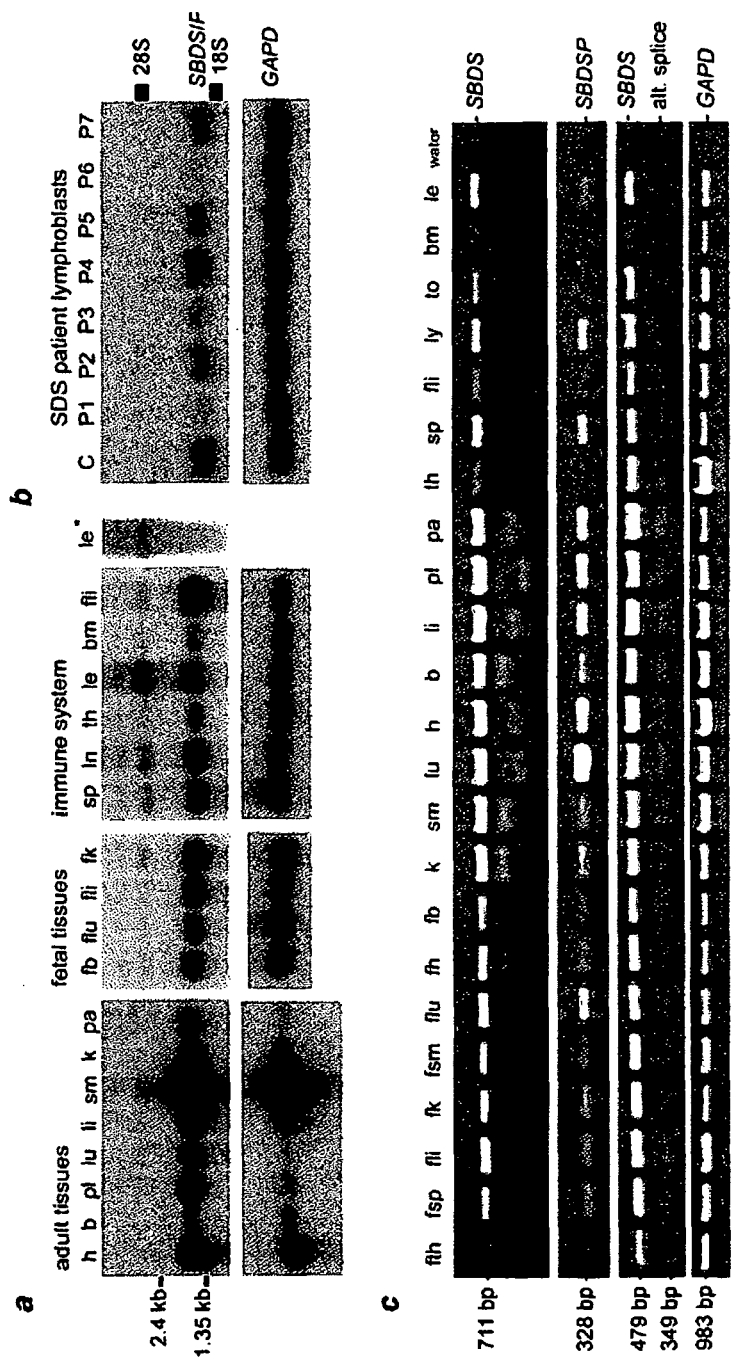
FIG. 3 shows expression analysis of SBDS and SBDSP. FTh Fetal thymus, FSp Fetal spleen, FLi Fetal Liver, FK Fetal kidney, FSM Fetal skeletal muscle, FLu Fetal lung, FH Fetal heart, FB Fetal brain, K Kidney, SM Skeletal muscle, Lu Lung, H Heart, B Brain, Li Liver, Pl Placenta, Pa Pancreas, Th Thymus, Sp Spleen, Ly Lymphocytes, To Tonsil, BM Bone Marrow, Le Peripheral Blood Leukocytes, LN Lymph Node, GAPDH Glyceraldehyde-3-Phosphate Dehydrogenase. a, RNA expression survey of SBDS and SBDSP in primary tissues using a cloned RT-PCR product containing the entire SBDS open reading frame (primers T and R). Cumulative levels of both gene and pseudogene transcripts appear to be lower in thymus and bone marrow. An alternatively spliced product was detected in several tissues and was most prominent in peripheral blood leukocytes (Le). As shown in the lane indicated with an asterisk, this large transcript was detected with a probe derived from intron 1. b, Analysis of patient EBV-transformed B lymphoblastoid-derived RNA shows that SBDS and SBDSP cumulative expression is lower in some patients compared to a control individual (C). The probe used to provide a control for RNA loading consisted of a 983 bp cloned cDNA fragment from glyceraldehyde 3-phosphate dehydrogenase (GAPDH). c, RT-PCR expression analysis of SBDS and SBDSP was carried out with specific oligonucleotide primers and indicated that both transcripts are widely expressed. Sequencing of PCR products led to the identification of an exon $2^{minus}$ transcript. RT-PCR indicated that the alternatively spliced product (shown as 349 bp) is present in all tissues tested, however its expression is significantly lower than transcripts that include exon 2 (shown as 479 bp).

In a further embodiment, analysis of SBDS expression or of the level of SBDS protein may used to determine whether a subject suffers from or is at risk of SDS. As described herein, SBDS is expressed in a wide variety of tissues, including the most disease-relevant tissues, pancreas, bone marrow and myeloid cell lineages. A blood or tissue sample may therefore be used to evaluate SBDS expression or SBDS protein level. As seen in FIG. 3b, mRNA level is notably reduced in SDS patients. SBDS expression can be evaluated by many routine methods, for example by mRNA analysis as described in the Examples herein and in reference 30.

In a further embodiment, an antibody specific for SBDS protein and carrying a detectable label can be used to assess the level of SBDS protein in a tissue sample of a subject by an immunological technique. Many suitable techniques, such as immunoprecipitation or ELISA assays, are known to those of skill in the art and are described, for example, in "Using antibodies—a laboratory manual", (1999), Harlow et al., Cold Spring Harbor Lab. Press. The level of protein in a test subject is compared with that in similar tissue samples from unaffected individuals, a reduction in level of SBDS protein being indicative of SDS. The identification of the SBDS gene and the absence of any known closely related homologues enables the preparation of antibodies highly specific for SBDS protein.

Detection of SDS Carriers

The invention further provides a method for determining whether a subject is an SDS carrier by determining whether the subject has an SDS-associated mutation in one allele of the SBDS gene.

The methods described above for detecting an SDS-associated mutation in a sample from a subject suspected of suffering from SDS may also be applied to detect carriers of the disease. The described methods for detecting such mutations in a nucleic acid sample from a subject are preferred.

Screening for SDS carriers is carried out especially on members of families with known SDS cases and may be important for genetic counselling of such family members regarding their likelihood of passing the disease on to their children. Generally, a method would be used to look for a specific mutation already found in an affected family member.

Identification of Further Mutations

The present invention also enables the identification of additional SDS-associated mutations of the SBDS gene, for example by examining SDS patients using the methods and primers described herein.

Amplification of target portions of the gene, followed by direct nucleic acid sequencing, as described herein for diagnostic purposes, and comparison with the wild type sequence, may be used to identify additional SDS-associated mutations.

Alternatively, assessment of the expression level of the SBDS gene, as described herein, may indicate reduced expression levels and point to further mutations which can be characterised by nucleic acid analysis as described above.

Nucleic Acids

The invention provides SBDS nucleic acids and homologues and portions thereof. Preferred nucleic acids have a nucleotide sequence which is at least 80%, preferably at least 90% and more preferably more than 97% homologous to the nucleotide sequence of SEQ ID NO:1 or SEQ ID NO:29 or to a complement thereof.

Preferred nucleic acids are mammalian and especially preferred are human nucleic acids. Nucleic acids of the invention include nucleic acids encoding an amino acid sequence with at least 75%, preferably at least 90% and more preferably at least 99% amino acid identity to the amino acid sequence of SEQ ID NO:2, and nucleic acids encoding a portion of such amino acid sequences.

Also within the scope of the invention are nucleic acid molecules useful as probes or primers and comprising at least about 10, 20, 30, 50, 75, 90 or 100 consecutive nucleotides of SEQ ID NO:1.

Also within the scope of the invention are nucleic acids which hybridise under stringent conditions to a nucleic acid of the nucleotide sequence SEQ ID NO:1 or to a complement or a portion thereof. Stringent conditions for nucleic acid hybridisation are known to those skilled in the art and are described, for example, in "Protocols in Molecular Biology", (1989), John Wiley & Sons, N.Y., at 6.3.1 to 6.3.6.

Also within the scope of the invention are nucleic acids which differ from the sequence of SEQ ID NO:1 due to the degeneracy of the genetic code.

Proteins

The invention provides substantially purified SBDS proteins and portions thereof. These proteins and portions thereof are useful for the preparation of antibodies specific for SBDS proteins.

"Substantially purified" as used herein with respect to proteins means a protein preparation which is at least 75%, more preferably at least 90% and most preferably at least 99% by weight of SBDS protein.

Preferred SBDS proteins have an amino acid sequence which is at least about 75%, preferably at least about 90% and more preferably at least about 99% identical to the amino acid sequence of SEQ ID NO:2.

In a preferred embodiment, the SBDS protein has the amino acid sequence of SEQ ID NO:2. Full length proteins and portions thereof corresponding to one or more domains thereof or comprising at least 5, 10, 25, 50, 75 or 100 consecutive amino acids of SEQ ID NO:2 are within the scope of the invention.

The proteins and peptides of the invention may be isolated and purified by conventional protein purification methods such as gel-filtration chromatography, ion exchange chromatography, high performance liquid chromatography, immunoprecipitation or immunoaffinity purification.

SBDS proteins may be prepared by conventional recombinant methods, for example using the cDNAs described herein (for example human sequence has Genbank Accession Number AY169963) or a selected portion thereof. Since the SBDS gene is small, native gene expression may be achieved with the incorporation of natural promoter and enhancer gene elements. Suitable vectors and host cells for such expression are well known to those of skill in the art.

The expressed protein can be purified by standard procedures, as described above.

Antibodies

The present invention also enables the preparation of antibodies or antibody fragments which bind specifically to SBDS protein or to a portion thereof.

The term "antibody" means a monoclonal antibody or a polyclonal antibody, which binds specifically to a particular peptide, polypeptide or epitope, i.e. with greater affinity than to other peptides, polypeptides or eptiopes, and includes chimeric antibodies, humanised antibodies and single chain antibodies.

Chimeric antibodies are antibodies which contain portions of antibodies from different species. For example, a chimeric antibody may have a human constant region and a variable region from another species. Chimeric antibodies may be produced by well known recombinant methods, as described in U.S. Pat. Nos. 5,354,847 and 5,500,362, and in the scientific literature (Couto et al., (1993), Hybridoma, 12:485-489).

Humanised antibodies are antibodies in which only the complementarity determining regions, which are responsible for antigen binding and specificity, are from a non-human source, while substantially all of the remainder of the antibody molecule is human. Humanised antibodies and their preparation are also well known in the art—see, for example, U.S. Pat. Nos. 5,225,539; 5,585,089; 5,693,761 and 5,693, 762.

Single chain antibodies are polypeptide sequences that are capable of specifically binding a peptide or epitope, where the single chain antibody is derived from either the light or heavy chain of a monoclonal or polyclonal antibody. Single chain antibodies include polypeptides derived from humanised, chimeric or fully-human antibodies where the single chain antibody is derived from either the light or heavy chain thereof.

The term "antibody fragment" means a portion of an antibody that displays the specific binding of the parent antibody and includes Fab, F (ab')$_2$ and Fv fragments.

Polyclonal Antibodies

In order to prepare polyclonal antibodies, purified SBDS protein may be obtained, for example, as described herein. The purified protein or a portion thereof, coupled, if desired, to a carrier protein such as bovine serum albumin or keyhole limpet hemocyanin, as in Cruikshank W W, Center D M, Nisar N, Wu M, Natke B, Theodore A C, and Kornfeld H., (1994), Proc. Natl. Acad. Sci. USA 24: 5109-5113, is mixed with Fruend's adjuvant and injected into rabbits or other suitable laboratory animals.

Following booster injections at weekly intervals, the rabbits or other laboratory animals are then bled and the sera isolated. The sera can be used directly or purified prior to use by various methods including affinity chromatography employing Protein A-Sepharose, antigen Sepharose or Antimouse-Ig-Sepharose. Further purification methods well known in the art may be utilised to remove viral and/or endotoxin contaminants.

Monoclonal Antibodies

As will be understood by those skilled in the art, monoclonal antibodies may also be produced using an SBDS protein or a portion thereof. The protein or portion thereof, coupled to a carrier protein if desired, is injected in Freund's adjuvant into mice. After being injected three times over a three-week period, the mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened by ELISA to identify those containing cells making binding antibody. These are then plated and after a period of growth, these wells are again screened to identify antibody-producing cells. Several cloning procedures are carried out until over 90% of the wells contain single clones which are positive for antibody production. From this procedure a stable line of clones which produce the antibody is established. The monoclonal antibody can then be purified by affinity chromatography using Protein A Sepharose, ion-exchange chromatography, as well as variations and combinations of these techniques. Truncated versions of monoclonal antibodies may also be produced by recombinant techniques in which plasmids are generated which express the desired monoclonal antibody fragment in a suitable host.

In a further embodiment, a cell line is provided which secretes an antibody specific for an SBDS protein or a portion thereof; a cell line secreting an antibody specific for a human SBDS protein is preferred.

Diagnosis of Predisposition to AML

A number of SDS patients have been found to develop AML. It is of some concern that individuals who have survived into adulthood without being diagnosed as SDS sufferers, because of minimal or unrecognised symptoms, may nevertheless also be at risk for the development of AML. The present invention permits the identification of these individuals as SDS sufferers, so that they may be monitored for early signs of AML and appropriately treated. Although widespread screening of the population may not be practical, screening of relatives of diagnosed SDS patients for SDS-associated mutations is completely feasible, as also would be screening individuals exhibiting early or more overt signs of bone marrow transformation.

In addition, SDS carriers, who have an SDS-associated mutation in only one allele of the SBDS gene and are therefore asymptomatic, may be at risk for AML if they should experience loss or mutation of the wild-type allele, particularly in haematological tissues. Again, screening of family members in SDS-affected families will indicate such genetic changes.

Kits

The invention further provides kits for use in the diagnostic methods described above for determining whether a subject is suffering from or is at risk for SDS, for determining whether a subject is a carrier of SDS or for determining whether a subject is at risk for AML. Such kits can comprise, for example, one or more pairs of oligonucleotide primers suitable for amplification of the SBDS gene or portions thereof, such as primers suitable for amplification of particular exons of SBDS, particularly human SBDS, as described for example in FIG. 6. such kits can also contain instructions for use of the primers, and optionally, additional reagents required for the diagnostic methods described herein.

Therapeutic Methods

The invention further provides methods and compositions for treating subjects, including humans, suffering from SDS.

Methods of treatment are directed to restoring normal SBDS function in the subject.

Such methods include gene therapy to restore normal function at the gene level and administration of normal SBDS protein or portions thereof to make up for lack of normal gene expression.

Gene therapy may, for example, involve administration to the subject of a construct comprising an expression vector containing a nucleotide sequence encoding a wild type SBDS protein. Suitable expression vectors include retroviral, adenoviral and vaccinia virus vectors. Administration may be intravenous, oral, subcutaneous, intramuscular or intraperitoneal.

A large number of gene delivery methods are well known to those of skill in the art and may include, for example liposome-based gene delivery (Debs and Zhu (1993) WO 93/24640; Mannino and Gould-Fogerite (1988) BioTechniques 6(7): 682-691; Rose U.S. Pat. No. 5,279,833; Brigham (1991) WO 91/06309; and Felgner et al. (1987) Proc. Natl. Acad Sci. USA 84: 7413-7414), and replication-defective retroviral vectors harboring a therapeutic polynucleotide sequence as part of the retroviral genome (see, e.g., Miller et al. (1990) Mol. Cell. Biol. 10:4239 (1990); Kolberg (1992) J. NIH Res. 4:43, and Cornetta et al. Hum. Gene Ther. 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) J. Virol. 66(5) 2731-2739; Johann et al. (1992) J. Virol. 66 (5):1635-1640 (1992); Sommerfelt et al., (1990) Virol. 176:58-59; Wilson et al. (1989) J. Virol. 63:2374-2378; Miller et al., J. Virol. 65:2220-2224 (1991); Wong-Staal et al., PCT/US94/05700, and Rosenburg and Fauci (1993) in Fundamental Immunology, Third Edition Paul (ed) Raven Press, Ltd., New York and the references therein, and Yu et al., Gene Therapy (1994) supra).

AAV-based vectors are also used to transduce cells with target nucleic acids, e.g., in the in vitro production of nucleic acids and peptides, and in the in vivo and ex vivo gene therapy procedures. See, West et al. (1987) Virology 160:38-47; Carter et al. (1989) U.S. Pat. No. 4,797,368; Carter et al. WO 93/24641 (1993); Kotin (1994) Human Gene Therapy 5:793-801; Muzyczka (1994) J. Clin. Invest. 94:1351 and Samulski (supra) for an overview of MV vectors. Construction of recombinant MV vectors are described in a number of publications, including Lebkowski, U.S. Pat. No. 5,173,414; Tratschin et al. (1985) Mol. Cell. Biol. 5(11):3251-3260; Tratschin, et al. (1984) Mol. Cell. Biol. 4:2072-2081; Hermonat and Muzyczka (1984) Proc. Natl. Acad. Sci. USA 81:6466-6470; McLaughlin et al. (1988) and Samulski et al. (1989) J. Virol. 63:03822-3828. Cell lines that can be transformed by rAAV include those described in Lebkowski et al. (1988) Mol. Cell. Biol. 8: 3988-3996.

The organ with the most serious life threatening consequences, the bone marrow, may be treated by ex vivo gene therapy. This would involve the 1) extraction of bone marrow cells, 2) introduction of cDNA without mutations in conjunction with expression guiding elements followed by 3) reintroduction of these modified cells back to the bone marrow. Similar strategies have been used successfully in other diseases including severe combined immunodeficiency-X1 (M Cavazzana-Calvo, S Halcein-Bey, G de Saint Basile, F Gross, E Yvon, P Nusbaum, F Selz, C Hue, S Certain, J-L Casanova, P Bousso, F Le Deist and A Fischer. (2000) Gene therapy of human severe combined immunodefiency (SCID)-X1 disease. *Science* 288: 669-672; all of which are incorporated herein by reference). The SBDS gene is notably small such that native gene expression may be achieved with the incorporation of natural promoter and enhancer gene elements.

The SBDS nucleotide sequences described herein may be used in conventional expression systems, as described herein, to permit production of depechin protein in amounts sufficient for antibody production or for therapy.

Therapeutic compositions in accordance with the invention comprise an isolated nucleotide sequence encoding an SBDS protein or effective fragment thereof or a substantially purified SBDS protein or effective fragment thereof.

Transgenic Animal Models of SDS

The invention further enables the creation of an animal model of SDS which is important for further study of how SBDS mutations lead to the various SDS-associated disease manifestations and for testing of potential therapeutics. A number of non-human mammals may be used to create such a model, including without limitation mice, rats, rabbits, sheep, goats and non-human primates. An animal model of SDS may have within its genome one or both SBDS genes with at least one mutation which when expressed results in symptoms of SDS. Identification and sequencing of the mouse SBDS gene homologue, as described herein, facilitates the creation of such animal models, for example a mouse model.

Methods for the creation of transgenic animals are well known to those of skill in the art. A transgenic animal according to the invention is an animal having cells that contain a transgene which was introduced into the animal or an ancestor of the animal at a prenatal (embryonic) stage. A transgenic animal can be created, for example, by introducing the gene of interest into the male pronucleus of a fertilised oocyte by, e.g., microinjection, and allowing the oocyte to develop in a pseudopregnant female foster animal. The gene of interest may include appropriate promoter sequences, as well as intronic sequences and polyadenylation signal sequences.

Methods for producing transgenic animals are disclosed in, e.g., U.S. Pat. Nos. 4,736,866 and 4,870,009 and Hogan et al., A Laboratory Manual, Cold Spring Harbor Laboratory, 1986. A transgenic founder animal can be used to breed additional animals carrying the transgene. A transgenic animal carrying one transgene can also be bred to another transgenic animal carrying a second transgene to create a "double transgenic" animal carrying two transgenes. Alternatively, two transgenes can be co-microinjected to produce a double transgenic animal. Animals carrying more than two transgenes are also possible. Furthermore, heterozygous transgenic animals, i.e., animals carrying one copy of a transgene, can be bred to a second animal heterozygous for the same transgene to produce homozygous animals carrying two copies of the transgene. For a review of techniques that can be used to generate and assess transgenic animals, skilled artisans can consult Gordon (Intl. Rev. Cytol., 115:171-229 (1989)), and may obtain additional guidance from, for example: Hogan et al, Manipulating the Mouse Embryo (Cold Spring Harbor Press, Cold Spring Harbor, N.Y. 1986); Krimpenfort et al., Bio/Technology, 9:844-847 (1991); Palmiter et al., Cell, 41:343-345 (1985); Kraemer et al., Genetic Manipulation of the Early Mammalian Embryo (Cold Spring Harbor Press, Cold Spring Harbor, N.Y. 1985); Hammer et al., Nature, 315:680-683 (1985); Purscel et al., Science, 244:1281-1288 (1986); Wagner et al., U.S. Pat. No. 5,175,385; and Krimpenfort et al., U.S. Pat. No. 5,175,384.

EXAMPLES

The examples are described for the purposes of illustration and are not intended to limit the scope of the invention.

Methods of molecular biology, genetics, protein and peptide biochemistry and immunology referred to but not explicitly described in this disclosure and examples are reported in the scientific literature and are well known to those skilled in the art.

Methods

Human Subjects. Families with SDS included in this study have been described, and additional families have been obtained through ongoing recruitment[2]. The criterion for inclusion in the study was the presence of both exocrine pancreatic dysfunction and hematologic abnormalities, including neutropenia and other problems associated with bone marrow failure. Consent was obtained from all participating families, and procedural approval was obtained from the human subjects review board of The Hospital for Sick Children, Toronto (HSC). Genomic DNA was extracted either from Epstein-Barr virus (EBV) transformed B-lymphoblastoid cell lines or directly from peripheral white blood cell pellets, as described by Miller et al.[24]. Patient and control RNA was extracted from EBV-transformed B-lymphoblastoid cell lines as previously described[25]. DNA from 100 control Caucasian individuals (Human variation panel HD100CAU) was purchased from Coriell Cell Repositories (Camden, N.J.).

Physical Mapping. Genomic sequences were identified through BLAST analysis of STSs and genetic markers in the SDS critical interval against the GenBank non-redundant (nr) and high throughput genome sequence (htgs) databases[26]. Where the density of pre-existing markers was low, BAC and YAC clones assigned to the region were subcloned and sequenced to provide new STSs as described[5]. Genomic sequences were compiled manually and the framework was supported by radiation hybrid mapping of select STSs.

Candidate Gene Identification. Candidate genes were identified in genomic sequences through the use of annotation data provided by GenBank (http://www.ncbi.nlm.nih.gov) and Project Ensembl (http://www.ensembl.org)[26,27]. Ab initio gene predictions were obtained through the use of GeneScript. Human genomic sequences were also compared to mouse genomic sequences (available through Celera Discovery System and Celera Genomics' associated databases) from the syntenic interval on mouse chromosome 5 using PipMaker2 to identify regions of cross-species conservation[28]. All in silico gene predictions were confirmed by RT-PCR analysis using random-primed cDNA derived from fetal brain, and/or testes poly(A)+ mRNA (Clontech, Palo Alto, Calif.).

Mutation Detection. The genomic structure of the SBDS gene and its pseudogene copy were used to design primer pairs using Primer3 to screen coding regions[29]. The position of primer pairs is shown (FIGS. 1 and 6). PCR products were directly sequenced or cloned using a Topo TA-cloning kit (Clontech) prior to sequencing. Primer pairs (specific for SBDS unless otherwise stated) used were: A (5'-GCGTAAAAAGCCACAATAC-3': SEQ ID NO:3) and B (5'-CTATGACAGTATTCGTAAGACTAGG-3': SEQ ID NO:4) (exon 1), C (5'-GGGGATTTGTTGTGTCTTG-3': SEQ ID NO:5) and D (5'-CTTTCCTCCAGAAAAACAGC-3': SEQ ID NO:6) (exon 2, SBDS/SBDSP dual-specific), E (5'-AAATGGTAAGGCAAATACGG-3': SEQ ID NO:7) and F (5'-ACCAAGTTCTTTATTATTAGAAGTGAC-3': SEQ ID NO:8) (exon 2), G (5'-GCTCAAACCATTACTTACATATTGA-3': SEQ ID NO:9) and H (5'-CACTTGCTTCCATGCAGA-3': SEQ ID NO:10) (exon 3), I (5'-AAAGGGTCATTTTAACACTTC-3': SEQ ID NO:11) and J (5'-GAAAATATCTGACGTTTACAACA-3': SEQ ID NO:12) (exon 4), K (5'-TCCACTGTAGATGTGAACTAACTC-3': SEQ ID NO:13) and L (5'-CACTCTGGACTTTGCATCTT-3': SEQ ID NO:14) (exon 5), M (5'-GCTTCTGCTCCACCTGAC-3': SEQ ID NO:15) and N (5'AGCTATGCTGCAGCTGTTAC-3': SEQ ID NO:16) (exons 1 & 2, SBDS/SBDSP dual-specific), O (5'-ATGCATGTCCAAGTTTCAAG-3': SEQ ID NO:17) and P (5'-TCCATGGCTATATTTTGATGA-3': SEQ ID NO:18) (exons 2 & 3, SBDS/SBDSP dual-specific). Patients were also screened for mutations through sequencing of RT-PCR products from random-primed cDNA derived from patient EBV-transformed B-lymphoblastoid cell lines. Primers used were: Q (5'-TAAGCCTGCCAGACACAC-3' SEQ ID NO:19) and R (5'-CACTCTGGACTTTGCATCTT-3' SEQ ID NO:20) (yields full length SBDS open reading frame), Q and S (5'-TGTTGGTTTTCACCGAATA-3' SEQ ID NO:21), and T (5'-AGATAAAGAAAGACACACACAACT-3' SEQ ID NO:22) and R. Gene conversion mutations were detected through restriction analysis of exon 2 PCR fragments. Exon 2 was amplified from patient DNA using PCR primers C & D or E & F, and purified using a MinElute PCR Cleanup Kit (Qiagen). Restriction digestion using DdeI (not shown) or Bsu036I ([183TA>CT]) and Cac8I ([258+2T>C]) (New England Biolabs, Beverly, Mass.) was carried out as recommended by the manufacturer and analyzed by agarose gel electrophoresis. For all mutations, allele-specific oligonucleotide hybridisation to amplified SBDS exons from control individuals was carried out as described[30].

The common mutations that account for the majority of SDS alleles can be detected by PCR and restriction enzyme digestions by Bsu36I and Cac8I. These digestions can be performed singly or in combination.

PCR Amplification

```
Primer E:
5'-AAATGGTAAGGCAAATACGG-3'          (SEQ ID NO: 7)

Primer F:
5'-ACCAAGTTCTTTATTATTAGAAGTGAC-3'   (SEQ ID NO: 8)
``` product size: 733 bp; annealing temperature: 56.6° C.; extension time: 40 sec

Double Digestion
  Bsu36I (New England Biolabs #R0524): 6 units plus
  Cac8I (New England Biolabs #R0579): 4.8 units per 100-200 ng PCR product. Digest at 37° C.>3 hr Band Sizes Detected on Agarose Gel with Ethidium Bromide Intercalation
  Normal: 584 bp also 64 bp, 41 bp, and smaller bands
  258+2 T>C: 431 bp and 153 bp also 64 bp, 41 bp and smaller bands
  183 TA>CT: 358 bp and 226 bp also 64 bp, 41 bp and smaller bands
  258+2T>C+183TA>CT: 358 bp, 153 bp, 73 bp also 64 bp, 41 bp and smaller bands DdeI should not be used for this double digest; Bsu36I and Cac8I should be used for this version of the assay.

Dual Specific Digests for Common Mutations

PCR Amplification

```
Forward Primer:
5'-GGGGATTTGTTGTGTCTT-3'    (SEQ ID NO: 5)

Reverse Primer:
5'-CTTTCCTCCAGAAAAACAGC-3'  (SEQ ID NO: 6)
``` product size: 336 bp; annealing temperature: 56° C.; extension time: 1 min.

Cac8I Digest
  Cac8I (NEB #R0579): 4.8 units; digest at 37° C.>3 hr

Band Size: Normal: 2×336 bp, 2×241 bp, 2×95 bp; 1 allele with 258+2 T>C: 1×336 bp, 3×241 bp, 3×95 bp; 2 alleles with 258+2 T>C: 4×241 bp, 4×95 bp.

Dde I Digest
  Dde I (NEB #R0175): 6 units; digest at 37° C. 2 hr

Band Size: Normal: 2×190 bp, 2×169 bp, 4×146 bp, 2×21 bp; 1 allele with 183 TA>CT: 1×190 bp, 3×169 bp, 4×146 bp, 2×21 bp; 2 alleles with 183 TA>CT: 4×169 bp, 4×146 bp, 2×21 bp.

Southern Hybridisation. Genomic DNA from patients and control individuals was subjected to restriction digestion with NdeI (New England Biolabs) as recommended by the manufacturer and products were separated by agarose gel electrophoresis. The DNA was blotted and hybridised with a radiolabeled SBDS partial cDNA probe (exons 1-3) as described[30].

RT-PCR and RNA Blot Analysis. A panel of cDNAs derived from 22 adult and fetal tissues (Clontech) were analyzed by RT-PCR according the supplier's recommendations. Primers used were T and R (SBDS), and (5'-TAAGTAAGCCTGCCAGACA-3' SEQ ID NO:25) and (5'-CATCAAGGTCTTTTTCCAAG-3' SEQ ID NO:26) (SBDSP). Primers used to assess the relative amount of SBDS exon 2 alternative splicing were U (5'-GAAATCGCCTGCTACAAA-3' SEQ ID NO:23) and V (5'-TCAGCTTCTTGCCTTCAT-3' SEQ ID NO:24). RNA blots of poly(A)+ mRNA (Clontech) were hybridized to DNA probes labeled with [$\alpha^{32}$P]-dCTP[30]. The SBDS probe was a cloned RT-PCR fragment (primers Q and R). The intron 1 probe was PCR amplified from genomic DNA using primers (5'-CCTGTCTCTGCCCAAGTC-3' SEQ ID NO:27) and (5'-AGGGAACATTTTCAAAACTCA-3' SEQ ID NO:28).

Sequence Alignment and Analysis. SBDS orthologues were identified through BLASTP analysis of amino acid sequences in the GenBank nr database, and through TBLASTN analysis of the GenBank EST database (dbEST). Sequences were aligned with CLUSTALX using default parameters followed by manual adjustment[31]. Amino acids were analysed for the presence of functional motifs using Pfam and associated databases (http://www.sanger.ac.uk/Software/Pfam/)[21].

Genbank Accession Numbers. SBDS consensus cDNA, AY169963 cDNA flj10917, AK001779; SDCR2A (cDNA flj10900), AK001762; SDCR3 (cDNA flj10099), AK000961; BAC RP11-458F8, AC073335; BAC RP11-325K1, AC079920; BAC RP11-584N20, AC069291; BAC RP11-324F21, AC073089; BAC RP11-16604, AC006480; BAC RP11-479C13, AC005236. Depechin orthologues: *Arabidopsis thaliana* At1 g43860 gene product, NP_564488; *Drosophila melanogaster* CG8549 gene product, NP_648057; *Caenorhabditis elegans* protein W06E11.4.p, NP_497226; *Mus musculus* protein 22A3, P70122; *Oryzias latipes* amino acid sequence derived from cDNA clone MF01SSA157A09 5' and 3' overlapping sequence reads, BJ013200 and BJ025159; *Saccharomyces cerevisiae* Ylr022cp, NP_013122; *Encephalitozoon cuniculi* ECU08_1610 gene product, NP_597289; *Methanosarcina acetivorans* str. C2A MA1778 gene product, NP_616704; *Halobacterium* sp. NRC-1 Vng1276c, NP_280149; *Methanopyrus kandleri* str. AV19 MK0384 gene product, NP_613669; *Methanococcus jannaschii* MJ0592 gene product, NP_247572; *Archaeoglobus fulgidus* AF0491 gene product, NP_069327; *Pyrococcus abyssi* PAB0418 gene product NP_126299; *Thermoplasma acidophilum* Ta1291m gene product, NP_394745; *Pyrobaculum aerophilum* PAE2209 gene product, NP_559847; *Sulfolobus solfataricus* SSO0737 gene product, NP_342243; *Aeropyrum pernix* APE1167 gene product, NP_147753; *Populus balsamifera* subsp. *Trichocarpa* amino acid sequence derived from cDNA clone F038P45Y, BI121507; *Gossypium arboreum* amino acid sequence derived from cDNA clone GA_Ed0050B07f, BQ402534.

Example 1

Figure 2:
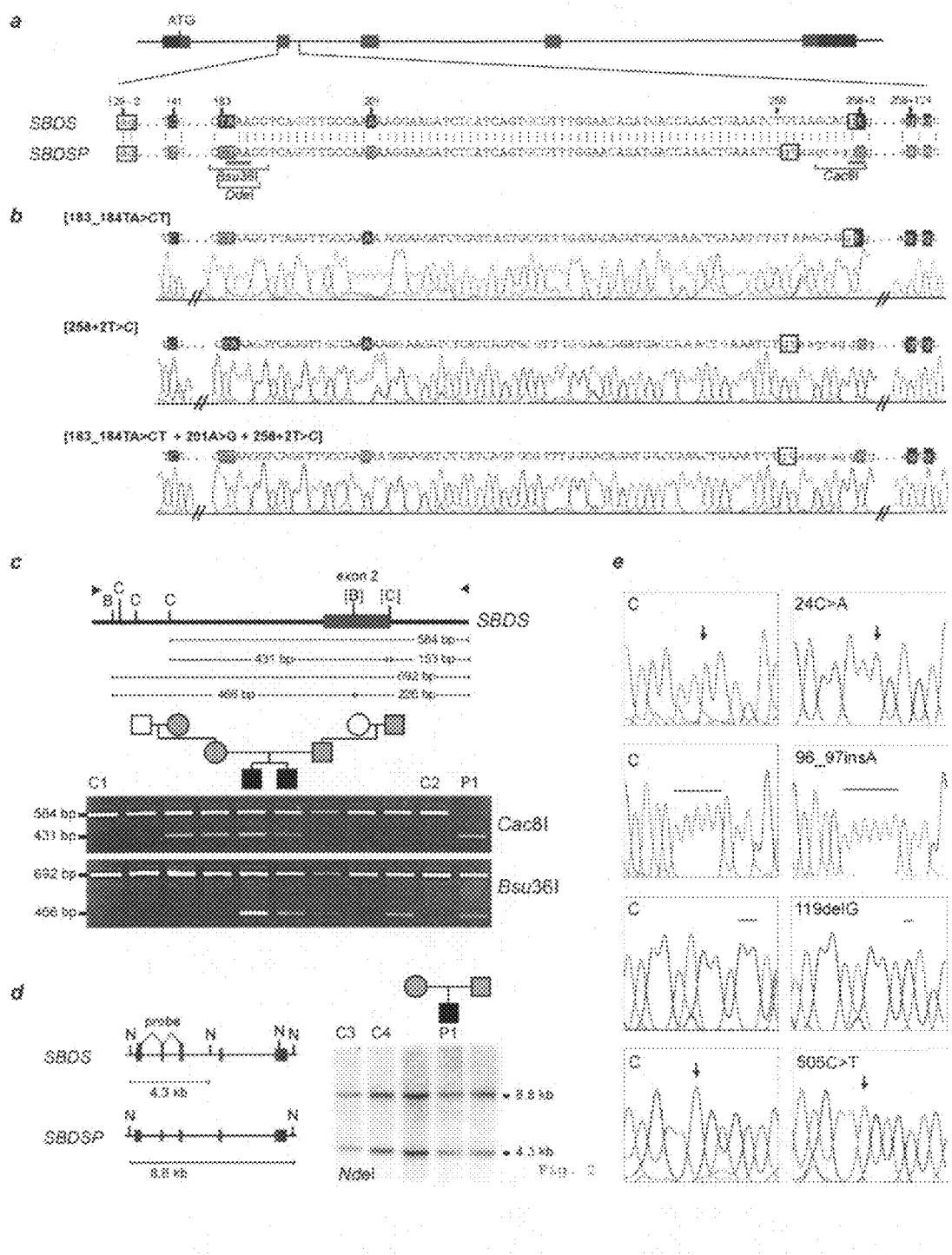
FIG. 2 shows mutations in SBDS associated with SDS. a, Map of SBDS (coding regions in light blue) and sequence alignment of the exon 2 region of SBDS and SBDSP, with gene-specific sequences in green and pseudogene sequences in red. In comparison to SBDS, SBDSP exon 2 contains sequence changes (underlined in red) that are predicted to result in truncation of its predicted protein product. These include an in-frame stop codon at 184 bp and a T>C change at 250+10 bp (corresponding to the invariant T of the donor splice site at 258+2 bp in SBDS) which results in the use of an alternate donor splice site (invariant splice site positions are boxed) at 250+1 bp. The sequence differences in SBDSP present restriction sites for Bsu36I, and DdeI at 183 bp and Cac8I at 240+7 bp. b, Electropherograms for cloned sequences from the exon 2 region of SBDS reveal sequence changes (red) derived from gene conversion events between SBDS and its pseudogene; three gene converted alleles are shown. These include [183TA>CT], [258+2T>C], and an extended conversion mutation [183TA>CT+201A>G+258+2T>C] with the intervening adenine (position 201) to guanine change. In each case, flanking sequences, including those at 129-2 bp and 258+124 bp, have not been converted (green). c, A restriction map of the SBDS exon 2 amplimer (primers E and F, FIG. 1d) showing the position of Cac8I (C) and Bsu36I (B) restriction sites. Square brackets indicate the positions of restriction sites corresponding to converted sequences. The pedigree of family SW20 is shown with affected individuals in black and carriers in grey. Restriction fragment analysis of PCR amplified SBDS exon 2 sequences revealed that the brothers inherited [183TA>CT] through the father and paternal grandfather, and [258+2T>C] through the mother and maternal grandmother. Patient P1 is heterozygous for [258+2T>C] and the extended conversion mutation ([183TA>CT+201A>G+258+2T>C]). Two unrelated control individuals are also shown (C1 and C2). d, Restriction maps of the gene and pseudogene loci showing the locations of all NdeI restriction sites (N). Hybridisation of a DNA probe derived from a partial SBDS cDNA (green) to genomic DNAs restriction digested with NdeI indicates that members of family SW6 (including patient P1 with two converted alleles) show a pattern of hybridisation similar to two unrelated control individuals (C3 and C4) indicating that no rearrangements or deletions have occurred in the vicinity of SBDS or SBDSP. e, Sequence traces depicting other representative coding mutations in patient SBDS compared to controls (N), including an insertion ([96_97insA]), a deletion ([119delG]) and two missense mutations ([24C>A] and [505C>T]).

RT-PCR analysis of several SDS patients with SBDS-specific oligonucleotide primers (indicated as RT-PCR primers Q and R in FIG. 1a and described in FIG. 6) revealed recurring sequence changes in exon 2, including a TA>CT dinucleotide change at position 183 or an 8 bp deletion at the end of the exon (the nucleotide numbering is described in FIGS. 5 and 6). Analysis of SBDS genomic sequences confirmed the presence of the [183TA>CT] sequence change and revealed a [258+2T>C] nucleotide change in patients expressing the deleted SBDS transcript. [258+2T>C] is predicted to disrupt the donor splice site of intron 2, and the 8 bp deletion observed in the transcript is consistent with use of an upstream cryptic splice donor site at position 251. Alignment of patient SBDS sequences to genomic sequences from GenBank and control individuals indicated that both changes corresponded to sequences normally present in SBDSP (FIG. 2a, b). The dinucleotide alteration [183TA>CT] introduces an in-frame stop codon (K62X) while [258+2T>C] and its resultant 8 bp deletion also causes premature truncation of the encoded protein by frameshift (84Cfs3). Patient alleles were also identified that contain both of these changes together with an additional silent nucleotide change ([201A>G]) in the intervening segment, again consistent with the pseudogene sequence (FIG. 2b). The [183TA>CT] and [258+2T>C] changes could be detected in amplified SBDS genomic DNA followed by restriction digestion with Bsu36I and Cac8I, respectively (FIG. 2a, c). Analysis of SDS pedigrees revealed that these changes were inherited and disease-associated. An example of segregating alleles in a linked pedigree is shown in FIG. 2c. The specificity of genomic DNA amplimers for SBDS was supported by the absence of additional pseudogene-like sequence changes in nucleotide positions flanking the 183 and 258+2 bp positions (FIG. 2b) and the absence of any SBDSP-like sequences in 100 control samples. These findings, together with the observation of unaltered hybridisation patterns of genomic DNA with a SBDS probe (FIG. 2d), indicated that gene conversion due to recombination between SBDS and its highly homologous pseudogene had occurred. A similar basis for mutation has been observed in other genetic diseases[7-19]. Sequence analysis of the exon 2 region of patients indicated that most conversion events are confined to a short segment between 141 bp and 258+124 bp with a maximum size of 240 bp (FIG. 2a, b). Based on restriction digestion or sequencing of PCR products of patients from 158 unrelated families, 74% of SDS alleles (n=235 of 316) are the result of gene conversion, with 89% of patients carrying at least one converted allele and 60% carrying two converted alleles. Consistent with being a recessive disease, patients carry mutations on both copies of the SBDS gene. Of the patients analysed in the initial study, 50% were [183TA>CT]+[258+2T>C] compound heterozygotes, 5.1% were [183TA>CT+258+2T>C]+[258+2T>C] compound heterozygotes, and 4.4% were homozygous for a [258+2T>C] conversion. Of patient alleles not displaying the conversion mutations, genomic sequencing revealed other changes within the coding region of SBDS, including small deletions, insertions, and nucleotide substitutions that would lead to frameshift and premature truncation, missense and nonsense changes (Table 1 and FIG. 4). To date, these mutations were not detected in 100 Caucasian control DNA samples by allele specific oligonucleotide hybridization or correspond to changes of highly conserved amino acids that would not be expected to be important for protein structure or function. Table 1 shows the SDS-associated mutations identified in the initial study and in subsequent studies.

Example 2

RNA hybridisation with SBDS indicated broad expression of a 1.6 kb message (FIG. 3a). Numerous GenBank EST clones, however, indicated that the pseudogene is also transcribed. Prominent larger-sized transcripts were also observed in poly(A)+ mRNA from several tissues and were confirmed to include intron 1 through hybridisation of an intron 1-specific probe (FIG. 3a). In addition, three GenBank EST clones corresponding to SBDSP were found to contain intron 1.

RNA expression analysis was carried out on a number of normal adult or fetal tissues, and on lymphoblasts from a number of SDS patients. As seen from FIG. 3b, the level of combined SBDS/SBDSP mRNA, and consequently of protein product, was notably reduced in patient samples, compared with control C, lymphoblast RNA from a healthy subject.

Distinction between expression of the gene and pseudogene could be obtained through RT-PCR with specific oligonucleotide primers (FIG. 3c). Further, a broad survey of tissues revealed that the majority of SBDS mRNA does contain exon 2 although its alternative splicing was prominent in some patients (FIG. 3c and data not shown). Both RT-PCR and RNA analyses supported widespread expression of SBDS in all tissues examined, including the most disease-relevant tissues, pancreas, bone marrow, and myeloid lineages (FIG. 3a, c).

Example 3

Generation of Antibodies for SBDS Protein Detection

Two methods were used to generate specific antibody probes to detect SBDS protein cells and tissues. First, a bacterially expressed polypeptide with the entire open reading frame of SBDS and, second, specified peptides synthesised from the amino and carboxyl portion (see legend to FIG. 7), were used as immunogens in rabbits. To obtain high level expression of recombinant SBDS, the complete open reading frame of the SBDS gene was incorporated into the pET28a vector (Novagen) using standard molecular biology techniques (Ref. 30). The open reading frame was fused with the (HIS)6 tag of the expression vector for purification with immobilised metal (Ni2+) affinity chromatography. The purified polypeptide was then conjugated and injected into rabbits with the services of Washington Biotechnology, Inc. Pre-immune and immune sera were collected and whole cell protein extracts of various cell types were assessed, FIG. 7. The amino and carboxyl peptide antibodies were synthesised and prepared with the services of AnaSpec, Inc. and Washington Biotechnology, Inc., respectively. The antibodies showed high affinity and specificity for the SBDS protein product in different organs and cell lines, by Western blotting carried out as follows.

Whole cell extracts were prepared with Laemmli (*E. coli*) or RIPA (mammalian cells) buffer (and separated by 13.5% PAGE prior to blotting on Hybond C Extra (Amersham) membrane (Ref. 30 and Harlow and Lane). For rSBDS and anti-CpSBDS anti-sera, the membrane was blocked with 7% skim milk in TBST (10 mM Tris HCl, pH7.3, 100 mM NaCl with 0.1% Tween 20) for overnight at room temperature followed by incubation of a 1:2000 dilution for 5 h at room temperature. The blot was washed with TBST for five consecutive washes and incubated with anti-rabbit secondary antibody (Stressgen Biotechnologies Corp). The anti-Myc (Oncogene Research Products) and anti-HA (BAbCO-Covance) monoclonal antibodies and the anti-mouse secondary antibodies (Jackson ImmunoResearch Labs, Inc.) were used as recommended by their suppliers. The immunoreactive bands were detected by enhanced chemiluminescence.

TABLE 1

SDS-associated mutations

| Nucleotide Sequence Changes | Predicted Amino Acid Change |
|---|---|
| 183_184TA→CT | K62X |
| 183_184TA→CT + 258 + 2T→C | K62X |
| 258 + 2T→C | 84Cfs3 |
| 24C→A | N8K |
| 96–97insA | N34fs15 |
| 119delG | S41fs17 |
| 131A→G | E44G |
| 199A→G | K67E |
| 258 + 1G→C | 84Cfs3 |
| 260T→G | I87S |
| 291–293delTAAinsAGTTCAAGTATC | D97–K98delinsEVQVS |
| 377G→C | R126T |
| 505C→T | R169C |
| 56G→A | R19Q |
| 93C→G | C31W |
| 97A→G | K33E |
| 101A→T | N34I |
| 123delC | S41fs17 |
| 279_284delTCAAGT | Q94_V95del |
| 296_299delAAAG | E99fs20 |
| 354A→C | K118N |
| 428C→T + 443A→G | S143L + K148R |
| 458A→G | Q153R |
| 460 – 1G→A | splice |
| 506G→T | R169L |
| 624 + 1G→C | splice |

TABLE 2

SBDS Polymorphisms
Some sequence changes in SBDS are predicted to be silent polymorphisms. Although some of these changes were detected in SDS patients, allele-specific oligonucleotide hybridisation was used to screen control samples to determine that these changes are not disease associated and should be classified as silent polymorphisms.

| Nucleotide Sequence Change | Predicted Amino Acid Change |
|---|---|
| Intron 1 | |
| 129 – 71G→A | |
| 129 – 185G→A | |
| 129 – 225C→G | |
| 129 – 265G→A | |
| Intron 2 | |
| 258 + 19A→G | |
| 258 + 54T→G | |
| 258 + 99A→C | |
| Intron 3 | |
| 459 + 92A→G | |
| Exon 2 | |
| 141C→T | L47L |
| 201A→G | K67K |
| Exon 5 | |
| 651C→T | F217F |
| 635T→C | I212T |
| Rare Change | |
| 210T→C | D70E |

REFERENCES

1. Shwachman, H, Diamond, L. K. & Khaw, K. The syndrome of pancreatic insufficiency and bone marrow dysfunction. *J. Pediatr.* 65, 645-63 (1964).
2. Ginzberg, H. et al. Shwachman syndrome: Phenotypic manifestations of sibling sets and isolated cases in a large patient cohort are similar. *J. Pediatr.* 135, 81-88 (1999).
3. Ginzberg, H. et al. Segregation analysis in Shwachman-Diamond syndrome: Evidence for Recessive Inhertiance. *Am. J. Hum. Genet.* 66, 1413-1416 (2000).

4. Goobie, S. et al. Shwachman-Diamond syndrome with exocrine pancreatic dysfunction and bone marrow failure maps to the meric region of chromosome 7. *Am. J. Hum. Genet.* 68, 1048-1054 (2001).
5. Popovic, M. et al. Fine mapping of the locus for Shwachman-Diamond syndrome at 7q11, identification of shared disease haplotypes, and exclusion of TPST1 as a candidate gene. *Eur. J. Hum. Genet.* 10, 250-8 (2002).
6. Koonin, E. V., Wolf, Y. I. & Aravind, L. Prediction of the archaeal exosome and its connections with the proteasome and the translation and transcription machineries by a comparative-genomic approach. *Genome Res.* 11, 240-252 (2001).
7. Roesler, J. et al. Recombination events between the p47-phox gene and its highly homologous pseudogenes are the main cause of autosomal recessive chronic granulomatous disease. *Blood.* 15, 2150-2156 (2000).
8. T. Strachan. Molecular pathology of 21-hydroxylase deficiency. *J. Inherit. Metab. Dis.* 17, 430-41 (1994).
9. M. I. New. Steroid 21-hydroxylase deficiency (congenital adrenal hyperplasia). *Am. J. Med.* 98(1A), 2S-8S.
10. Beutler E. Gaucher disease as a paradigm of current issues regarding single gene mutations of humans. *Proc. Natl. Acad. Sci. USA.* 90, 5384-5390 (1993).
11. Eikenboom, J. C., Vink, T., Briet, E., Sixma, J. J., and P. H. Reitsma. Multiple substitutions in the von Willebrand factor gene that mimic the pseudogene sequence. *Proc. Natl. Acad. Sci. USA.* 91, 2221-2224 (1994).
12. Watnick, T. J., Gandolph, M. A., Weber, H., Neumann, H. P., and G. G. Germino. Gene conversion is a likely cause of mutation in PKD1. *Hum. Mol. Genet.* 7, 1239-1243 (1998).
13. Chen, J. M., and C. Ferec. Molecular basis of hereditary pancreatitis. *Eur. J. Hum. Genet.* 8, 473-479 (2000).
14. Chen, J. M., Raguenes, O., Ferec, C., Deprez, P. H., and C. Verellen-Dumoulin. A CGC>CAT gene conversion-like event resulting in the R122H mutation in the cationic trypsinogen gene and its implication in the genotyping of pancreatitis. *J. Med. Genet.* 37, E36 (2000).
15. Cai, L. et al. A novel Q378X mutation exists in the transmembrane transporter protein ABCC6 and its pseudogene: implications for mutation analysis in pseudoxanthoma elasticum. *J. Mol. Med.* 79, 536-546 (2001).
16. Bunge, S., et al. Homologous nonallelic recombinations between the iduronate-sulfatase gene and pseudogene cause various intragenic deletions and inversions in patients with mucopolysaccharidosis type 11. *Eur. J. Hum. Genet.* 6, 492-500 (1998).
17. Hahnen, E., et al. Hybrid survival motor neuron genes in patients with autosomal recessive spinal muscular atrophy: new insights into molecular mechanisms responsible for the disease. *Am. J. Hum. Genet* 59, 1057-1065 (1996).
18. Campbell, L., Potter, A., Ignatius, J., Dubowitz, V., and K. Davies. Genomic variation and gene conversion in spinal muscular atrophy: Implications for disease process and clinical phenotype. *Am. J. Hum. Genet.* 61, 40-50, (1997).
19. Wirth, B., et al. De novo rearrangements found in 2% of index patients with spinal muscular atrophy: Mutational mechanisms, parental origin, mutation rate, and implications for genetic counseling. *Am. J. Hum. Genet.* 61, 1102-1111 (1997).
20. Zhu, H. et al. Global analysis of protein activities using proteome chips. *Science.* 293, 2101-2105 (2001).
21. A. Bateman, et al. The Pfam Protein Families Database. *Nucl. Acids Res.* 30(1):276-280 (2002).
22. Winzeler, E. A., et al. Functional characterization of the *S. cerevisiae* genome by gene deletion and parallel analysis. *Science.* 285, 901-906 (1999).
23. Wu, L. F. et al. Large-scale prediction of *Saccharomyces cerevisiae* gene function using overlapping transcriptional clusters. *Nat. Genet.* 31, 255-265 (2002).
24. Miller, S. A., Dykes, D. D., & H. F. Polesky. A simple salting out procedure for extracting DNA from human nucleated cells. *Nucleic Acids Res.* 16, 1215 (1988).
25. MacDonald, R. J., Smith, G. H., Przybyla, A. E., and J. M. Chirgwin. Isolation of RNA using guanidinium salts. *Meth. Enzymol.* 152, 219-234 (1987).
26. Benson, D. A., Karsch-Mizrachi, I., Lipman, D. J., Ostell, J., Rapp, B. A., and D. L. Wheeler. GenBank. *Nucleic Acids Res.* 30, 17-20 (2002).
27. T. Hubbard et al. The Ensembl genome database. *Nucleic Acids Res.* 30, 38-41 (2002).
28. Schwartz et al. PipMaker—A Web Server for Aligning Two Genomic DNA Sequences *Genome Res.* 10, 577-586 (2000).
29. Rozen, S. and H. J. Skaletsky. Primer3 on the WWW for general users and for biologist programmers. In: Krawetz, S., and S. Misener. Bioinformatics Methods and Protocols: Methods in Molecular Biology. Humana Press, Totowa, N.J. (2000).
30. Sambrook, J. and D. W. Russell. Molecular Cloning. Cold Spring Harbor Laboratory Press, NY (2001).
31. Thompson, J. D., Gibson, T. J., Plewniak, F., Jeanmougin, F. and D. G. Higgins. The ClustalX windows interface: flexible strategies for multiple sequence alignment aided by quality analysis tools. *Nucleic Acids Res.* 24, 4876-4882 (1997).

SEQUENCE LISTING

```
<160> NUMBER OF SEQ ID NOS: 50

<210> SEQ ID NO 1
<211> LENGTH: 1604
<212> TYPE: DNA
<213> ORGANISM: Homo sapiens
<220> FEATURE:
<221> NAME/KEY: misc_feature
<223> OTHER INFORMATION: human SBDS
<220> FEATURE:
<221> NAME/KEY: CDS
<222> LOCATION: (185)..(934)
<223> OTHER INFORMATION:
```

<400> SEQUENCE: 1

```
gtaagtaagc ctgccagaca cactgtgacg gctgcctgaa gctagtgagt cgcggcgccg      60
cgcactggtg gttgggtcag tgccgcgcgc cgatcggtcg ttaccgcgag gcgctggtgg     120
ccttcaggct ggacggcgcg ggtcagccct ggttcgccgg cttctgggtc tttgaacagc     180 cgcg atg tcg atc ttc acc ccc acc aac cag atc cgc cta acc aat gtg     229
     Met Ser Ile Phe Thr Pro Thr Asn Gln Ile Arg Leu Thr Asn Val
     1               5                  10                  15 gcc gtg gta cgg atg aag cgt gcc ggg aag cgc ttc gaa atc gcc tgc     277
Ala Val Val Arg Met Lys Arg Ala Gly Lys Arg Phe Glu Ile Ala Cys
             20                  25                  30 tac aaa aac aag gtc gtc ggc tgg cgg agc ggc gtg gaa aaa gac ctc     325
Tyr Lys Asn Lys Val Val Gly Trp Arg Ser Gly Val Glu Lys Asp Leu
         35                  40                  45 gat gaa gtt ctg cag acc cac tca gtg ttt gta aat gtt tct aaa ggt     373
Asp Glu Val Leu Gln Thr His Ser Val Phe Val Asn Val Ser Lys Gly
     50                  55                  60 cag gtt gcc aaa aag gaa gat ctc atc agt gcg ttt gga aca gat gac     421
Gln Val Ala Lys Lys Glu Asp Leu Ile Ser Ala Phe Gly Thr Asp Asp
 65                  70                  75 caa act gaa atc tgt aag cag att ttg act aaa gga gaa gtt caa gta     469
Gln Thr Glu Ile Cys Lys Gln Ile Leu Thr Lys Gly Glu Val Gln Val
 80                  85                  90                  95 tca gat aaa gaa aga cac aca caa ctg gag cag atg ttt agg gac att     517
Ser Asp Lys Glu Arg His Thr Gln Leu Glu Gln Met Phe Arg Asp Ile
                 100                 105                 110 gca act att gtg gca gac aaa tgt gtg aat cct gaa aca aag aga cca     565
Ala Thr Ile Val Ala Asp Lys Cys Val Asn Pro Glu Thr Lys Arg Pro
             115                 120                 125 tac acc gtg atc ctt att gag aga gcc atg aag gac atc cac tat tcg     613
Tyr Thr Val Ile Leu Ile Glu Arg Ala Met Lys Asp Ile His Tyr Ser
         130                 135                 140 gtg aaa acc aac aag agt aca aaa cag cag gct ttg gaa gtg ata aag     661
Val Lys Thr Asn Lys Ser Thr Lys Gln Gln Ala Leu Glu Val Ile Lys
     145                 150                 155 cag tta aaa gag aaa atg aag ata gaa cgt gct cac atg agg ctt cgg     709
Gln Leu Lys Glu Lys Met Lys Ile Glu Arg Ala His Met Arg Leu Arg
160                 165                 170                 175 ttc atc ctt cca gtc aat gaa ggc aag agc ctg aaa gaa aag ctc aag     757
Phe Ile Leu Pro Val Asn Glu Gly Lys Ser Leu Lys Glu Lys Leu Lys
                 180                 185                 190 cca ctg atc aag gtc ata gaa agt gaa gat tat ggc caa cag tta gaa     805
Pro Leu Ile Lys Val Ile Glu Ser Glu Asp Tyr Gly Gln Gln Leu Glu
             195                 200                 205 atc gta tgt ctg att gac ccg ggc tgc ttc cga gaa att gat gag cta     853
Ile Val Cys Leu Ile Asp Pro Gly Cys Phe Arg Glu Ile Asp Glu Leu
         210                 215                 220 ata aaa aag gaa act aaa ggc aaa ggt tct ttg gaa gta ctc aat ctg     901
Ile Lys Lys Glu Thr Lys Gly Lys Gly Ser Leu Glu Val Leu Asn Leu
     225                 230                 235 aaa gat gta gaa gaa gga gat gag aaa ttt gaa tgacacccat caatctcttc     954
Lys Asp Val Glu Glu Gly Asp Glu Lys Phe Glu
240                 245                 250 acctctaaaa cactaaagtg tttccgtttc cgacggcact gtttcatgtc tgtggtctgc    1014
caaatacttg cttaaactat tgacattttt ctactttgtg ttaacagtgg acacagcaag    1074
gctttcctac ataagtataa taatgtggga atgatttggt tttaattata aactggggtc    1134
taaatcctaa agcaaaattg aaactccaag atgcaaagtc cagagtggca ttttgctact    1194
```

```
ctgtctcatg ccttgatagc tttccaaaat gaaagttact tgaggcagct cttgtgggtg    1254
aaaagttatt tgtacagtag agtaagatta ttaggggtat gtctatacaa caaaaggggg    1314
ggtctttcct aaaaaagaaa acatatgatg cttcatttct acttaatgga acttgtgttc    1374
tgagggtcat tatggtatcg taatgtaaag cttggatgat gttcctgatt atctgagaaa    1434
cagatataga aaaattgtgc cggacttacc tttcattgaa catgctgcca taacttagat    1494
tattcttggt taaaaaataa aagtcactta tttctaattc ttaaagttta taatatatat    1554
taatatagct aaaattgtat gtaatcaata aaaccactct tatgtttatt              1604
```

<210> SEQ ID NO 2
<211> LENGTH: 250
<212> TYPE: PRT
<213> ORGANISM: Homo sapiens
<220> FEATURE:
<221> NAME/KEY: misc_feature
<223> OTHER INFORMATION: human SBDS

<400> SEQUENCE: 2

```
Met Ser Ile Phe Thr Pro Thr Asn Gln Ile Arg Leu Thr Asn Val Ala
1               5                   10                  15

Val Val Arg Met Lys Arg Ala Gly Lys Arg Phe Glu Ile Ala Cys Tyr
                20                  25                  30

Lys Asn Lys Val Val Gly Trp Arg Ser Gly Val Glu Lys Asp Leu Asp
            35                  40                  45

Glu Val Leu Gln Thr His Ser Val Phe Val Asn Val Ser Lys Gly Gln
        50                  55                  60

Val Ala Lys Lys Glu Asp Leu Ile Ser Ala Phe Gly Thr Asp Asp Gln
65                  70                  75                  80

Thr Glu Ile Cys Lys Gln Ile Leu Thr Lys Gly Glu Val Gln Val Ser
                85                  90                  95

Asp Lys Glu Arg His Thr Gln Leu Glu Gln Met Phe Arg Asp Ile Ala
            100                 105                 110

Thr Ile Val Ala Asp Lys Cys Val Asn Pro Glu Thr Lys Arg Pro Tyr
        115                 120                 125

Thr Val Ile Leu Ile Glu Arg Ala Met Lys Asp Ile His Tyr Ser Val
    130                 135                 140

Lys Thr Asn Lys Ser Thr Lys Gln Gln Ala Leu Glu Val Ile Lys Gln
145                 150                 155                 160

Leu Lys Glu Lys Met Lys Ile Glu Arg Ala His Met Arg Leu Arg Phe
                165                 170                 175

Ile Leu Pro Val Asn Glu Gly Lys Lys Leu Lys Glu Lys Leu Lys Pro
            180                 185                 190

Leu Ile Lys Val Ile Glu Ser Glu Asp Tyr Gly Gln Gln Leu Glu Ile
        195                 200                 205

Val Cys Leu Ile Asp Pro Gly Cys Phe Arg Glu Ile Asp Glu Leu Ile
    210                 215                 220

Lys Lys Glu Thr Lys Gly Lys Gly Ser Leu Glu Val Leu Asn Leu Lys
225                 230                 235                 240

Asp Val Glu Glu Gly Asp Glu Lys Phe Glu
                245                 250
```

<210> SEQ ID NO 3
<211> LENGTH: 250
<212> TYPE: PRT
<213> ORGANISM: Homo sapiens

```
<220> FEATURE:
<221> NAME/KEY: misc_feature
<223> OTHER INFORMATION: human SBDS

<400> SEQUENCE: 3
```

| | | | | | | | | | | | | | | | |
|---|---|---|---|---|---|---|---|---|---|---|---|---|---|---|---|
| Met | Ser | Ile | Phe | Thr | Pro | Thr | Asn | Gln | Ile | Arg | Leu | Thr | Asn | Val | Ala |
| 1 | | | | 5 | | | | | 10 | | | | | 15 | |
| Val | Val | Arg | Met | Lys | Arg | Ala | Gly | Lys | Arg | Phe | Glu | Ile | Ala | Cys | Tyr |
| | | | 20 | | | | | 25 | | | | | 30 | | |
| Lys | Asn | Lys | Val | Val | Gly | Trp | Arg | Ser | Gly | Val | Glu | Lys | Asp | Leu | Asp |
| | | | 35 | | | | | 40 | | | | | 45 | | |
| Glu | Val | Leu | Gln | Thr | His | Ser | Val | Phe | Val | Asn | Val | Ser | Lys | Gly | Gln |
| 50 | | | | | 55 | | | | | 60 | | | | | |
| Val | Ala | Lys | Lys | Glu | Asp | Leu | Ile | Ser | Ala | Phe | Gly | Thr | Asp | Asp | Gln |
| 65 | | | | 70 | | | | | 75 | | | | | 80 | |
| Thr | Glu | Ile | Cys | Lys | Gln | Ile | Leu | Thr | Lys | Gly | Glu | Val | Gln | Val | Ser |
| | | | | 85 | | | | | 90 | | | | | 95 | |
| Asp | Lys | Glu | Arg | His | Thr | Gln | Leu | Glu | Gln | Met | Phe | Arg | Asp | Ile | Ala |
| | | | | 100 | | | | | 105 | | | | | 110 | |
| Thr | Ile | Val | Ala | Asp | Lys | Cys | Val | Asn | Pro | Glu | Thr | Lys | Arg | Pro | Tyr |
| | | | | 115 | | | | | 120 | | | | | 125 | |
| Thr | Val | Ile | Leu | Ile | Glu | Arg | Ala | Met | Lys | Asp | Ile | His | Tyr | Ser | Val |
| | | 130 | | | | | 135 | | | | | 140 | | | |
| Lys | Thr | Asn | Lys | Ser | Thr | Lys | Gln | Gln | Ala | Leu | Glu | Val | Ile | Lys | Gln |
| 145 | | | | | 150 | | | | | 155 | | | | | 160 |
| Leu | Lys | Glu | Lys | Met | Lys | Ile | Glu | Arg | Ala | His | Met | Arg | Leu | Arg | Phe |
| | | | | 165 | | | | | 170 | | | | | 175 | |
| Ile | Leu | Pro | Val | Asn | Glu | Gly | Lys | Lys | Leu | Lys | Glu | Lys | Leu | Lys | Pro |
| | | | | 180 | | | | | 185 | | | | | 190 | |
| Leu | Ile | Lys | Val | Ile | Glu | Ser | Glu | Asp | Tyr | Gly | Gln | Gln | Leu | Glu | Ile |
| | | | | 195 | | | | | 200 | | | | | 205 | |
| Val | Cys | Leu | Ile | Asp | Pro | Gly | Cys | Phe | Arg | Glu | Ile | Asp | Glu | Leu | Ile |
| | | 210 | | | | | 215 | | | | | 220 | | | |
| Lys | Lys | Glu | Thr | Lys | Gly | Lys | Gly | Ser | Leu | Glu | Val | Leu | Asn | Leu | Lys |
| 225 | | | | | 230 | | | | | 235 | | | | | 240 |
| Asp | Val | Glu | Glu | Gly | Asp | Glu | Lys | Phe | Glu | | | | | | |
| | | | | 245 | | | | | 250 | | | | | | |

```
<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
gcgtaaaaag ccacaatac                                                 19

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
ctatgacagt attcgtaaga ctagg                                          25
```

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6 gggatttgt tgtgtcttg                                                    19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ctttcctcca gaaaaacagc                                                  20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
aaatggtaag gcaaatacgg                                                  20

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
accaagttct ttattattag aagtgac                                          27

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
gctcaaacca ttacttacat attga                                            25

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
cacttgcttc catgcaga                                                    18

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
aaagggtcat tttaacactt c                                                    21

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
gaaaatatct gacgtttaca aca                                                  23

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
tccactgtag atgtgaacta actc                                                 24

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cactctggac tttgcatctt                                                      20

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
gcttctgctc cacctgac                                                        18

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
agctatgctg cagctgttac                                                      20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
atgcatgtcc aagtttcaag                                                      20

<210> SEQ ID NO 19
<211> LENGTH: 21

```
<212> TYPE: DNA
<213> ORGANISM: Artificial Sequence
<220> FEATURE:
<223> OTHER INFORMATION: primer

<400> SEQUENCE: 19
tccatggcta tattttgatg a                                             21

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
taagcctgcc agacacac                                                 18

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
cactctggac tttgcatctt                                               20

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
tgttggtttt caccgaata                                                19

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
agataaagaa agacacacac aact                                          24

<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24
gaaatcgcct gctacaaa                                                 18

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
```

```
tcagcttctt gccttcat                                                18
```

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26

```
taagtaagcc tgccagaca                                               19
```

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27

```
catcaaggtc ttttccaag                                               20
```

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28

```
cctgtctctg cccaagtc                                                18
```

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29

```
agggaacatt ttcaaaactc a                                            21
```

<210> SEQ ID NO 30
<211> LENGTH: 16
<212> TYPE: PRT
<213> ORGANISM: Artificial Sequence
<220> FEATURE:
<223> OTHER INFORMATION: peptide

<400> SEQUENCE: 30

```
Ile Lys Lys Glu Thr Lys Gly Lys Gly Ser Leu Glu Val Leu Asn Leu
1               5                   10                  15
```

<210> SEQ ID NO 31
<211> LENGTH: 16
<212> TYPE: PRT
<213> ORGANISM: Artificial Sequence
<220> FEATURE:
<223> OTHER INFORMATION: peptide

<400> SEQUENCE: 31

```
Cys Tyr Lys Asn Lys Val Val Gly Trp Arg Ser Gly Val Glu Lys Asp
1               5                   10                  15
```

<210> SEQ ID NO 32
<211> LENGTH: 20

```
<212> TYPE: DNA
<213> ORGANISM: Artificial Sequence
<220> FEATURE:
<223> OTHER INFORMATION: primer

<400> SEQUENCE: 32
gccttcactt tcttcatagt                                                  20

<210> SEQ ID NO 33
<211> LENGTH: 19
<212> TYPE: DNA
<213> ORGANISM: Artificial Sequence
<220> FEATURE:
<223> OTHER INFORMATION: primer

<400> SEQUENCE: 33
gcttgcctca aggaagtt                                                    19

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
cagccgacga ccttgtttt                                                   19

<210> SEQ ID NO 35
<211> LENGTH: 18
<212> TYPE: DNA
<213> ORGANISM: Artificial Sequence
<220> FEATURE:
<223> OTHER INFORMATION: primer

<400> SEQUENCE: 35
gtgccaacgc tgtgtttt                                                    18

<210> SEQ ID NO 36
<211> LENGTH: 719
<212> TYPE: DNA
<213> ORGANISM: Homo sapiens

<400> SEQUENCE: 36
gcgtaaaaag ccacaatacg caggcgtcat cgctcacttt tcccctcccg gcttctgctc      60
cacctgacgc ctgcgcagta agtaagcctg ccagacacac tgtgacggct gcctgaagct     120
agtgagtcgc ggcgccgcgc actggtggtt gggtcagtgc cgcgcgccga tcggtcgtta    180
ccgcgaggcg ctggtggcct tcaggctgga cggcgcgggt cagccctggt tcgccggctt    240
ctgggtcttt gaacagccgc gatgtcgatc ttcacccccca ccaaccagat ccgcctaacc    300
aatgtggccg tggtacggat gaagcgtgcc gggaagcgct tcgaaatcgc ctgctacaaa    360
aacaaggtcg tcggctggcg gagcggcgtg tgagtagccc cctccctcgg gcctgggcct    420
gggcctgagc cgtcacctcc gaggcggcct gtctctgccc aagtcgagtg aatgggccag    480
gctggggtgt tggccgggga ggaaatggaa cattcctgct gtgagcatga gacgtcgctg    540
tccgagcttg gcgcctaagc caagggtttc ttctttattt ggttggttcg gattgggttg    600
ttggtttggg gttttgtttt gttggtgtca taaaagctgc agccaagaaa tctcgtaatt    660
gtggtccttt tcctagaata atgatggctg agaacctagt cttacgaata ctgtcatag    719

<210> SEQ ID NO 37
```

<211> LENGTH: 733
<212> TYPE: DNA
<213> ORGANISM: Homo sapiens

<400> SEQUENCE: 37

```
aaatggtaag gcaaatacgg ttctgagttt tgaaaatgtt ccctcaggcc gatgcgggca        60
gttcacttga ggccaggagt tcgaggccag cctggccaac atgaaacccc atctctacta       120
aaaatacaaa gttagccggg tgtggtggcg catgcctgta atcccagtta ctcaggaggc       180
tgaggcggga gaatcacttg aacccgggag gctgaggtta cagtgacccg agatcgcgcc       240
attgcactcc agcctgggca aaaacagtga aattccatct aggggcgggg gttgggggggt      300
aagaaaaaga aaactgccct ctacactaaa ggtcatcagg gggatttgtt gtgtcttgcc       360
gttcatgttg ttgccatctc gtatttaaat gtaaatgcat gtccaagttt caagtatatt       420
cacataggac tttctctcct gccctcacaa gggaaaaaga cctcgatgaa gttctgcaga       480
cccactcagt gtttgtaaat gtttctaaag gtcaggttgc caaaaaggaa gatctcatca       540
gtgcgtttgg aacagatgac caaactgaaa tctgtaagca ggtgggtaac agctgcagca       600
tagctaaccc taataaccat ttataacgta tttgtagata tattaaacat taaaggctgt       660
ttttctggag gaaagactaa ccaagcaata atgtgaactg cacagtgtca cttctaataa       720
taaagaactt ggt                                                          733
```

<210> SEQ ID NO 38
<211> LENGTH: 899
<212> TYPE: DNA
<213> ORGANISM: Homo sapiens

<400> SEQUENCE: 38

```
gctcaaacca ttacttacat attgatagct ggagaggatg aaatttaatt ttctctccat        60
ccagttactc atttttttatg gttagttaat aaatagtgtg tgatagagaa agatagtgat      120
ttcttaaatg tgttggcatt ttttttagatt ttgactaaag gagaagttca agtatcagat     180
aaagaaagac acacacaact ggagcagatg tttagggaca ttgcaactat tgtggcagac       240
aaatgtgtga atcctgaaac aaagagacca tacaccgtga tccttattga gagagccatg       300
aaggacatcc actattcggt gaaaaccaac aagagtacaa aacagcaggt gagtggtttc       360
tcatgtcatc aaaatatagc catggaaatc agttttctct gaagaaatca ttaaaataat       420
gggtctgggg ccaggcacaa tggttcatgc ctgtaatcct agcactttgg gagccaagat      480
gggaggattg cttgaggcct ggaaacagcc tgggaaacat agggacgccc catctctaaa       540
tttttttttt ttttttttga cagagtct actctattg cccaggctgg agtgcagtag          600
tatgatctcg gctcactaca atctccacct cccgcgttca agcaagtctc ctgcctcagc       660
ctcctgagta gctgggatta taggcacgtg ccaccacact cagctaattt tgtattttta       720
gtagagttga ggtttcacca tgttggccag gctggtcttg aactcctgac cctaggtgat       780
ccgtccgcct tggcctccca aagtgctggg attacaggca tcagctaccg taccctacct       840
ctaaattttt taatataaaa aattaaattt aaaaaaatgg gtctgcatgg aagcaagtg        899
```

<210> SEQ ID NO 39
<211> LENGTH: 1488
<212> TYPE: DNA
<213> ORGANISM: Homo sapiens

<400> SEQUENCE: 39

```
aaagggtcat tttaacactt cttttttgaat tttttaattt atatataatt cacataccat       60
```

```
aaatttcaca ctcataaagt atgtacactt taagtggtat attaacaaag ttttggaacc      120
ttccctgcta cctggttcga gaacattttc atcaccacaa aaagaaagtc agtatccatt      180
agtagccatc ccccatttc cccccacagg cccctcccaa ccactaatct cctctcgtta       240
tggacttctc aattctggac atttcatata aatggaatca tacaatatgt ggccttttca      300
tggttcatac atgttgtaac ctgcatcagc atgtcatttc tttttatgc cggaataata       360 gcccactgta cggaaagaaa cacattttgt tcattcatct atcagttgat agacattggg      420 ttgcttcac ttttgagcta tgatgagcaa tgctgctata aatttcttg tatgtttctg        480 tgtagacata tgttttcatt tctgtatacc tggtgactac caaacctatt tctaaaacag      540
ctgcaccatt ttactttacc accatcagtg tttaagagtt cagtttctcc acatcctcag      600
taatacttgt cattgtctgc cttttgatg atggccatcc tggtggtatc ttgtcgtggt       660
tttgatttgc atttccttaa tgatgatttg agcatatttc catgtgctta ttggtgcctc      720
gtctgtcttc ttttgagaaa tctctgttca ggttctttgc ccaccccccc cgccctcttt      780
ttgcaaactc tgcctcccgg attcaagcaa ttctcctgcc tcagcctctt gagtagctgg      840
gattacaggc gtgcactacc cacccggct aatttttctt ttttgtatt tttagtggag        900 acggggtttc accatgttgg ccaggctggt ctcgaattcc tgaccttgtg atgcacccgc      960
ctcggcctcc caaagtgctg gaattacagg cgtgagccac cacacctggc cttcactttc     1020
ttcatagttt tttgaaacac aaaagctttt cttcttgata agtccaattt ttctattttt     1080
tttttaacgg tcacttatgt tcttaatgtt atacctaaga aaccattacc taatccaact     1140
acatggaaac tactttgttt ttgaaaacct tatgaaataa tatagtagaa gaaattgcat     1200
tctcgatttt gtcttggtag gctttggaag tgataaagca gttaaagag aaaatgaaga      1260 tagaacgtgc tcacatcagg cttcggttca tccttccagt caatgaaggc aagaagctga     1320
aagaaaagct caagccactg atcaaggtca tagaaagtga agattatggc caacagttag     1380
aaatcgtaag agtcaaatat tttctttgct tcatgttacc taaatattgt attctctagt     1440
aataaatttg tagcaaacat ttagatgttg taaacgtcag atattttc                  1488

<210> SEQ ID NO 40
<211> LENGTH: 1556
<212> TYPE: DNA
<213> ORGANISM: Homo sapiens

<400> SEQUENCE: 40
tccactgtag atgtgaacta actcatctga cactacttga agttctaaaa tctttgcaaa       60
actgtacaca tgggccaggc acagtggctc gtgcctgtaa tcccagcact ttgggaggcc      120
aaggtgagca gataacatgg tgaaacccta tctctactaa aaatacaaaa aataagccag      180
gtgtggtggt gggttcctgt aatcccagtt cttgggagg ctgaggcagg agaatcactt       240
gaacctggga ggcggaggct gcagtgagcc aagatcacac cactgcactc tatctcaaaa      300
aaaaataaat taacatacac atggtgtcta cataagtctt cacattgctt tttctccttc      360
atacgtggag gtgactttac tgagctataa aatgtaatgc taaattttag tatgagaaga     420
atcagagttt tctagtttgt cccttccatt tacagctgaa gaatcagaat aagtgtttaa      480
acatagggat taatgccttg tcacaggggg ctacatggac acttgagggc agaggctaaa     540
ctggaaccca gtgtgccgcc ctacccattg tcttatctat tgcaccatag aactgtggta     600
ttattagaga tctggacagc attgtgcttg cctcaaagga agttaaagct gagtttattc     660
```

-continued

```
tgtgtcttgc tcatcctcat gtggtaatct gctacgttaa atgtttcagg tatgtctgat       720
tgacccgggc tgcttccgag aaattgatga gctaataaaa aaggaaacta aaggcaaagg       780
ttctttggaa gtactcaatc tgaaagatgt agaagaagga gatgagaaat ttgaatgaca       840
cccatcaatc tcttcacctc taaaacacta aagtgtttcc gtttccgacg gcactgtttc       900
atgtctgtgg tctgccaaat acttgcttaa actatttgac attttctatc tttgtgttaa       960
cagtggacac agcaaggctt tcctacataa gtataataat gtgggaatga tttggtttta      1020
attataaact ggggtctaaa tcctaaagca aaattgaaac tccaagatgc aaagtccaga      1080
gtggcatttt gctactctgt ctcatgcctt gatagctttc caaaatgaaa gttacttgag      1140
gcagctcttg tgggtgaaaa gttatttgta cagtagagta agattattag gggtatgtct      1200
atacaacaaa agggggggtc tttcctaaaa aagaaaacat atgatgcttc atttctactt      1260
aatggaactt gtgttctgag ggtcattatg gtatcgtaat gtaaagcttg gatgatgttc      1320
ctgattatct gagaaacaga tatagaaaaa ttgtgccgga cttacctttc attgaacatg      1380
ctgccataac ttagattatt cttggttaaa aaataaaagt cacttatttc taattcttaa      1440
agtttataat atatattaat atagctaaaa ttgtatgtaa tcaataaaac cactcttatg      1500
tttattaaac tatggcttgt gtttctagac aacttcctaa ctcccttctt tttctc        1556
```

<210> SEQ ID NO 41
<211> LENGTH: 720
<212> TYPE: DNA
<213> ORGANISM: Homo sapiens

<400> SEQUENCE: 41

```
gcggtaaaag ccacaatgcg caggcgtcat cgctcacttc tcccctcccg gcttctgctc        60
cacctgacgc ctgcgcagta agtaagcctg ccagacacgc tgtggcggct gcctgaagct       120
agtgagtcgc ggcgccgcgc acttgtggtt gggtcagtgc cgcgcgccgc tcggtcgtta       180
ccgcgaggcg ctggtggcct tcaggctgga cggcgcgggt cagccctggt ttgccggctt       240
ctgggtcttt gaacagccgc gatgtcgatc ttcaccccca ccaaccagat ccgcctaacc       300
aatgtggccg tggtacggat gaagcgcgcc aggaagcgct tcgaaatcgc ctgctacaga       360
aacaaggtcg tcggctggcg gagcggcttg tgagtagccc cctccctcgg gcctgggcct       420
gggcctgagc cgtcacctcc gaggcggcct gtctctgccc aagtcgagtg aatgggccag       480
gctggggtgt ttgttggccc gggaggaaat ggaacattcc tgctgtgagc atgagacgtc       540
gctgtccgag cttgcgcct aagccaaggg tttctttatt tggttggttc cgattgggtt       600
gttggtttgg ggttttgttt tgttggtgtc ataaaagctg cagccaagaa atctcataat       660
tgtggtcctt ttcctagaat aatgatggct gagaacctag tgttccgaat actgtcatag       720
```

<210> SEQ ID NO 42
<211> LENGTH: 722
<212> TYPE: DNA
<213> ORGANISM: Homo sapiens

<400> SEQUENCE: 42

```
aaatggtagg gcaaatacag ttctgagttt tgaaaatgtt ccctcaggcc gatgcgggca        60
gatcacttga ggccaggagt tcgaggccag cctggccaac atgaaacacc atctctacta       120
aaaatacaaa attagccggg tgtggtggcg catgcctgta atcccagcta ctcaggaggc       180
tgaggcagga gaatcacttg aacccgggag gcggacgttg cagtgagccg agatcgcgcc       240
attgcactcc agcctgggca aaaacagtga aattccatct aagggcgggg ggggaagaa        300
```

| | |
|---|---:|
| aactgccctc tacactaaag gtcatcaggg ggatttgttg tgtcttgccg ttcatgttgt | 360 |
| tgccatctcg tatttaaatg taaatgcatg tccaagtttc aagtatattc acataggact | 420 |
| ttctctcctg ccctcacaag ggaaaaagac cttgatgaag ttctgcagac ccactcagtg | 480 |
| tttgtaaatg tttcctaagg tcaggttgcc aagaaggaag atctcatcag tgcgtttgga | 540 |
| acagatgacc aaactgaaat ctgtaagcag gcgggtaaca gctgcagcat agctaaccct | 600 |
| aataaccatt tataacgtat ttgtagatat attaaacatt aaaggctgtt tttctggagg | 660 |
| aaagactaac caagcaataa tgtgaactgc acaatatcac ttctaataat aaagaacttg | 720 |
| gt | 722 |

<210> SEQ ID NO 43
<211> LENGTH: 904
<212> TYPE: DNA
<213> ORGANISM: Homo sapiens

<400> SEQUENCE: 43

| | |
|---|---:|
| gctcaaacca ttacttacat attaatagct ggagaggatg aaatttaatt ttctccccag | 60 |
| ttactcattt tttgtcgtta gttaataaat agtgtgtgat agagaaagat agtgatttct | 120 |
| taactgtgtt ggcattttt tagattttga ctaaaggaga agttcaagta tcagataaag | 180 |
| acacacacaa ctggagcaga tgtttaggga cattgcaatt attgtggcag acaaatgtgt | 240 |
| gactcctgaa acaaagagac catacaccgt gatccttatt gagagagcca tgaaggacat | 300 |
| ccactatttg gtgaaaacca acaggagtac aaaacagcag gtgagtggtc tctcatgtca | 360 |
| tcaaaatata gccatggaaa tcagtttct ctgaagaaat cattaaaata atgggtctgg | 420 |
| ggccaggcac aatggttcat acccgtaatc ctagcacttt gggagccaag atgggaggat | 480 |
| tgcttgaggc ctggaaacag cctgggaaac atagggacgc ccatctcta aattttttg | 540 |
| tttattgttg ttttttttgtt tgagacagag tcgcactgtg ttgcccaggc tggagtgcag | 600 |
| tggcacgatc tcggctcact tacaatctcc acctcccgcg ttcaagcaag tctcctgcct | 660 |
| cagcctccca gtagctggg attataggca cgcgccacca cacccagcta attttgttat | 720 |
| ttttagtaga gttgaggttt taccatgttg gccaggctgg tcttgaactc ctgacctcag | 780 |
| gtgatccgtc cgccttggcc tcccaaagtg ctggggattac aggcatcagc taccgtaccc | 840 |
| tacctctaat tttttaata taaaaaatta aatttaaaaa aatgggtttg catggaagca | 900 |
| agtg | 904 |

<210> SEQ ID NO 44
<211> LENGTH: 1527
<212> TYPE: DNA
<213> ORGANISM: Homo sapiens

<400> SEQUENCE: 44

| | |
|---|---:|
| aaagggtcat tttaacacct ctttttgaat tttcaattt acatataatt cacatacaat | 60 |
| aaatttcaca ctcataaagt gtgtacactt taagtggtat attaacaaag tttgggaacc | 120 |
| ttccctgcta cctggtttga gaacattttc atcaccacaa aaagaaagtc agtatccatt | 180 |
| agtagctatc ccccatttc ccccacagg cccttcccaa ccactaatct cctgtcgtta | 240 |
| tggacttgtc aattctggac atttcatata atggaatca tacaatatat ggccttttca | 300 |
| gggttcatac atgttgtaac ctgcatcagc atgtcatttc ttttttatgc cggaataata | 360 |
| gcccactgta cggaaaaaaa catattttgt tcattcattt atcagttgat agacattggg | 420 |

-continued

```
ttgctttcac ttttgagcta tgatgagcaa tgctgctata aaatttcttg tatgtttttg        480
tgtagacata tattttcatt tctgtatacc tggggactac caaacctatt tctaaaacag        540
ctgcaccatt ttacattacc accaacagcg tttaagagtt cagtttctcc acatcctcag        600
taatacttgt cattgtctgt cttttgatg atggccatcc tggtggtatc ttgtcgtcgt         660
tttgatttgc atttccttaa taatgatttg agcatatttc catgtgctta ttggtgcctc        720
gtctgtctgc ttttgagaaa tctctgttca ggttctttgc cccttttta ttctcgctct         780 gtcacccaga ctagagtgca gtggcgcgat ctcggctcat tgcaaactct gcctcccgga        840
ttcaagcaat tctcctgcct cagcctcttg agtagctggt actacaggcg tgtgctacca        900
cacccggcta attttctttt tttgtattt ttagtagaga cggggtttca ccatgttggc         960
caggctggtc tcgaatttct gaccttgtga tgcacccgcc tcggcctccc aaagtgctgg       1020
gattagaggc gtgagccacc acacctggcc ttcactttct tcataattt ttgaaacaca       1080 aaagcttttc ttcttgataa gtccaatttt tctatttttt tttaacggtc acttatgttc       1140
ttaatgttat acctaagaaa ccattaccta atccaactac atggaaacta ctttgttttt       1200 gaaaaccttta tgaaataata tagtagaaga aattgcattc tcgattttgt cttggtaggc     1260
tttggaagtg ataaagcagt taaaagagaa atgaagata gaacgtgctc acatgaggct       1320
tcagttcatc cttccagtga atgaaggcaa gaagctgaaa gaaaagctca agccactgat       1380
caaggtcata gaaagtaaag attatggcca acagttagaa atcgtaagag tcaaatattt       1440
tctttgcttc atgttaccta aatattgtat tctctagtaa taaatttgta gcaaacattc       1500
agacattgta aacagtcaga tattttc                                           1527
```

<210> SEQ ID NO 45
<211> LENGTH: 1553
<212> TYPE: DNA
<213> ORGANISM: Homo sapiens

<400> SEQUENCE: 45

```
tccactgtag atgtgaacta acccatctga cactacttga agttctaaaa tctttgcaaa         60
actgtacacg tgggccaggc acagtggctc atacctgtaa tcccagcact ttgggaggcc        120
gaggcgagca gataacacgg tgaaaccctg tctctactaa aaatacaaaa ataagccag         180 gtgtggtggt gggcgtctgt aatcccagtg tcttgggagg ccgaggcagg agaatcactt        240
gaacctggga ggtggaggct gcagtgagcc aagatcacac cactgcactc tatctcaaaa        300
aaaaaataaa acaaaaacat acacatggtg tctacgtaag tcttcacatt gctttttctc        360
cttcatacgt ggaggtgact ttactgagct ataaaatgta atgctaaatt ttagtatgag        420
aagaatcaga gttttctagt ttgtcccttc catttacagc ggaagaatca gaataagtgt        480
ttaaacatag ggattaatgc cttgtcacag ggggctacat ggatacttga gggcagaggc       540
tgaactggaa cccagtgtgc cgccctaccc attgtcttat ctattgcacc atagaactgt        600
ggtattagag atctggacag cattgtgctt gcctcaaagt taaagctgag tttattctgt       660
gtcttgctca tcctcatttg gtaaactgct acgttaaatg tttcaggtat gtctgattga       720
cctgggctgc ttccgagaaa ttgatgagct aataaaaaag gaaaccaaag gcaaaggttc       780
tttggaagta ctcaatctga aagatttgaa gaaggagatg agaaatttga atgacaccca       840
tcagtctctt cacctctaaa acactaaagt gttttcgttt ccaacagcac tgtttcatgt       900
ctgtggtctg ccaaatactt gctcaaacta tttgacattt tctatctttg tgttaacagt        960
ggacacagca aggctttcct acataagtat aataatgtgg gaatgatttg gtttaatta      1020
```

-continued

```
taaactgggg tctaaatcct aaagcaaaat tgaaactcca ggatgcaaaa tccagagtgg   1080
cattttgcta ctctgtctca tgccttgata gctttccaaa atgaaagtta cttgaggcag   1140
ctcttgtggg tgaaaagttt tttgtacagt agagtaagat tattagggg atgtctatac    1200 gacaaaaggg gggtctttcc taaaaaagaa aacatgatgc ttcatttcta cttaatggaa   1260
cttgtgttct gagggtcatt atggtatcgt aatataaagc ttggatgatg ttcctgatta   1320
tctgagaaac agatatagaa aaattgtgtc ggacttaaat aattttcgtt gaacatgctg   1380
ccataactta gattattctt ggttaaaaaa taaaagtcac ttatttctaa ttcttaaagt   1440
ttataatata tattaatata gctaaaattg tatgtaatca ataaaaccac tcttatgttt   1500
attaaactat ggcttgtgtt ctagacaac ttcctaactc cctttcttt ctc            1553

<210> SEQ ID NO 46
<211> LENGTH: 723
<212> TYPE: DNA
<213> ORGANISM: Mus musculus

<400> SEQUENCE: 46
aacgacccgc cttcctttga ggtgcctggg tggaactaga gggcgtaaaa agtcacggcg     60
cgcaggcgtg gttgctttct tatcggccta gtgcgccact tgacgcatgt gcagtagggc    120
aatcgggcgt gcggtagctt cttccctggt aggttccgga agagccgcgc actccttggg    180
cgttaagggt tcgcgcgccg cagggtcgtt tcagccgagc acttggcgtc ccctcgagct    240
cgagatctgt gaacagccac catgtcgatc ttcacccccca ccaaccagat ccgactgacc    300
aatgtggccg tggtgcggat gaagcgggga gggaagcgct tcgaaatcgc ctgctataaa    360
aacaaggtcg tcggctggcg gagtggcgtg tgagtaatcc tgtgcccaga gttcggcggc    420
ctggcctccc taaccccggc tcctgcgacc catcggtacc tttcaggcct ggtttacccg    480
attcggattg ggttctgctt tgggattttg ttagtatcat aaaaactgcc aactacaaac    540
gccatcagag ccgggtggga ccgatggttt aggcctgtaa tcccagcgcc caggaaactg    600
aggcaggagg attgctgcga tttccaggcc agcctggaac gtgtgtgtgt gtgtatgtgt    660
atgtgtgtgt tgtgtgtgtg tatgtgtatg tgtgtgtgag agagaccgtg accgaccctg    720
tac                                                                  723

<210> SEQ ID NO 47
<211> LENGTH: 733
<212> TYPE: DNA
<213> ORGANISM: Mus musculus

<400> SEQUENCE: 47
gtagtgtctt cgctactgcc atctagggac agatattcca ggacagaaga aacaccactc     60
cccaccacac cctgagtttc cttacataaa acaatgatgt agttttttccc tctgtggtga    120 agtgggagaa tccagatact gtccttcgca ggtagccacc agagagagag tgtggtgtgt    180
gtgtgtgtga gatttctctt tttttttttc tttagggttt ttgttttgtt ttttttttgtt    240 ttgtttggtt tttttttttt tttttttga gactggcctc aaactcccaa tttccctgcc     300
tctgcctcct aaatggtgag ttacagatgt gcacatcaca cccagcttgc agcacttgcc    360
atttctcttg ttgctatctt gtgtttaaat gtgagtggat tttcttacta tccagtggat    420
cacataggac tttctctcct gcccctttcaa gggaaaaaga ccttgatgaa gttctgcaga   480
cccattcagt gtttgtaaat gtttccaaag gtcaggttgc caagaaggaa gacctcatca    540
```

-continued

| | |
|---|---|
| gtgcatttgg gacagacgac cagactgaaa tctgcaagca ggtaggtcct gccaggtgca | 600 |
| atgtaacaaa atctcacgat ggtaggcaac atctggacca ctgtgtttac tgttttcctt | 660 |
| gatgagtttt tgttgtttta gcatttgttg ggtccctccc acctccagtt tatattgttg | 720 |
| ggcaatttgg gga | 733 |

<210> SEQ ID NO 48
<211> LENGTH: 912
<212> TYPE: DNA
<213> ORGANISM: Mus musculus

<400> SEQUENCE: 48

| | |
|---|---|
| tgtaagctgc tgctgggtta aggcagcacg tggttctgcg tgagcagctg cagtggacgc | 60 |
| cgcctccctt cctccccgct acctacctgt gcagtagaga gatacccaga actgatgagg | 120 |
| gctttctcta tgttctgcca tctttagatt ttgactaaag gagaagttca agtgtcagat | 180 |
| aaagaacggc acacacagct ggagcagatg tttaggata tcgccaccat tgtggcagac | 240 |
| aagtgtgtga acccagaaac aaagagacct tacaccgtta tcctcatcga gagagccatg | 300 |
| aaggacatcc actactccgt gaaacccaac aagagcacaa agcaacaggt aagggttcct | 360 |
| tgttgtcctc gggacctaag gccatggaag tgcctgatgc gcctgcctcc ctatctctgg | 420 |
| tgctggggtc agcagcacac acttccaggc tgcctggctg tgctggtgct catcattctg | 480 |
| agcagaccct ctcccggctg agccataccc ttagctgctg ctcctcagtg tgacggaaca | 540 |
| caaatacaca cagaactctt tttgtttgtt tgtttgtttg ggggttttt ttttttttt | 600 |
| ttagttttgt ttttggtctt tcgagacagg gtttctctgt attgccctgg ctgtcctgga | 660 |
| actcgctctg tagcccaggc tggcctcgaa ctcagaaatc cgcctgcctc tgcctcccaa | 720 |
| gtgctgggat taaaggcgtg ggccaccaca cctggctcat acagaactct tatttcctgc | 780 |
| ccagctcaaa cctttaaaga gaaagcttgg actttgagtc acctgagccc ttttgctgtt | 840 |
| tgtgtttatt aacatatttc ctacagctca gccctgtcac gccagccatt ctgctggcct | 900 |
| ggattccaag ca | 912 |

<210> SEQ ID NO 49
<211> LENGTH: 1528
<212> TYPE: DNA
<213> ORGANISM: Mus musculus

<400> SEQUENCE: 49

| | |
|---|---|
| ctcaaaagaa ataacaagtc gggtgtggtg gtgcacacct ttaatcccag cactcgggag | 60 |
| gcagaggcag gcgaatttct gagttggagg ccagcctgag ttccaggaca gccagggcta | 120 |
| tacagagaaa ccctgtctcg aaaaaccaaa aaaaaaaaa aaaaaaaaa aagaaggaag | 180 |
| aaagaaagaa agcaagcaag caagcaagcg agcaatggtg tttcacagca cgaagtatag | 240 |
| tatgacccat ataactaaca gcctgcctga gttattactg cttaggcagt ggcctgactt | 300 |
| agacctgatc atgtacgtcc agaaaaggcc tggtggaaaa ctggaaggag ccagagaaga | 360 |
| acctccatac acaagaactc tgggcaacct cagaactact catgtccatt ccacaaccca | 420 |
| accaggggct tctctgtaca gggaacaagc acaggagagt catcaaggga ctaacgagct | 480 |
| cacatcgacc acctgtgcac tgttcccctc tccataaacc tcagattgca caagctcagc | 540 |
| cccgtctcc tccacatcca gctgccagtg actgacgctg cctgcgggtc agtggcagag | 600 |
| gtgccaaggc aaaggcctgt gaggacctta ctgtgtatca ctaggcgtcc cagcactctg | 660 |
| gatgactgtt attagacttt cagggaagcc actagttctt ctacccagtg acagcttctc | 720 |

| | |
|---|---|
| aggcacgggt gtccacagag tgggaagggc cttgctggac ggctggtggg aagctctggg | 780 |
| ccatttcccc aaggagcatg tctctgctct caccactgtt agaattactg tgaactcagc | 840 |
| tatgggctca ggtcctcaag gttcatggct taaaacaggg ttggcttaga agtctccgag | 900 |
| gccaacaaaa agacattttg tctgttctag agatgtacga aattcccacc gcacacattt | 960 |
| tcttgctttt agagagctga ggacagccca ggtcctcgtg catgctgggt agttgcttca | 1020 |
| ccactgaact gagtcccagc ctttaacgtt gctttctgcc gaagcaaaaa ttattttttt | 1080 |
| ttccatttca caaatgagca cactagctca tttttaggg atttctagga ttgctggtac | 1140 |
| cttggctgta aaactgctgg cataaggcag ctatgtggaa actgctttgt tcatgtctaa | 1200 |
| catataaatt tgtgcagcac aaaaactaag taacgagcac cccttgttct gtcttaaagg | 1260 |
| cttttggaagt gataaagcag ctgaaagaga agatgaagat agagcgggcc cacatgcgat | 1320 |
| tgcgcttcat cctgccagtg aacgaaggga agaagctgaa ggagaagctg aagccactga | 1380 |
| tgaaggtggt ggagagtgag gactacagcc agcagctgga gatcgtaaga tgatggtggc | 1440 |
| ggggagcagg tggcgcagcc aaggtcccat gattatgacc ttaacacatt attattcttg | 1500 |
| gcttccttct acccaaatag cctcgttc | 1528 |

<210> SEQ ID NO 50
<211> LENGTH: 1440
<212> TYPE: DNA
<213> ORGANISM: Mus musculus

<400> SEQUENCE: 50

| | |
|---|---|
| gtatactgtg gctgtcttca gacacagcag aaggcatcgg atcccattac agatggttgt | 60 |
| gagccacttg tggttgctgg gaattgagct cagaacctct ggaagagcag ccagtgctga | 120 |
| gcatctctac agcctctgaa cccgggtctt gatgctaagc agtgctcact ctcagtatga | 180 |
| gctgcagcac tggccaggtg agtcttcaag ggtgtcttaa tcaggctttt actgctgtga | 240 |
| acagacacca ggaccaatgc aagtcttata agaacaaca tttagttgag tctggcttac | 300 |
| aggttcagag gttcagtcca ttatcaaggt gggagcatgg tagtatccag gtgggaatga | 360 |
| tacaggaggg gctgagagtt cgacatcttc atctgaaggc tgctagcaga atactgactt | 420 |
| cgaggctgtt aggatgaggg tcttaaagcc tatgaccaca gggacacacc ttctaatagt | 480 |
| gtcactcccc gggctgagca tatacaaacc gtaacacggg ataagtgcct ttcccaaagt | 540 |
| ccaacagtag gtgcttagaa tcgagacaga accccaggcc cagcctgctg ccctggcctc | 600 |
| catgtgagca gcacctagaa cacagtcata gatctgccct gagcattcaa actgggctta | 660 |
| ttctgtgccg atgcccatct tcccttggaa accagctgtg ttactcattg caggtgtgcc | 720 |
| tcatcgaccc aggctgcttc agagaaattg atgagctaat aaaaaaggaa acgaaaggca | 780 |
| ggggttctct ggaagtgctc agtctgaagg acgtggagga aggcgatgag aagtttgaat | 840 |
| gacaccgccc ggctcctcaa ctggagcacg accgaggacg cttgttcctc acagcagcag | 900 |
| ctcgttctgt gacctgccaa acgccctgct cacgcgacgt gccactttcc atcttgtgtt | 960 |
| aaacatttac ccaggtacct gggtattttt gttgtcaatt ggggtttcca gcaaaaatga | 1020 |
| aaaataacct aaaatacaga gtccagaaca gctgctcact gctgcgtctg cctttctagt | 1080 |
| tccaggggac cagagacagc attggtggat aagaaggtag agttagtcca tgacagatca | 1140 |
| ttggagaggg gtctgaataa caagggggt acgcctgctg gaaagaagat ggggtgtttc | 1200 |
| tgaataatga agtgcaggta tggggtgtga gcatggagag aagagttcct gggtccctcc | 1260 |

-continued

```
caatagattt ataatgacta gggagaattt gactttctaa ttttcaacca acatgctacc    1320
aaaactgact tagattattc ttgggaaaat atatacagtc atttaatact aattcttaaa    1380
ggtttataat atatgttagt atagttaaaa ttctatgtaa tcaataaaac ttatttttac    1440
```

We claim:

1. A method for determining whether a subject is suffering from Shwachman-Diamond Syndrome (SDS) or is an SDS carrier comprising obtaining a nucleic acid sample from the subject, and conducting an assay on the nucleic acid sample to determine the presence or absence of a Shwachman-Bodian-Diamond-Syndrome (SBDS) gene mutation associated with SDS selected from the group consisting of 183TA>CT, 183TA>CT+258+2T>C, and 258+2T>C, and wherein the presence of said SBDS gene mutation associated with SDS in both SBDS alleles indicates that the subject suffers from SDS and the presence of a SBDS gene mutation associated with SDS in one SBDS allele indicates that the subject is an SDS carrier.

2. The method of claim 1 wherein the assay is selected from the group consisting of probe hybridisation, direct sequencing, restriction enzyme fragment analysis and fragment electrophoretic mobility.

3. The method of claim 2 wherein the nucleic acid sample is a DNA sample or an RNA sample and the assay is a direct sequencing assay.

4. The method of claim 3 wherein the nucleic acid sample is a genomic DNA sample and the assay comprises the steps of:
   (a) amplifying a target portion of the nucleotide sequence of the genomic DNA;
   (b) obtaining the nucleotide sequence of said amplified target portion; and
   (c) determining the presence or absence of said SBDS gene mutation associated with SDS in said target portion of the nucleotide sequence.

5. The method of claim 3 wherein the nucleic acid sample is an RNA sample and the assay comprises the steps of:
   (a) reverse transcribing the RNA sample to produce a corresponding cDNA;
   (b) performing at least one polymerase chain reaction with suitable oligonucleotide primers to amplify the SBDS cDNA;
   (c) obtaining the nucleotide sequence of the amplified SBDS cDNA; and
   (d) determining the presence or absence of said SBDS gene mutation associated with SDS in said nucleotide sequence.

6. The method of claim 4 wherein the target portion of the nucleotide sequence is amplified using a primer pair selected from the group consisting of:

(a)
GCGTAAAAAGCCACAATAC and                       (SEQ ID NO: 3)

CTATGACAGTATTCGTAAGACTAGG;                    (SEQ ID NO: 4)

-continued (b)
AAATGGTAAGGCAAATACGG and                      (SEQ ID NO: 7)

ACCAAGTTCTTTATTATTAGAAGTGAC;                  (SEQ ID NO: 8)

(c)
GCTCAAACCATTACTTACATATTGA and                 (SEQ ID NO: 9)

CACTTGCTTCCATGCAGA;                           (SEQ ID NO: 10)

(d)
GCCTTCACTTTCTTCATAGT and                      (SEQ ID NO: 31)

GAAAATATCTGACGTTTACAACA;                      (SEQ ID NO: 12)

(e)
GCTTGCCTCAAAGGAAGTT and                       (SEQ ID NO: 32)

CACTCTGGACTTTGCATCTT;                         (SEQ ID NO: 14)

(f)
TAAGCCTGCCAGACACAC and                        (SEQ ID NO: 19)

CTATGACAGTATTCGTAAGACTAGG;                    (SEQ ID NO: 4)

(g)
AAAGGGTCATTTTAACACTTC and                     (SEQ ID NO: 11)

GAAAATATCTGACGTTTACAACA;                      (SEQ ID NO: 12)

(h)
TCCACTGTAGATGTGAACTAACTC and                  (SEQ ID NO: 13)

CACTCTGGACTTTGCATCTT;                         (SEQ ID NO: 14)
and (i)
CAGCCGACGACCTTGTTTT and                       (SEQ ID NO: 33)

GTGCCAACGCTGTGTTTT.                           (SEQ ID NO: 34)

7. The method of claim 2 wherein the nucleic acid sample is a DNA sample and the assay is a restriction enzyme fragment analysis.

8. The method of claim 7 wherein the assay comprises the steps of:
   (a) digesting the DNA with a restriction enzyme to give restriction fragments;
   (b) separating the restriction fragments by agarose gel electrophoresis; and
   (c) detecting the separated fragments by hybridisation of the fragments to a detectably labelled nucleotide probe specific for SBDS.

9. The method of claim 8, wherein the method is for determining whether a subject is suffering from SDS and wherein the restriction enzyme is at least one of Cac81 and Bsu361.

10. The method of any one of claims 1 to 9 wherein the subject is a human subject.

11. The method of claim 8, wherein the method is for determining whether a subject is an SDS carrier and wherein the restriction enzyme is Nde 1.

* * * * *